United States Patent
Wipf et al.

(10) Patent No.: US 10,526,280 B2
(45) Date of Patent: Jan. 7, 2020

(54) (2-AMINO-4-(ARYLAMINO)PHENYL CARBAMATES

(71) Applicant: University of Pittsburgh—Of the Commonwealth System of Higher Education, Pittsburgh, PA (US)

(72) Inventors: Peter Wipf, Pittsburgh, PA (US); Athanassios Tzounopoulos, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 15/526,668

(22) PCT Filed: Nov. 13, 2015

(86) PCT No.: PCT/US2015/060627
§ 371 (c)(1),
(2) Date: May 12, 2017

(87) PCT Pub. No.: WO2016/077724
PCT Pub. Date: May 19, 2016

(65) Prior Publication Data
US 2018/0127357 A1    May 10, 2018

Related U.S. Application Data

(60) Provisional application No. 62/079,430, filed on Nov. 13, 2014.

(51) Int. Cl.
| | | |
|---|---|---|
| C07C 271/28 | (2006.01) | |
| C07D 305/06 | (2006.01) | |
| C07D 333/20 | (2006.01) | |
| C07D 277/28 | (2006.01) | |
| A61P 25/28 | (2006.01) | |
| A61P 27/16 | (2006.01) | |
| A61P 1/00 | (2006.01) | |
| A61P 25/00 | (2006.01) | |
| C07B 59/00 | (2006.01) | |
| C07C 323/33 | (2006.01) | |

(52) U.S. Cl.
CPC .............. *C07C 271/28* (2013.01); *A61P 1/00* (2018.01); *A61P 25/00* (2018.01); *A61P 25/28* (2018.01); *A61P 27/16* (2018.01); *C07B 59/001* (2013.01); *C07C 323/33* (2013.01); *C07D 277/28* (2013.01); *C07D 305/06* (2013.01); *C07D 333/20* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 5,384,330 A | 1/1995 | Dieter et al. | |
| 6,348,486 B1 | 2/2002 | Argentieri et al. | |
| 8,916,133 B2 * | 12/2014 | Duggan | C07C 271/28 424/1.89 |
| 2002/0111379 A1 | 8/2002 | Bowlby et al. | |

(Continued)

FOREIGN PATENT DOCUMENTS

| | | |
|---|---|---|
| WO | WO 01/01973 | 1/2001 |
| WO | WO 02/49628 | 6/2002 |

(Continued)

OTHER PUBLICATIONS

Cederroth, et al., "Hearing loss and tinnitus—are funders and industry listening?" *Nature Biotechnology*, vol. 31, pp. 972-974, Nov. 8, 2013.

(Continued)

*Primary Examiner* — Heidi Reese
(74) *Attorney, Agent, or Firm* — Klarquist Sparkman, LLP

(57) ABSTRACT

A compound, or pharmaceutically acceptable salt thereof, having a formula I of:

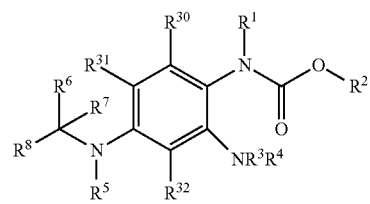

wherein $R^1$ is H or optionally-substituted alkyl;

$R^2$ is optionally-substituted alkyl;

$R^3$ and $R^4$ are each independently H or optionally-substituted alkyl;

$R^5$ is H, optionally-substituted alkyl, acyl, or alkoxycarbonyl;

$R^6$ and $R^7$ are each independently H, deuterium, optionally-substituted alkyl, or $R^6$ and $R^7$ together form a carbocyclic;

$R^8$ is optionally-substituted thiazolyl, optionally-substituted thiophenyl, or substituted phenyl, provided that if $R^8$ is 4-halophenyl, then $R^2$ is substituted alkyl or branched alkyl or at least one of $R^6$ or $R^7$ is not H; and $R^{30}$, $R^{31}$ and $R^{32}$ are each independently H, deuterium, halogen, substituted sulfanyl, or optionally-substituted alkoxy.

50 Claims, 9 Drawing Sheets

(56) References Cited

U.S. PATENT DOCUMENTS

| | | |
|---|---|---|
| 2002/0183395 A1 | 12/2002 | Argentieri et al. |
| 2013/0287686 A1 | 10/2013 | Duggan et al. |

FOREIGN PATENT DOCUMENTS

| | | |
|---|---|---|
| WO | WO 2004/058739 | 7/2004 |
| WO | WO 2007/090409 | 8/2007 |
| WO | WO 2009/015667 | 2/2009 |
| WO | WO 2011/012659 | 2/2011 |
| WO | WO 2013/007698 | 1/2013 |

OTHER PUBLICATIONS

CAS Registry No. 400010-61-9 cited in Written Opinion issued for International Application No. PCT/US2015/060627 in reference to WO 02/49628 published Jun. 27, 2002.
CAS Registry No. 400010-62-0 cited in Written Opinion issued for International Application No. PCT/US2015/060627 in reference to WO 02/49628 published Jun. 27, 2002.
CAS Registry No. 400010-63-1 cited in Written Opinion issued for International Application No. PCT/US2015/060627 in reference to WO 02/49628 published Jun. 27, 2002 and WO 2004/058739 published Jul. 15, 2004.
CAS Registry No. 400010-64-2 cited in Written Opinion issued for International Application No. PCT/US2015/060627 in reference to WO 02/49628.
CAS Registry No. 721943-34-6 cited in Written Opinion issued for International Application No. PCT/US2015/060627 in reference to WO 2004/058139 published Jul. 15, 2004.
CAS Registry No. 721943-35-7 cited in Written Opinion issued for International Application No. PCT/US2015/060627 in reference to WO 2004/058139 published Jul. 15, 2004.
CAS Registry No. 721943-36-8 cited in Written Opinion issued for International Application No. PCT/US2015/060627 in reference to WO 2004/058139 published Jul. 15, 2004.
CAS Registry No. 721943-37-9 cited in Written Opinion issued for International Application No. PCT/US2015/060627 in reference to WO 2004/058139 published Jul. 15, 2004.
CAS Registry No. 721943-39-1 cited in Written Opinion issued for International Application No. PCT/US2015/060627 in reference to WO 2009/015667 published Feb. 5, 2009 and WO 2004/058139 published Jul. 15, 2004.
CAS Registry No. 721943-41-5 cited in Written Opinion issued for International Application No. PCT/US2015/060627 in reference to WO 2009/015667 published Feb. 5, 2009 WO 2004/058139 published Jul. 15, 2004.
CAS Registry No. 721943-42-6 cited in Written Opinion issued for International Application No. PCT/US2015/060627 in reference to WO 2009/015667 published Feb. 5, 2009 WO 2004/058139 published Jul. 15, 2004.
CAS Registry No. 721943-46-0 cited in Written Opinion issued for International Application No. PCT/US2015/060627 in reference to WO 2009/015667 published Feb. 5, 2009 and WO 2004/058139 published Jul. 15, 2004.
CAS Registry No. 721943-47-1 cited in Written Opinion issued for International Application No. PCT/US2015/060627 in reference to WO 2009/015667 published Feb. 5, 2009 and WO 2004/058139 published Jul. 15, 2004.
CAS Registry No. 721943-48-2 cited in Written Opinion issued for International Application No. PCT/US2015/060627 in reference to WO 2009/015667 published Feb. 5, 2009 and WO 2004/058139 published Jul. 15, 2004.
CAS Registry No. 721943-49-3 cited in Written Opinion issued for International Application No. PCT/US2015/060627 in reference to WO 2009/015667 published Feb. 5, 2009 and WO 2004/058139 published Jul. 15, 2004.
CAS Registry No. 721943-50-6 cited in Written Opinion issued for International Application No. PCT/US2015/060627 in reference to WO 2009/015667 published Feb. 5, 2009 and WO 2004/058139 published Jul. 15, 2004.
CAS Registry No. 721943-51-7 cited in Written Opinion issued for International Application No. PCT/US2015/060627 in reference to WO 2009/015667 published Feb. 5, 2009 and WO 2004/058139 published Jul. 15, 2004.
CAS Registry No. 721943-52-8 cited in Written Opinion issued for International Application No. PCT/US2015/060627 in reference to WO 2009/015667 published Feb. 5, 2009 and WO 2004/058139 published Jul. 15, 2004.
CAS Registry No. 721943-53-9 cited in Written Opinion issued for International Application No. PCT/US2015/060627 in reference to WO 2009/015667 published Feb. 5, 2009 and WO 2004/058139 published Jul. 15, 2004.
CAS Registry No. 721943-55-1 cited in Written Opinion issued for International Application No. PCT/US2015/060627 in reference to WO 2009/015667 published Feb. 5, 2009 and WO 2004/058139 published Jul. 15, 2004.
CAS Registry No. 721943-60-8 cited in Written Opinion issued for International Application No. PCT/US2015/060627 in reference to WO 2009/015667 published Feb. 5, 2009 and WO 2004/058139 published Jul. 15, 2004.
CAS Registry No. 721943-61-9 cited in Written Opinion issued for International Application No. PCT/US2015/060627 in reference to WO 2009/015667 published Feb. 5, 2009 and WO 2004/058139 published Jul. 15, 2004.
CAS Registry No. 721943-62-0 cited in Written Opinion issued for International Application No. PCT/US2015/060627 in reference to WO 2009/015667 published Feb. 5, 2009 and WO 2004/058139 published Jul. 15, 2004.
CAS Registry No. 721943-63-1 cited in Written Opinion issued for International Application No. PCT/US2015/060627 in reference to WO 2009/015667 published Feb. 5, 2009 and WO 2004/058139 published Jul. 15, 2004.
CAS Registry No. 945828-50-2 cited in Written Opinion issued for International Application No. PCT/US2015/060627 in reference to WO 2009/015667 published Feb. 5, 2009, and WO 2007/090409 published Aug. 16, 2007.
Damgaard et al., "Extrasynaptic GABAA receptor activation reverses recognition memory deficits in an animal model of schizophrenia," *Psychopharmacology*, 214(2): 403-413, 2011.
Hostgaard-Jensen, et al., "Pharmacological characterization of a novel positive modulator at α 4 β 3 δ-containing extrasynaptic GABA A receptors," *Neuropharmacology*, 58(4): 702-711, 2010.
International Search Report and Written Opinion issued for International Application No. PCT/US2015/060627 dated Jan. 28, 2016.
Li et al., "Pathogenic plasticity of kv7.2/3 channel activity is essential for the induction of tinnitus," *Proceedings of the National Academy of Sciences of the United States of America*, 110(24): 9980-9985, Jun. 11, 2013.
Oak et al., "Voltage-gated K+ channels contributing to temporal precision at the inner hair cell-auditory afferent nerve fiber synapses in the mammalian cochlea," 37(7): 821-833, Jul. 2014.
Vardya et al., "Positive modulation of δ-subunit containing GABA A receptors in mouse neurons," *Neuropharmacology*, 63(3): 469-479, 2012.

\* cited by examiner

Drug: NR561_050 (n = 2)
Chemical Formula: $C_{17}H_{18}F_3N_3O_2$

Drug: NR561_045 (n = 2)
Chemical Formula: $C_{16}H_{18}F_5N_3O_2S$

Drug: NR561_040 (n = 4)
Chemical Formula: $C_{17}H_{18}F_3N_3O_2$

Drug: NR561_029 (n = 4)
Chemical Formula: $C_{16}H_{18}F_5N_3O_2S$

Parent Compounds

1ST Generation Class I

1ST Generation Class II

1ST Generation Class III

RL648_73

RL648_81

RL648_86

RL673_02

2nd Generation

(2-AMINO-4-(ARYLAMINO)PHENYL CARBAMATES

This is the U.S. National Stage of International Application No. PCT/US2015/060627, filed Nov. 13, 2015, which was published in English under PCT Article 21(2), which in turn claims the benefit of U.S. Provisional Application No. 62/079,430, filed Nov. 13, 2014, which is incorporated herein by reference.

ACKNOWLEDGMENT OF GOVERNMENT SUPPORT

This invention was made with government support under grant #W81XWH-14-1-0117 awarded by the ARMY/MRMC (US Army Medical Research and Materiel Command) U.S. Department of the Army. The government has certain rights in the invention.

BACKGROUND

Tinnitus is a common auditory disorder that is often the result of extreme sound exposure. An estimated 5-15% of the population experiences chronic tinnitus, with many millions of those sufferers disabled by this condition. With an even higher prevalence of chronic tinnitus in recent war veterans (tinnitus is the most prevalent service-connected disability for US veterans receiving compensation, the personal and financial costs of tinnitus have expanded dramatically. Despite the high prevalence of tinnitus, the neuronal mechanisms that mediate the initiation (induction) and the maintenance (expression) of the disorder remain poorly understood. As a result, at this time there is no generally accepted treatment, cure or preventive method for tinnitus.

Not surprisingly, in light of the significance of tinnitus as a health problem, several drug trials for tinnitus therapy are in late stage development or have reached the market (Cederroth, C. R.; Canlon, B.; Langguth, B., "Hearing loss and tinnitus—are funders and industry listening?" Nature Biotechnology 2013, 31, 972-974). There is strong evidence that K-channels play a critical role in the development of tinnitus. K-channels, by decreasing the Rm of postsynaptic membranes, reduce membrane response time and shorten the duration of EPSPs and APs. This indicates that K-channels in auditory synapses are playing a critical role in improving temporal resolution of the auditory synaptic transmission (Oak, M.-H.; Yi, E., "Voltage-gated K+ channels contributing to temporal precision at the inner hair cell-auditory afferent nerve fiber synapses in the mammalian cochlea." Arch. Pharmacal Res. 2014, 37, 821-833).

A mouse model of noise-induced tinnitus has been refined to study the mechanisms that mediate the induction of tinnitus (Li, S.; Choi, V.; Tzounopoulos, T., "Pathogenic plasticity of kv7.2/3 channel activity is essential for the induction of tinnitus." Proc. Natl. Acad. of Sci. USA 2013, 110, 9980-9985). It is the downregulation of channels Kv7.2/3 that is crucial for the induction of tinnitus. It was found that pharmacological enhancement of Kv7.2/3 with retigabine (also known as ezogabine or Potiga) prevents the development of tinnitus.

SUMMARY

Disclosed herein in one embodiment is a compound, or pharmaceutically acceptable salt thereof, having a formula I of:

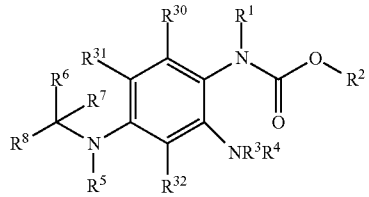

wherein $R^1$ is H or optionally-substituted alkyl;
$R^2$ is optionally-substituted alkyl;
$R^3$ and $R^4$ are each independently H or optionally-substituted alkyl;
$R^5$ is H, optionally-substituted alkyl, acyl, or alkoxycarbonyl;
$R^6$ and $R^7$ are each independently H, deuterium, optionally-substituted alkyl, or $R^6$ and $R^7$ together form a carbocycle;
$R^8$ is optionally-substituted thiazolyl, optionally-substituted thiophenyl, or substituted phenyl, provided that if $R^8$ is 4-halophenyl, then $R^2$ is substituted alkyl or branched alkyl or at least one of $R^6$ or $R^7$ is not H; and
$R^{30}$, $R^{31}$ and $R^{32}$ are each independently H, deuterium, halogen, substituted sulfanyl, or optionally-substituted alkoxy.

Disclosed herein in a further embodiment is a compound, or a pharmaceutically acceptable salt thereof, having a formula II of:

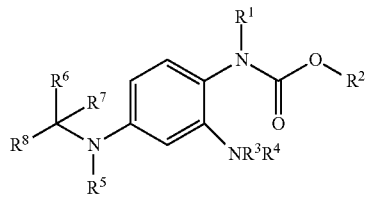

wherein $R^1$ is H or optionally-substituted alkyl;
$R^2$ is optionally-substituted alkyl;
$R^3$ and $R^4$ are each independently H or optionally-substituted alkyl;
$R^5$ is H, optionally-substituted alkyl, acyl, or alkoxycarbonyl;
$R^6$ and $R^7$ are each independently H, deuterium, optionally-substituted alkyl, or $R^6$ and $R^7$ together form a carbocycle; and
$R^8$ is optionally-substituted thiazolyl, optionally-substituted thiophenyl, or substituted phenyl, provided that if $R^8$ is 4-fluorophenyl, then $R^2$ is substituted alkyl or at least one of $R^6$ or $R^7$ is not H, and provided that if $R^8$ is substituted thiophenyl, then at least one substituent on the thiophenyl is halo-substituted sulfanyl.

Also disclosed herein is a method of treating tinnitus in a subject, comprising administering to the subject in need thereof a therapeutically effective amount of a compound disclosed herein.

Further disclosed herein is a method comprising treating a subject suffering from or susceptible to conditions that are ameliorated by Kv7.2/3 potassium channel opening, comprising administering to the subject a therapeutically effective amount of a compound disclosed herein.

Additionally disclosed herein is a method of producing an anti-epileptic, muscle relaxing, fever reducing, peripherally analgesic or anti-convulsive effect in a subject in need thereof, comprising administering to the subject a therapeutically effective amount of a compound disclosed herein.

Further disclosed herein is a method for treating a neurotransmission disorder, CNS disorder, functional bowel disorder, a neurodegenerative disease, a cognitive disorder, or a migraine in a subject, comprising administering to the subject in need thereof a therapeutically effective amount of at least compound disclosed herein.

The foregoing will become more apparent from the following detailed description, which proceeds with reference to the accompanying figures.

DETAILED DESCRIPTION

Terminology

Figure 1A:
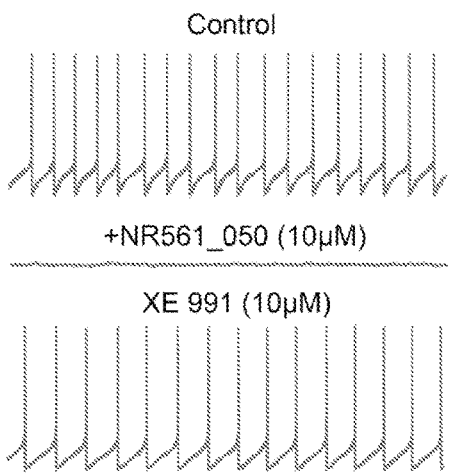
FIGS. 1A-1D shows electrophysiological traces for four compounds disclosed herein.
Figure 1B:
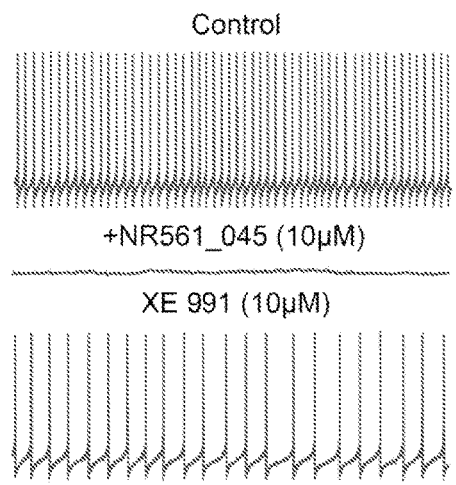
Figure 1C:
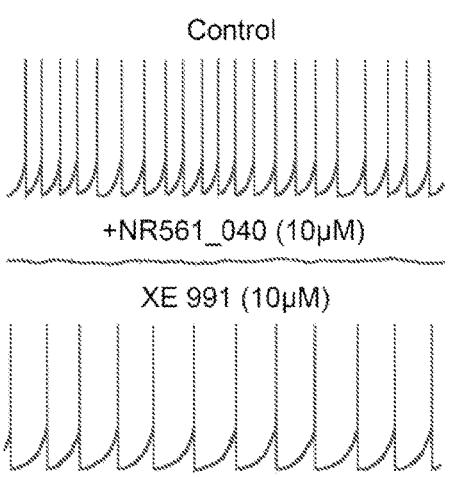
Figure 1D:
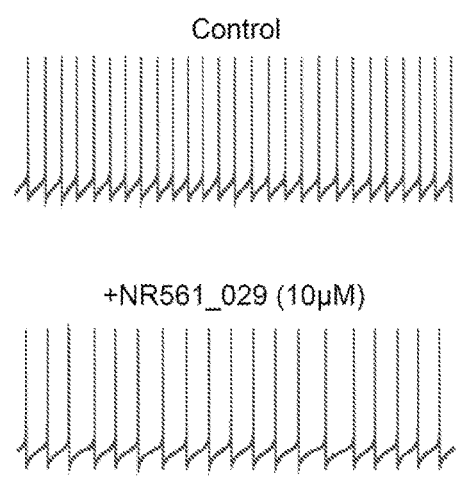
Figure 2:
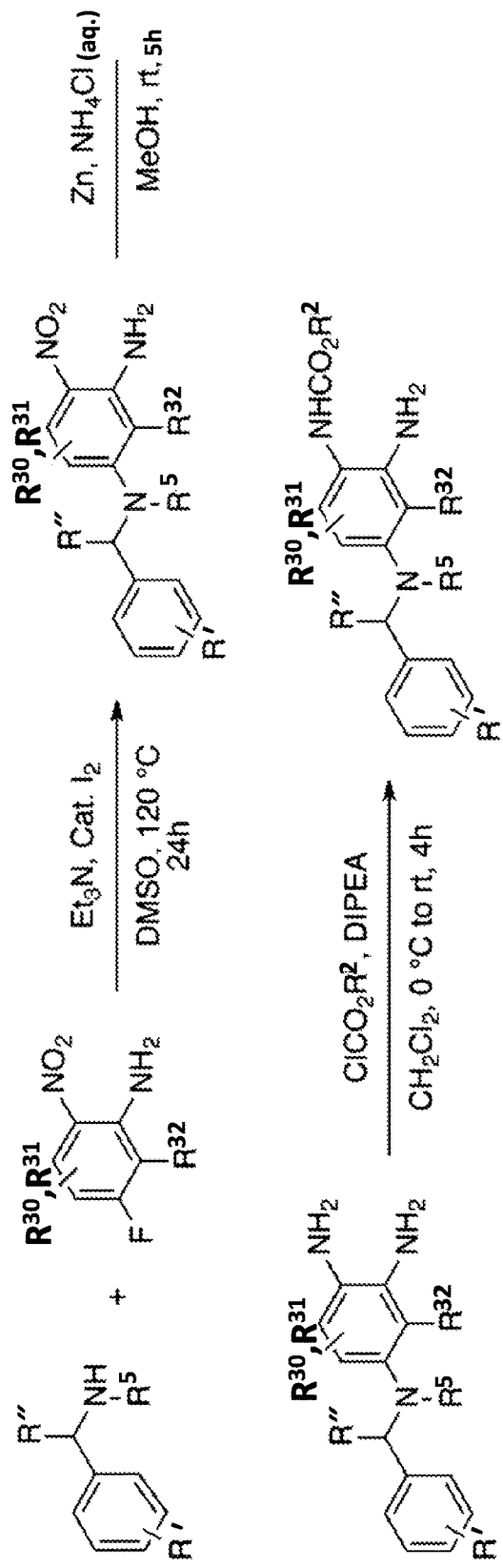
FIG. 2 is a general synthesis scheme for making compounds of formula I. R' in FIG. 2 coincides with a substituent on the $R^8$ ring in formula I, and R" in FIG. 2 coincides with $R^6$ and/or $R^7$ in formula I.
Figure 3:
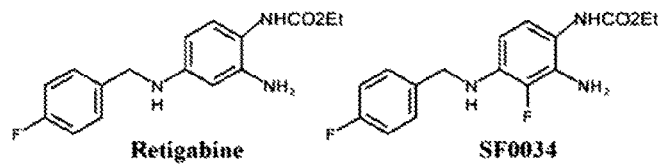
FIG. 3. Structure and classification of $1^{st}$ generation compounds. Three classes of 1st generation KCNQ channel activators were synthesized based on the position of modification of the retigabine structure. In class I, modifications were made at the phenyl ring, in class II at the arylmethylamine methylene group and in class III at the carbamate functional group of retigabine.
Figure 3:
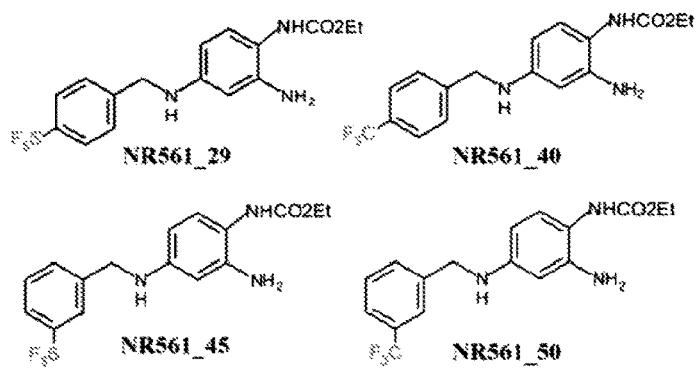
Figure 3:
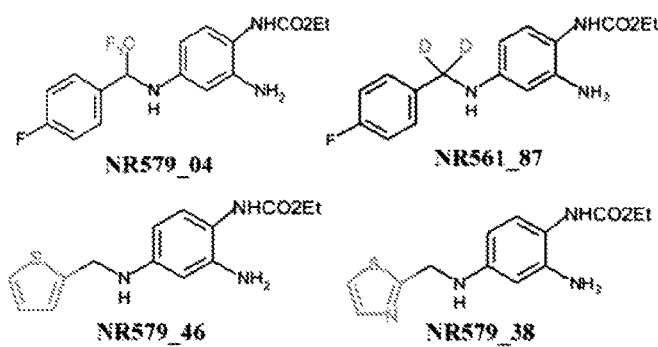
Figure 3:
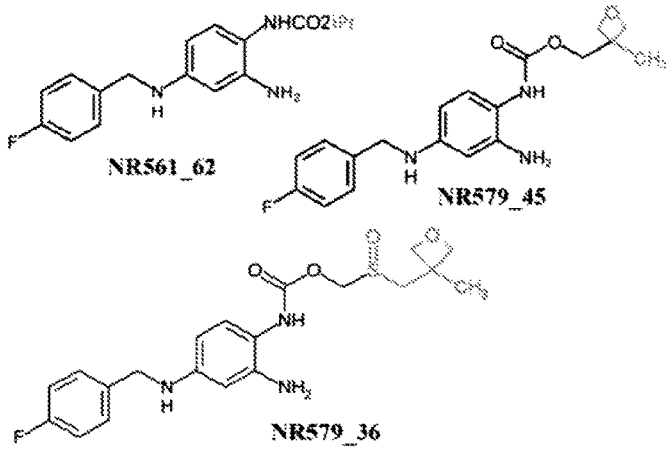
Figure 4A:
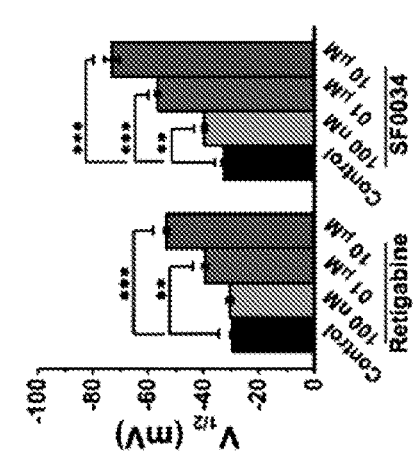
FIG. 4. Retigabine and SF0034 at KCNQ2/3 channels. SF0034 is five-times more potent than retigabine in activating KCNQ2/3 channel currents. CHO cells transiently expressing heterologous KCNQ2/3 channels were clamped at −85 mV and KCNQ2/3 currents were measured elicited by 1 s depolarization step from −105 to +15 mV in the increment of 10 mV followed by return step to −70 mV. A, C. Representative current traces of KCNQ2/3 currents at increasing membrane potentials in absence and presence of 100 nM retigabine (A) and 100 nM SF0034 (C). B, D. Representative curves of normalized G-V (conductance-voltage) relationship of KCNQ2/3 currents at control and at increasing concentration of retigabine (B) and SF0034 (D). E. Summary bar graph representing half activation ($V_{1/2}$) of KCNQ2/3 currents calculated from normalized G-V Boltzmann curves at control and at increasing concentration of retigabine and SF0034. SF0034 at 100 nM significantly shift the $V_{1/2}$ of KCNQ2/3 currents from control, whereas retigabine failed to show effect at 100 nM concentration. F. Representative curves showing half activation shift ($\Delta V_{1/2}$) by retigabine with $EC_{50}$ 3.3±0.8 µM (n=4-11, black) and SF004 with $EC_{50}$ 0.60±0.06 µM (n=5-21, red) in concentration dependent manner (100 nM-30 µM). Curves were fitted with a hill equation and $EC_{50}$ values were calculated. Error bars represent mean±SEM. p<0.01, *p<0.001.
Figure 4C:
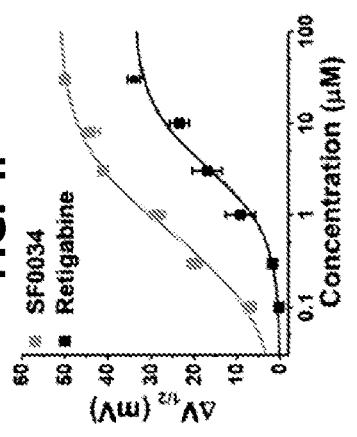
Figure 4E:
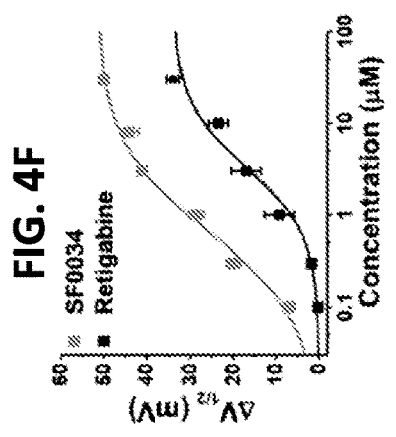
Figure 4B:
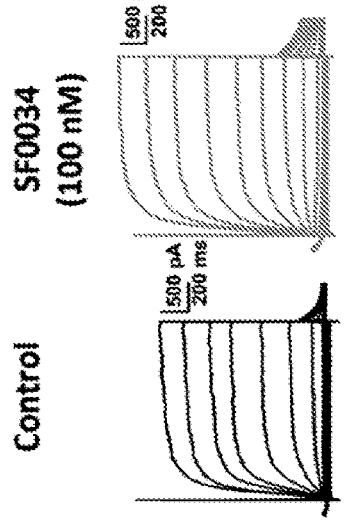
Figure 4D:
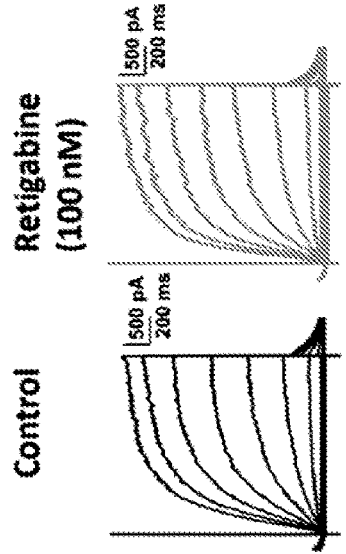
Figure 4F:
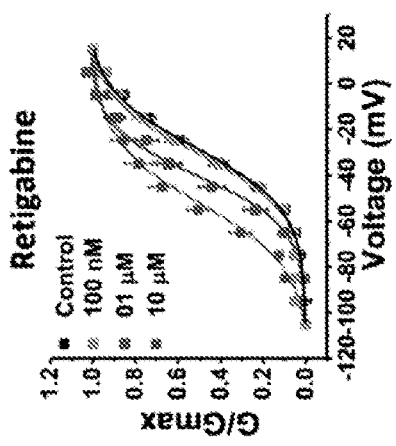
Figure 5:
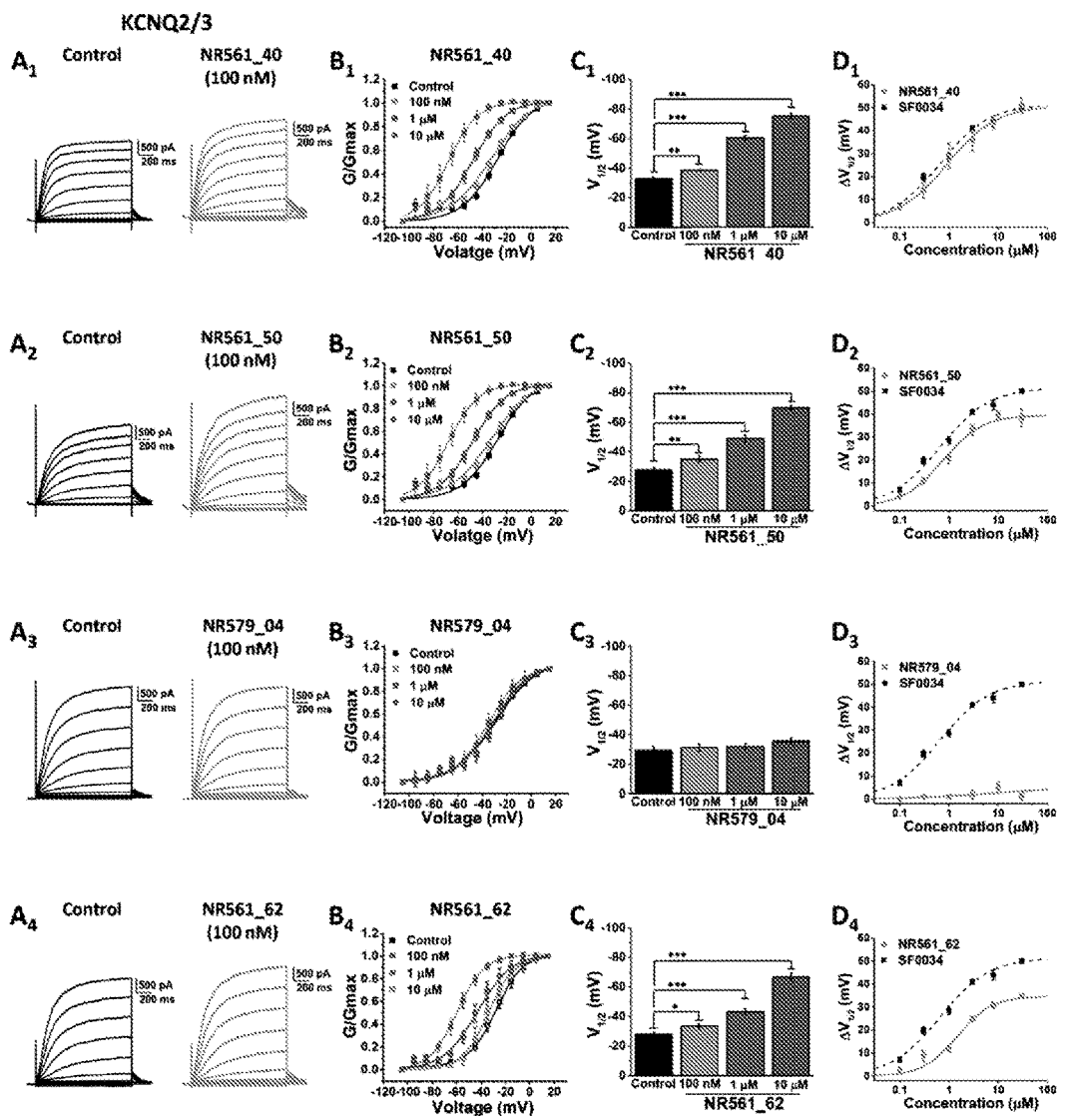
FIG. 5. First generation compounds at KCNQ2/3 channels. Substitution of triflouromethyl (—CF3) and pentafluorosulphanyl (—SF5) group at phenyl ring of retigabine significantly increased the potency in activating KCNQ2/3 currents. CHO cells transiently expressing heterologous KCNQ2/3 channels were clamped at −85 mV and KCNQ2/3 currents were measured elicited by 1 s depolarization step from −105 to +15 mV in the increment of 10 mV followed by return step to −70 mV. $A_{1-4}$. Representative current traces of KCNQ2/3 currents at increasing membrane potentials in absence and in presence of 100 nM NR561_40 ($A_1$), 100 nM NR561_50 ($A_2$), 100 nM NR579_04 ($A_3$) and 100 nM NR561_62 ($A_4$). $B_{1-4}$. Representative curves of normalized G-V relationship of KCNQ2/3 currents at control and at increasing concentration of NR561_40 ($B_1$), NR561_50 ($B_2$), NR579_04 ($B_3$) and NR561_62 ($B_3$). $C_{1-4}$. Summary bar graphs representing half activation ($V_{1/2}$) of KCNQ2/3 currents calculated from normalized G-V Boltzmann curves at control and at increasing concentration of NR561_40 ($C_1$) NR561_50, ($C_2$) NR579_04 ($C_3$) and NR561_62 ($C_4$) $D_{1-4}$. Representative curves showing half activation shift ($\Delta V_{1/2}$) by NR561_40 ($EC_{50}$ 0.91±0.08 µM, n=4-8; red) ($D_1$), NR561_50 ($EC_{50}$ 0.74±0.07 µM, n=4-9; red) ($D_2$), NR579_04 ($EC_{50}$ NA, n=4-9; Red) ($D_3$) and NR561_62 ($EC_{50}$ 1.48±0.18 µM, n=4-9; Red) ($D_4$) along with SF0034 (dotted black) in concentration dependent manner (100 nM-30 µM). NR561_40 and NR561_50 showed similar potency as of SF0034 in activating KCNQ2/3 channel currents. NR561_62 showed 2-3 times lower potency than SF0034 whereas NR579_04 did not activate KCNQ2/3 currents at all. Curves were fitted with a hill equation and EC50 values were calculated. Error bars represent mean±SEM. *p<0.05, **p<0.01.
Figure 6:
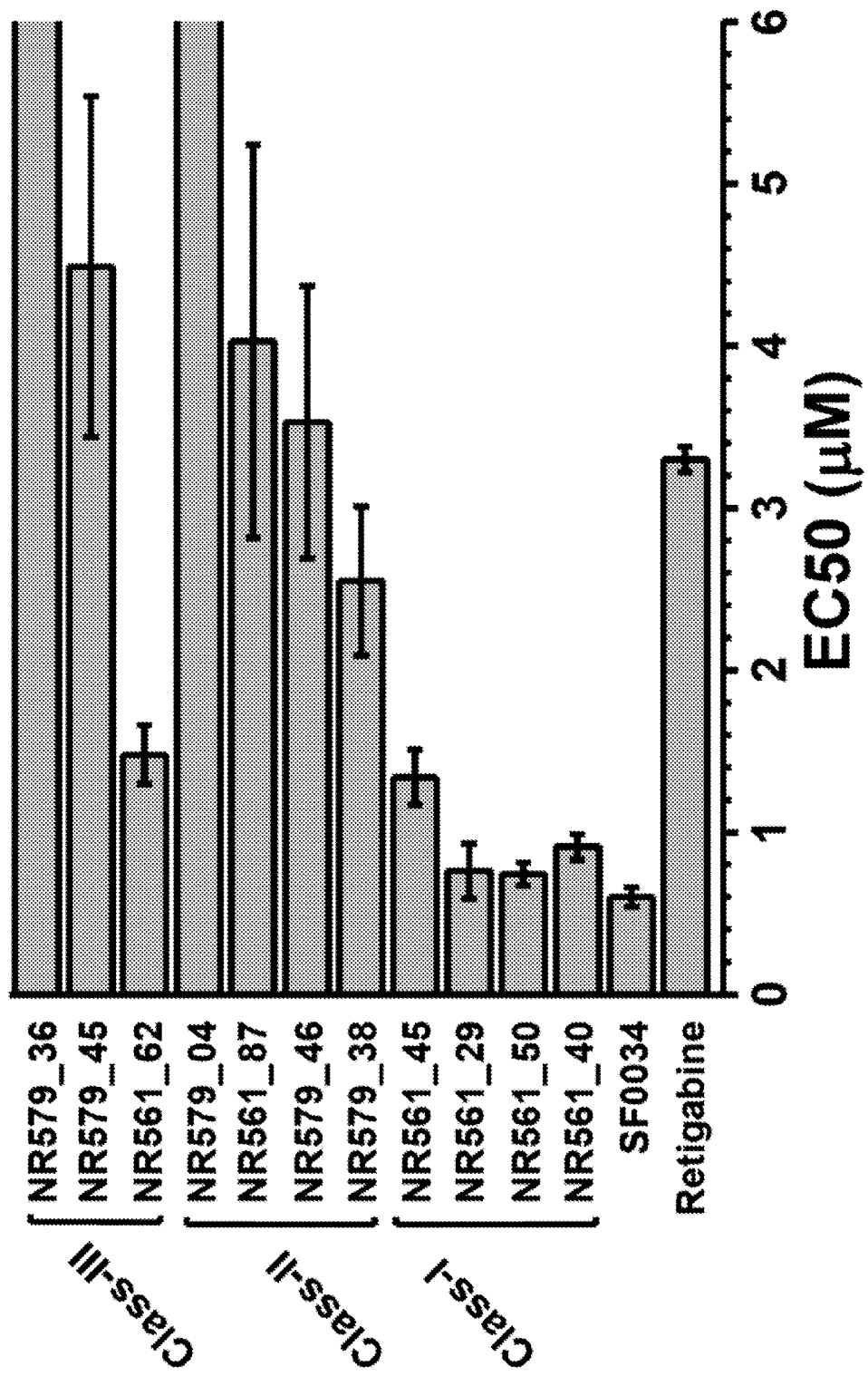
FIG. 6. Summary bar graphs representing $EC_{50}$ values of first generation compounds tested at KCNQ2/3 channels. Like SF0034, first generation class I compounds NR561_40, NR561_50 and NR561_29 showed 4-5 times more potency than retigabine in activating KCNQ2/3 channel currents.
Figure 7:
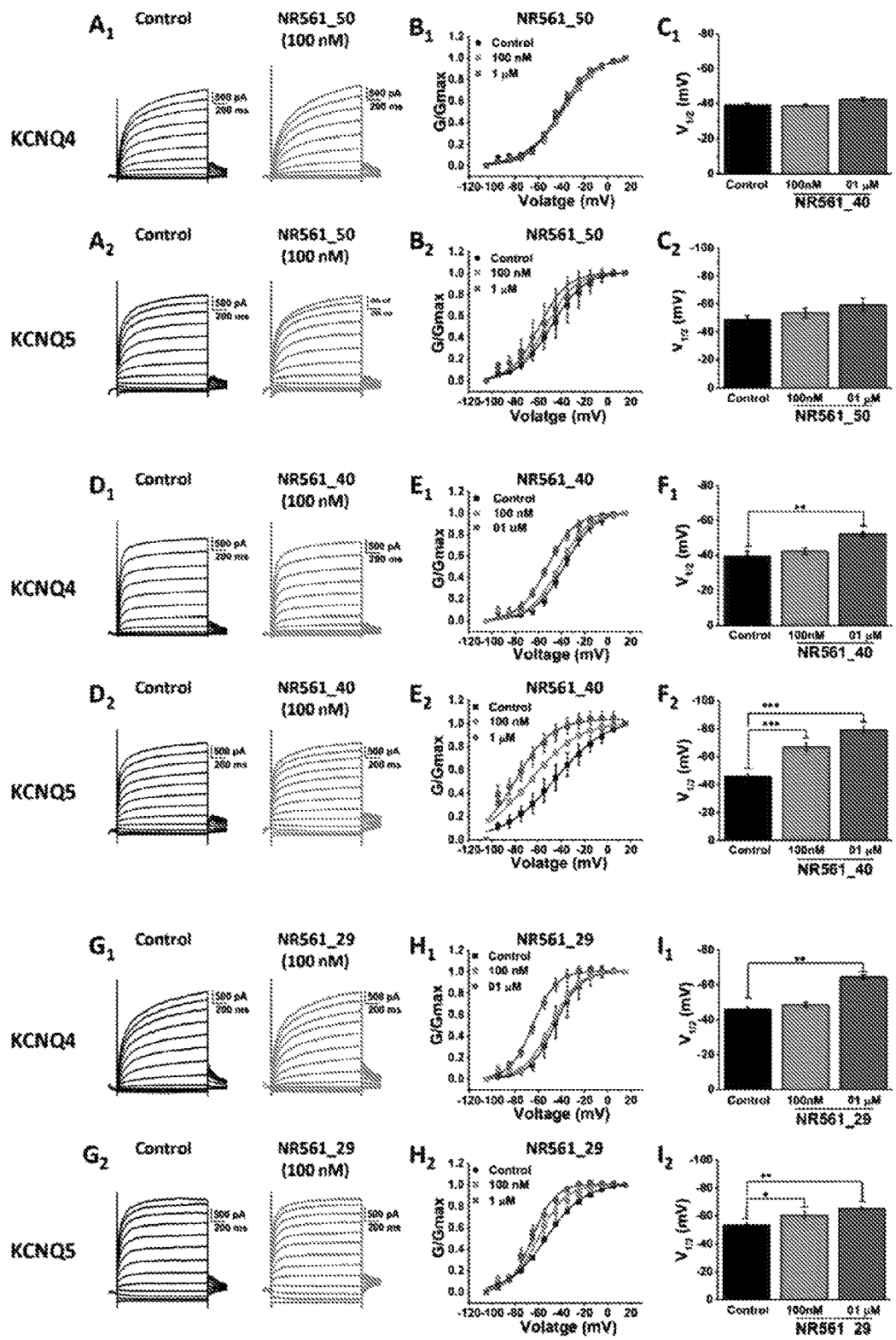
FIG. 7. NR561_50, NR561_40 and NR561_29 at KCNQ4 and KCNQ5 channels. NR561_50 does not activate KCNQ4 and KCNQ5 channel currents significantly. CHO cells transiently expressing homomeric KCNQ4 or KCNQ5 channels were clamped at −85 mV and KCNQ currents were measured elicited by 1 s depolarization step from −105 to +15 mV in the increment of 10 mV followed by return step to −70 mV. $A_{1-2}$ Representative current traces of KCNQ4 ($A_1$) and KCNQ5 ($A_2$) channel currents at increasing membrane potentials in absence and in presence of 100 nM NR561_50. $B_{1-2}$. Representative curves of normalized G-V relationship of KCNQ4 ($B_1$) and KCNQ5 ($B_2$) currents at control, 100 nM and 1 µM NR561_50. $C_{1-2}$. Summary bar graph representing half activation voltage ($V_{1/2}$) of KCNQ4 ($C_1$) and KCNQ5 ($C_2$) channel currents calculated from normalized G-V Boltzmann curves at control, 100 nM and 1 µM NR561_50. $D_{1-2}$ Representative current traces of KCNQ4 ($D_1$) and KCNQ5 ($D_2$) channel currents at increasing membrane potentials in absence and in presence of 100 nM NR561_40. $E_{1-2}$. Representative curves of normalized G-V relationship of KCNQ4 ($E_1$) and KCNQ5 ($E_2$) currents at control, 100 nM and 1 µM NR561_40. $F_{1-2}$. Summary bar graph representing half activation voltage ($V_{1/2}$) of KCNQ4 ($E_1$) and KCNQ5 ($E_2$) channel currents calculated from normalized G-V Boltzmann curves at control, 100 nM and 1 µM NR561_40. $G_{1-2}$ Representative current traces of KCNQ4 ($G_1$) and KCNQ5 ($G_2$) channel currents at increasing membrane potentials in absence and in presence of 100 nM NR561_40. $H_{1-2}$. Representative curves of normalized G-V relationship of KCNQ4 ($H_1$) and KCNQ5 ($H_2$) currents at control, 100 nM and 1 µM NR561_40. $I_{1-2}$. Summary bar graph representing half activation voltage ($V_{1/2}$) of KCNQ4 ($I_1$) and KCNQ5 ($I_2$) channel currents calculated from normalized G-V Boltzmann curves at control, 100 nM and 1 µM NR561_40. Error bars represent mean±SEM. *p<0.05, **p<0.01.
Figure 8:
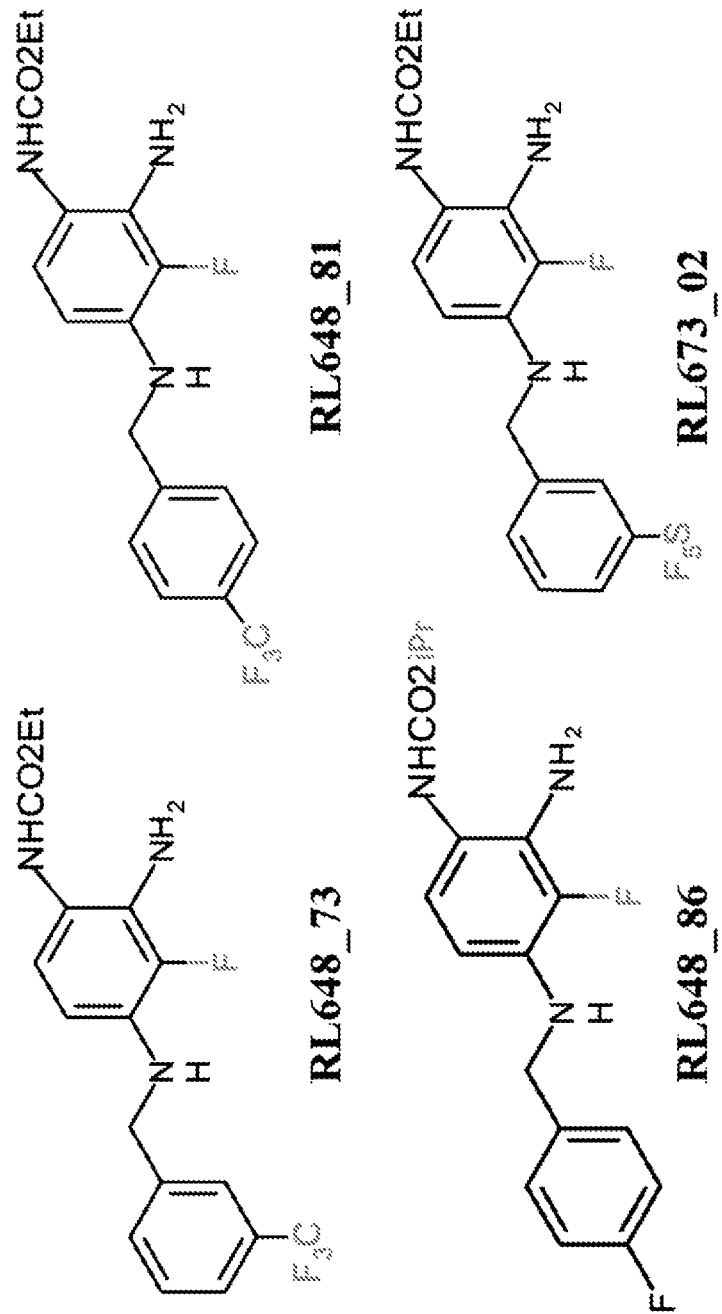
FIG. 8. Structures of $2^{nd}$ generation compounds synthesized. Like SF0034, a fluorine atom was introduced at the aniline ring of NR561_50, NR561_40, NR561_62 and NR561_45 to generate RL648_73, RL648_81, RL648_86 and RL673_02 respectively.
Figure 9:
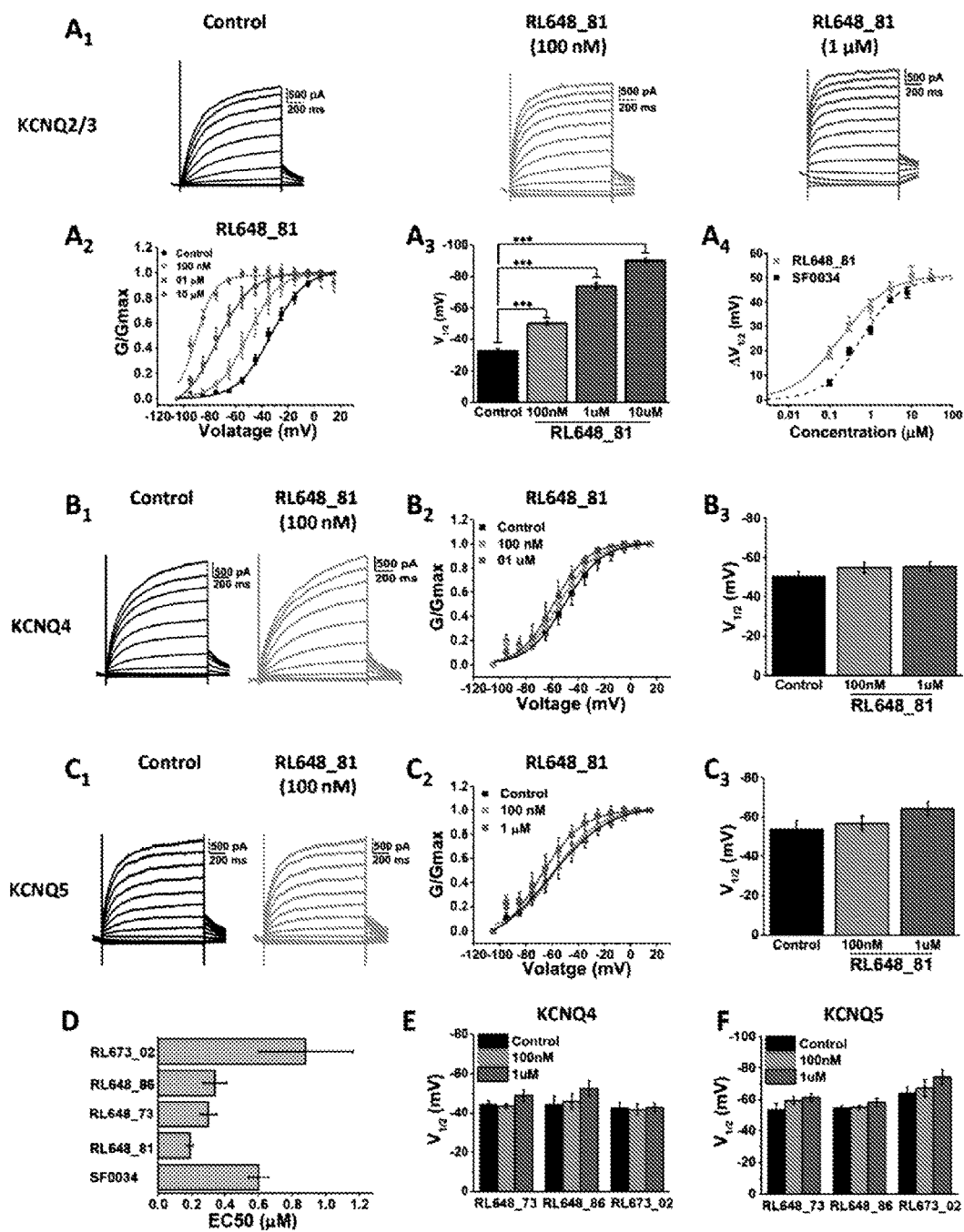
FIG. 9. Second generation compounds at heterologous KCNQ2/3 and homomeric KCNQ4 and KCNQ5 channels. RL548_81 is three times more potent than SF0034 in activating KCNQ2/3 channel currents and does not potentiate KCNQ4 and KCNQ5 channel currents significantly. CHO cells transiently expressing heterologous KCNQ2/3 and homomeric KCNQ4 and KCNQ5 channels were clamped at −85 mV and KCNQ currents were elicited by 1 s depolarization step from −105 to +15 mV in the increment of 10 mV followed by return step to −70 mV. $A_1$. Representative current traces of KCNQ2/3 currents at increasing membrane potentials in absence and presence of 100 nM or 1 µM RL648_81. $A_2$. Representative curves of normalized G-V relationship of KCNQ2/3 currents at control and at increasing concentration of RL648_81. $A_3$. Summary bar graph representing half activation ($V_{1/2}$) of KCNQ2/3 currents calculated from normalized G-V Boltzmann curves at control and at increasing concentration of RL648_81 $A_4$. Representative curves showing half activation voltage shift (ΔV½) by RL648_81 ($EC_{50}$ 0.19±0.02 µM, n=4-11; red) and SF0034 ($EC_{50}$ 0.60±0.06 µM, n=5-21; black) in a concentration dependent manner (100 nM-30 µM). Curves were fitted with a hill equation and $EC_{50}$ values were calculated. $B_1$. Representative current traces of KCNQ4 currents at increasing membrane potentials in absence and in presence of 100 nM RL648_81. $B_2$. Representative curves of normalized G-V relationship of KCNQ4 currents at control, 100 nM and 1 µM NR648_81. $B_3$. Summary bar graph representing half activation voltage ($V_{1/2}$) of KCNQ4 currents calculated from normalized G-V relationship curves at control, 100 nM and 1 µM RL648_81. $C_1$. Representative current traces of KCNQ5 currents at increasing membrane potentials absence and presence of 100 nM RL648_81. $C_2$. Representative curves of normalized G-V relationship of KCNQ5 currents at control, 100 nM and 1 µM NR648_81. $C_3$. Summary bar graph representing half activation voltage ($V_{1/2}$) of KCNQ5 currents calculated from normalized G-V Boltzmann curves at control, 100 nM and 1 µM RL648_81. D. Summary bar graphs representing $EC_{50}$ values of second generation compounds tested at KCNQ2/3 channels in comparison with SF0034. RL648_73 and RL_86 showed 2 times more potency than SF0034 in activating KCNQ2/3 channels. E. Summary bar graph representing half activation ($V_{1/2}$) of KCNQ4 currents calculated from normalized G-V Boltzmann curves in presence of 100 nM and 1 µM of RL648_73, RL648_86 and RL673_02. F. Summary bar graph representing half activation voltage (V/2) of KCNQ5 currents calculated from normalized G-V Boltzmann curves in presence of 100 nM and 1 µM of RL648_73, RL648_86 and RL673_02. Error bars represent mean±SEM. ***$p<0.001$.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, hydrogen, optionally substituted alkyl, optionally substituted cycloalkyl, optionally substituted heterocycloalkyl, optionally substituted aryl, or optionally substituted heteroaryl. "Lower acyl" groups are those that contain one to six carbon atoms.

"Administration" as used herein is inclusive of administration by another person to the subject or self-administration by the subject.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, heterocycloalkyl, heteroaryl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

The term "aminoalkyl" refers to alkyl groups as defined above where at least one hydrogen atom is replaced with an amino group (e.g., —$CH_2$—$NH_2$).

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Aryloxy" or "heteroaryloxy" refers to a group of the formula —OAr, wherein Ar is an aryl group or a heteroaryl group, respectively.

"Carbocycle" refers to a saturated or unsaturated cyclic radical of 3 to 8 ring atoms in which each of the ring atoms are carbon. Such carbocyclic groups may be optionally substituted independently with one, two or three substituents selected from alkyl, heteroalkyl, haloalkyl, cycloalkyl, cycloalkylalkyl, aliphatic, heteroaliphatic, aryl, aralkyl, heteroaryl, heteroaralkyl, halo, cyano, acyl, acylamino, amino, monosubstituted amino, disubstituted amino, —COOR (where R is hydrogen or alkyl), —XR (where X is O or $S(O)_n$, where n is an integer from 0 to 2, and R is hydrogen, alkyl, haloalkyl, cycloalkyl, aralkyl, aryl, heteroaryl or heteroaralkyl), or —C(O)N(R')R" (where $R^1$ and R" are independently selected from hydrogen or alkyl). Representative examples include, but are not limited to, cyclopentyl, cyclohexyl, cycloheptyl, cycloheptenyl, or cycloheptyl-2, 3, or 4-one, and the like.

The term "carboxylate" or "carboxyl" refers to the group —$COO^-$ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

"Heterocyclic" refers to a closed-ring compound, or radical thereof as a substituent bonded to another group, particularly other organic groups, where at least one atom in the ring structure is other than carbon, and typically is oxygen, sulfur and/or nitrogen.

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. Unless otherwise defined optionally substituted N-heterocyclics includes pyridinium salts and the N-oxide form of suitable ring nitrogens.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

"Substituted sulfanyl" refers to the group —SR, wherein the number of R groups satisfies the oxidation state of S and R may be, for example, halo, optionally-substituted alkyl, optionally-substituted aryl, optionally-substituted carbocyclic, or optionally-substituted heterocyclic.

"Sulfanyl" refers to —SH.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as diabetes. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocyclyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Compounds

The downregulation of channels Kv7.2/3 is crucial for the induction of tinnitus. This significant role of Kv7 channels makes them promising targets for the development of therapeutic approaches for preventing the induction of tinnitus. However, a more specific channel activator than retigabine is desirable, and an ideal therapeutic candidate also needs to reduce side effects common with retigabine. Such an advancement will change the standard of care for tinnitus patients, as most current approaches focus on the management of tinnitus after it becomes a life-long disorder. Preventing the development of chronic tinnitus with transient, well-timed therapies will reduce the deficiencies of systemic medications as well as the health care costs associated with the long-term medical care of tinnitus patients.

Disclosed herein are (2-amino-4-(arylamino)phenyl)carbamates that activate Kv7.2/3 potassium channel activity. In certain embodiments, the carbamates may selectively activate Kv7.2/3 potassium channel activity. "Selectively activate" means that Kv7 potassium channels other than Kv7.2/3 are not activated, or are only minimally activated relative to the Kv7.2/3 potassium channel activation.

In particular, disclosed herein are compounds, or pharmaceutically acceptable salts thereof, having a formula I of:

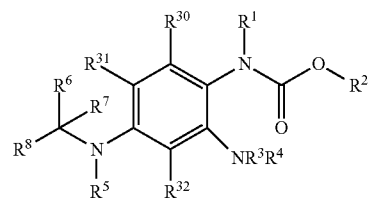

wherein $R^1$ is H or optionally-substituted alkyl;
$R^2$ is optionally-substituted alkyl;
$R^3$ and $R^4$ are each independently H or optionally-substituted alkyl;
$R^5$ is H, optionally-substituted alkyl, acyl, or alkoxycarbonyl;
$R^6$ and $R^7$ are each independently H, deuterium, optionally-substituted alkyl, or $R^6$ and $R^7$ together form a carbocycle;
$R^8$ is optionally-substituted thiazolyl, optionally-substituted thiophenyl, or substituted phenyl, provided that if $R^8$ is 4-halophenyl, then $R^2$ is substituted alkyl or branched alkyl or at least one of $R^6$ or $R^7$ is not H; and
$R^{30}$, $R^{31}$ and $R^{32}$ are each independently H, deuterium, halogen, substituted sulfanyl, or optionally-substituted alkoxy.

In certain embodiments, disclosed herein are compounds, or pharmaceutically acceptable salts thereof, having a formula II of:

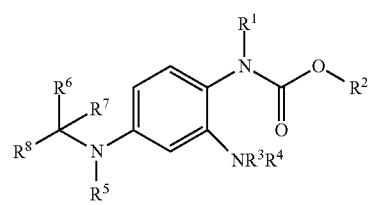

wherein $R^1$ is H or optionally-substituted alkyl;
$R^2$ is optionally-substituted alkyl;
$R^3$ and $R^4$ are each independently H or optionally-substituted alkyl;
$R^5$ is H, optionally-substituted alkyl, acyl, or alkoxycarbonyl;
$R^6$ and $R^7$ are each independently H, deuterium, optionally-substituted alkyl, or $R^6$ and $R^7$ together form a carbocycle; and
$R^8$ is optionally-substituted thiazolyl, optionally-substituted thiophenyl, or substituted phenyl, provided that if $R^8$ is 4-fluorophenyl, then $R^2$ is substituted alkyl or at least one of $R^6$ or $R^7$ is not H.

In certain embodiments of formula I or II, $R^8$ is substituted thiophenyl wherein at least one substituent is halo-substituted sulfanyl.

In certain embodiments of formula I or II, $R^1$ is H. In certain embodiments of formula I or II, $R^1$ is —$C(R^{26})_3$, wherein each $R^{26}$ is independently H, alkyl, optionally-substituted cycloalkyl, optionally-substituted aryl, or optionally-substituted heterocyclic.

In certain embodiments of formula I or II, $R^2$ is alkyl, particularly $C_1$-$C_6$ alkyl, for example, ethyl or isopropyl. In certain embodiments of formula I or II, $R^2$ is carbocyclic-substituted alkyl or heterocyclic-substituted alkyl. In certain embodiments of formula I or II, $R^2$ is —$C(R^{26})_3$, wherein each $R^{26}$ is independently H, alkyl, optionally-substituted cycloalkyl, optionally-substituted aryl, or optionally-substituted heterocyclic. In certain embodiments of formula I or II, $R^2$ is branched alkyl, particularly $C_1$-$C_6$ branched alkyl such as isopropyl, iso-butyl, or sec-butyl.

In certain embodiments of formula I or II, $R^3$ and $R^4$ are each H. In certain embodiments of formula I or II, $R^3$ and $R^4$ are each independently —$C(R^{26})_3$, wherein each $R^{26}$ is independently H, alkyl, optionally-substituted cycloalkyl, optionally-substituted aryl, or optionally-substituted heterocyclic.

In certain embodiments of formula I or II, $R^5$ is H. In certain embodiments of formula I or II, $R^5$ is —$C(R^{26})_3$, wherein each $R^{26}$ is independently H, alkyl, optionally-substituted cycloalkyl, optionally-substituted aryl, or optionally-substituted heterocyclic.

In certain embodiments of formula I or II, $R^6$ and $R^7$ are both H. In certain embodiments of formula I or II, $R^6$ and $R^7$ are both deuterium. In certain embodiments of formula I or II, $R^6$ and $R^7$ together form a cycloalkyl, particularly a $C_3$-cycloalkyl. In certain embodiments of formula I or II, at least one of $R^6$ or $R^7$ is a substituted alkyl, particularly haloalkyl, and most particularly $CF_3$.

In certain embodiments of formula I or II, $R^8$ is selected from:

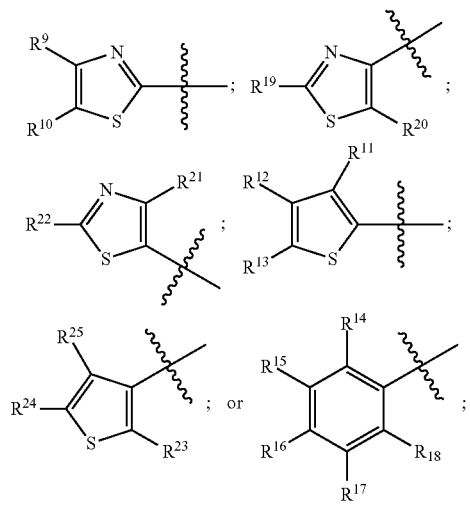

wherein $R^9$-$R^{25}$ are each independently H, halogen, optionally-substituted sulfanyl, or optionally-substituted alkyl.

In certain embodiments of formula I or II, $R^8$ is:

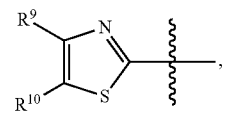

wherein at least one of $R^9$ or $R^{10}$ is halogen, particularly F. In certain embodiments, $R^9$ is halogen and $R^{10}$ is H. In certain embodiments, $R^9$ is H and $R^{10}$ is F.

In certain embodiments of formula I or II, $R^8$ is:

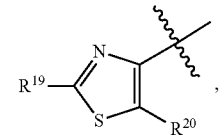

wherein at least one of $R^{19}$ or $R^{20}$ is halogen, particularly F.

In certain embodiments of formula I or II, $R^8$ is:

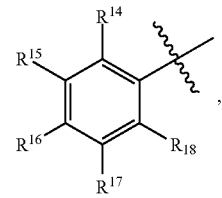

wherein at least one of $R^{14}$-$R^{18}$ is substituted sulfanyl, particularly —$SF_5$, or haloalkyl, particularly —$CF_3$; or wherein $R^{16}$ is F. In certain embodiments, $R^{16}$ is halo-substituted sulfanyl (particularly —$SF_5$) or haloalkyl (particularly —$CF_3$). In certain embodiments, $R^{17}$ is halo-substituted sulfanyl (particularly —$SF_5$) or haloalkyl (particularly —$CF_3$). In certain embodiments, $R^{15}$ is halo-substituted sulfanyl (particularly —$SF_5$) or haloalkyl (particularly —$CF_3$).

In certain embodiments of formula I or II, $R^8$ is:

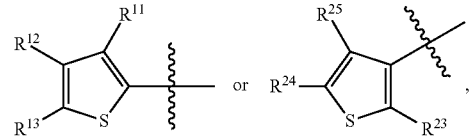

wherein at least one of $R^{11}$-$R^{13}$ or $R^{23}$-$R^{25}$ is substituted sulfanyl, particularly —$SF_5$.

In certain embodiments of Formula I, at least one of $R^{30}$, $R^{31}$ and $R^{32}$ is deuterium, halogen, substituted sulfanyl (e.g., halogen-substituted sulfanyl such as —$SF_5$), or optionally-substituted alkoxy (e.g., halogen-substituted alkoxy such as —$OCF_3$ or —$OCHF_2$). In certain embodiments of Formula I, at least one of $R^{30}$, $R^{31}$ and $R^{32}$ is halogen, particularly F. In certain embodiments, $R^{32}$ is deuterium, halogen, substituted sulfanyl (e.g., halogen-substituted sulfanyl such as —$SF_5$), or optionally-substituted alkoxy (e.g., halogen-substituted alkoxy such as —$OCF_3$ or —$OCHF_2$). In certain embodiments, $R^{32}$ is halogen, particularly F. In certain embodiments, $R^{32}$ is halogen, particularly F, and $R^{30}$ and $R^{31}$ are each H.

In certain embodiments of Formula I, $R^1$ is H, $R^2$ is alkyl, particularly $C_1$-$C_6$ alkyl, for example, ethyl or isopropyl, $R^3$ and $R^4$ are each H, $R^5$ is H, $R^6$ and $R^7$ are each H, $R^8$ is:

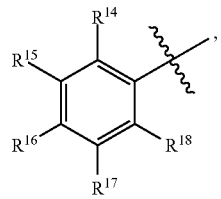

wherein at least one of $R^{14}$-$R^{18}$ is substituted sulfanyl (particularly halogenated sulfanyl such as —$SF_5$), haloalkyl (particularly —$CF_3$), or halogen, $R^{30}$ and $R^{31}$ are each H, and $R^{32}$ is halogen, particularly F. In certain embodiments of Formula I, if $R^{16}$ is halogen, then $R^2$ is branched alkyl or substituted alkyl. In certain embodiments of Formula I, $R^{16}$ is halogenated sulfanyl (particularly —$SF_5$) or haloalkyl (particularly —$CF_3$). In certain embodiments of Formula I, $R^{17}$ is halogenated sulfanyl (particularly —$SF_5$) or haloalkyl (particularly —$CF_3$). In certain embodiments of Formula I, $R^{15}$ is halogenated sulfanyl (particularly —$SF_5$) or haloalkyl (particularly —$CF_3$). In certain embodiments of Formula I or II, the haloalkyl may be halo($C_1$-$C_6$)alkyl such as iodomethyl, bromomethyl, chloromethyl, fluoromethyl, trifluoromethyl, 2-chloroethyl, 2-fluoroethyl, 2,2,2-trifluoroethyl, or pentafluoroethyl.

Illustrative compounds include:

Compound 1

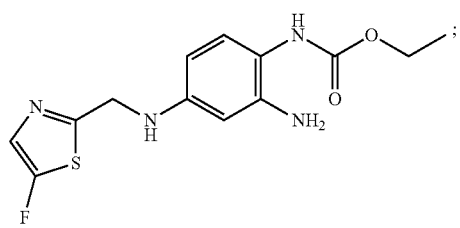

Compound 2

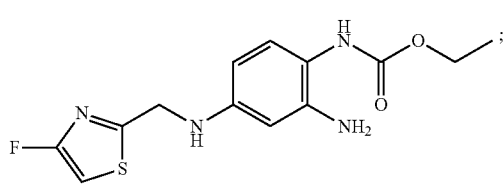

Compound 3

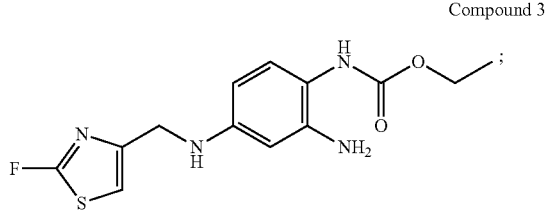

-continued

Compound 4

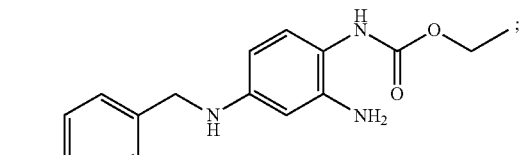

(NR561_029)

Compound 5

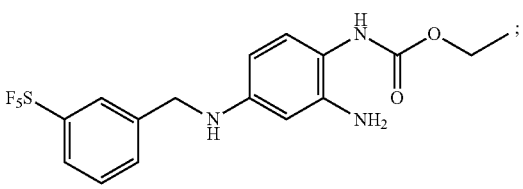

(NR561_045)

Compound 6

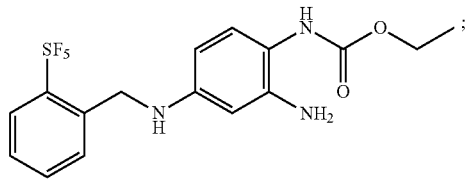

Compound 7

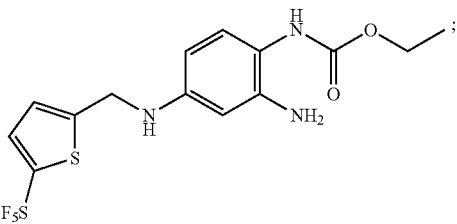

Compound 8

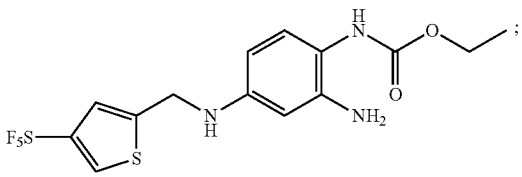

Compound 9

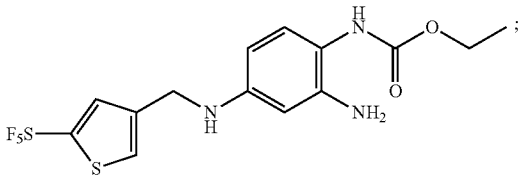

Compound 10

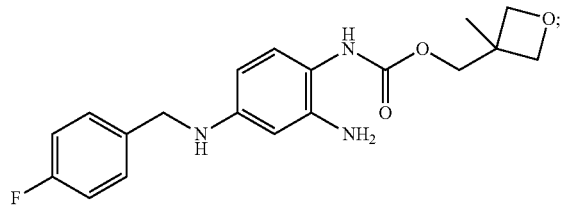

-continued

Compound 11
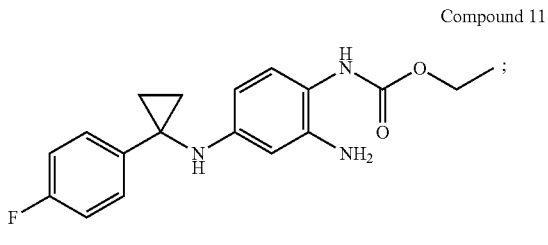

Compound 12
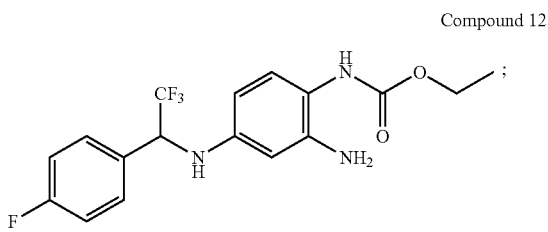

Compound 13
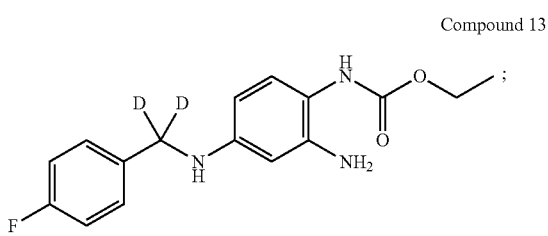

Compound 14
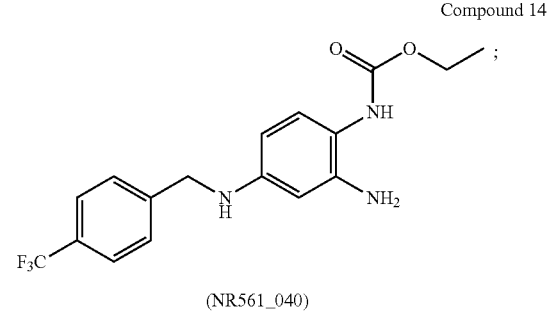
(NR561_040)

Compound 15
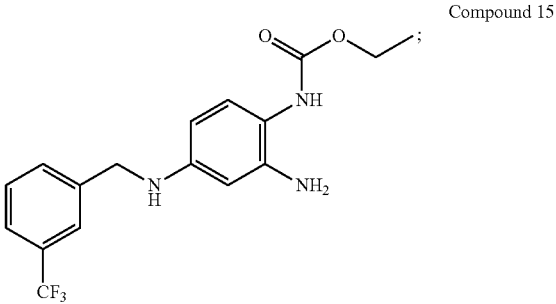
(NR561_050)

Compound RL648_86
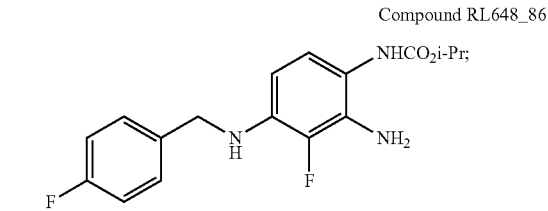

-continued

Compound RL648_73
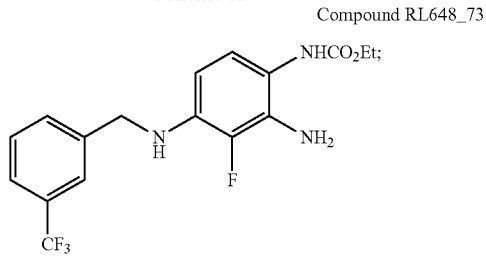

Compound RL648_81
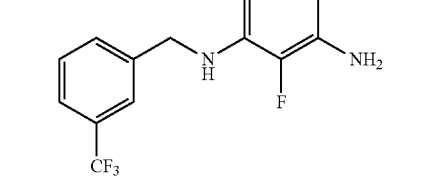

Compound RL673_02
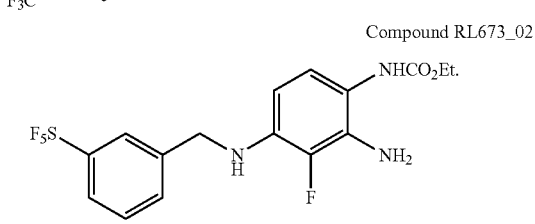

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The presently disclosed compounds can have at least one asymmetric center or geometric center, cis-trans center (C=C, C=N). All chiral, diasteromeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}F$, etc The initial compound design focused on altering three different sites on retigabine: first, the benzylamine functionality in zone 1 which targets the crucial tryptophan residue and second, the tri-aminated arene in zone 2 where substituents $R^2$ could be used to modify the basicity and electronic properties, and third, the carbamate functionality in zone 3 (see below) which likely sits in a hydrophobic pocket in the active site but may also have a hydrogen-bonding interaction with T271. The fluorophenyl functionality allows for the incorporation of several different aromatic and heteroaromatic structures with varying degrees of fluorination. The zone 3 site of alteration allows for the use of methodology to introduce several highly functionalized carbamates including those derived from the bis-oxetane sulfoxide, MMS-350, and 3-methyl-3-oxetanemethanol.

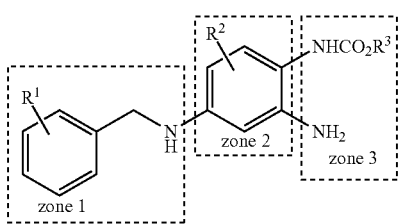

Structure of Retigabine ($R^1$=p-F, $R^2$=H, $R^3$=$CH_2CH_3$) and Regions of Modification It was envisioned that trifluoromethyl- (1-5 and 1-6) and pentafluorothiophenyl analogues (1-7 and 1-8), as well as thiophene (1-11) and thiazole analogues (1-12) would allow us to probe the structure-activity relationship of retigabine. A thorough analysis of the fluorinated benzene derivatives might reveal an electronic or steric requirement in the active site binding region of retigabine and heteroaromatic functionality could allow for additional hydrogen-bonding interactions. Additionally, alteration of the benzylic position (1-9 and 1-10) would allow for manipulation of the adjacent nitrogen atom by decreasing its basicity via inductive withdrawal or steric blocking. The first $pK_a$ of retigabine as the free base has been calculated to be 13.1 at the N-2 position, a primary site of glucuronidation. Decreasing the basicity of the secondary aniline could decrease clearance of the compound.

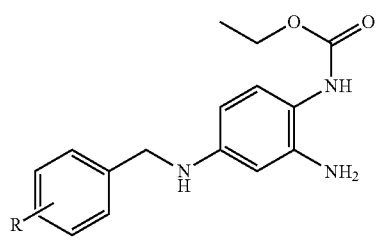

R = 4-$SF_5$ (1-5)
= 3-$SF_5$ (1-6)
= 4-$CF_3$ (1-7)
= 3-$CF_3$ (1-8)

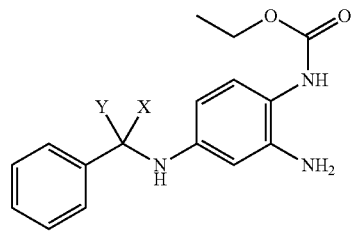

X, Y = D (1-9)
X = $CF_3$, Y = H (1-10)

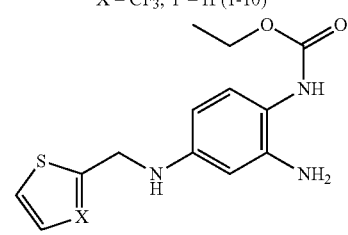

X = C (1-11)
X = N (1-12)

Examples of Fluorinated and Heterocyclic Retigabine Analogues

Alteration of zone 3 had a more focused set of objectives. Of particular interest to us were the isopropyl, MMS-350, and 3-methyloxetanemethanol derived carbamates. The isopropyl carbamate would function to probe the steric requirements around the core diamine. MMS-350 (1-13) has gained attention as a method of combating radiation exposure and as an additive to increase the aqueous solubility of small organic molecules. More recently, its ability to enhance the solubility of bioactive molecules through covalent attachment has been demonstrated. The covalently modified compounds showed increased solubility and membrane permeability. Retigabine itself is very insoluble in aqueous solution (calculated to be 45 mg/L) with the hydrochloride salt being only sparingly soluble as well. Given the hydrochloride salt's instability towards long-term storage, it was envisioned that a covalently modified MMS-350 derivative of retigabine (1-14) could impart aqueous solubility without negatively impacting stability (see figure below). In the same vein, covalently linking 3-oxetanemethanol (1-15) could improve aqueous solubility and has the potential for additional hydrogen bond interactions.

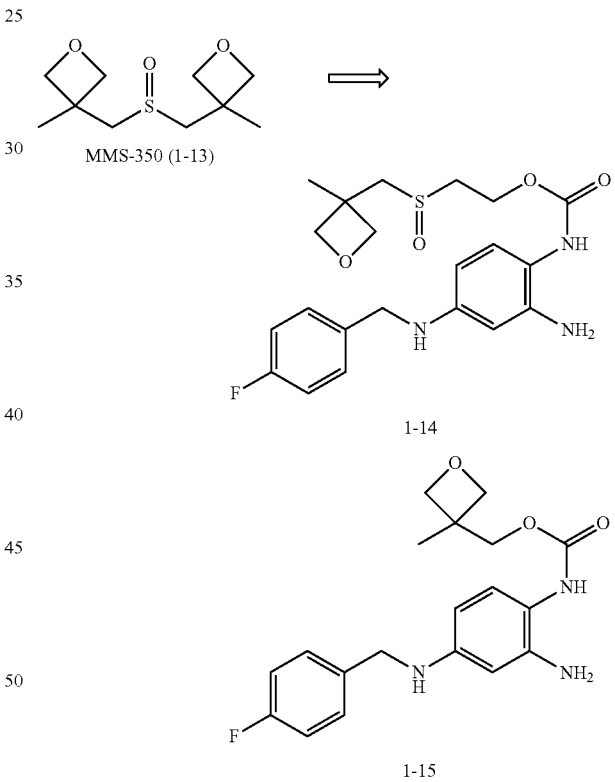

Covalently modified MMS-350 and 3-Methyl-3-oxetanemethanol Retigabine Analogues

With the first round of analogues determined, initial synthetic efforts focused on synthesizing the fluorinated benzene derivatives of Retigabine. Polycarbamoylation was anticipated to be a problem, therefore, protection of the secondary amine with CbzCl was seen as a preferable approach to access the desired compounds. Condensation under Dean-Stark conditions in toluene and subsequent reduction of the intermediate imines with sodium borohydride furnished diamines 1-16 to 1-19 in good yield (Scheme 1).

Scheme 1. Reductive Amination of 2-Nitro-p-phenylenediamine with Fluorinated Benzaldehydes

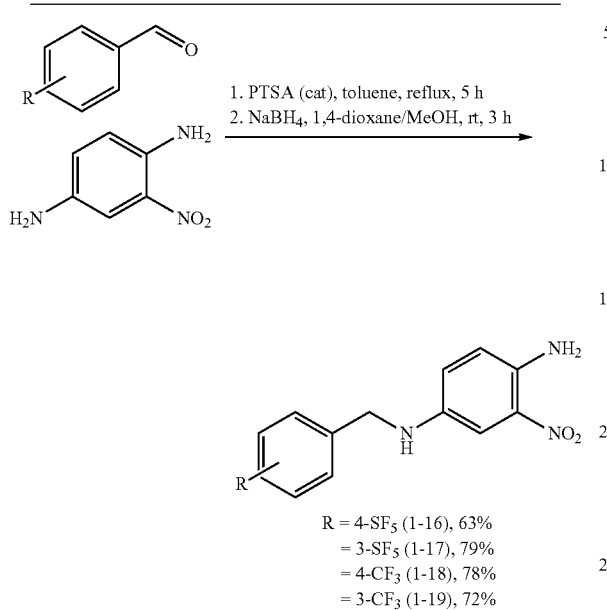

R = 4-SF$_5$ (1-16), 63%
= 3-SF$_5$ (1-17), 79%
= 4-CF$_3$ (1-18), 78%
= 3-CF$_3$ (1-19), 72%

Protection of the secondary amine with CbzCl and DIPEA proceeds readily at room temperature (Scheme 2). Isolation of Cbz-protected amine 1-20 proved difficult, thus the crude Cbz protected amines were treated with ethyl chloroformate and DIPEA in 1,4-dioxane to give 1-24 to 1-27. Several equivalents of ethyl chloroformate (2-5 eq.) and DIPEA (2-5 eq.), elevated temperatures, and extended reaction times were needed to achieve synthetically useful yields.

Scheme 2. Protection and Carbamoylation of Reductive Amination Products

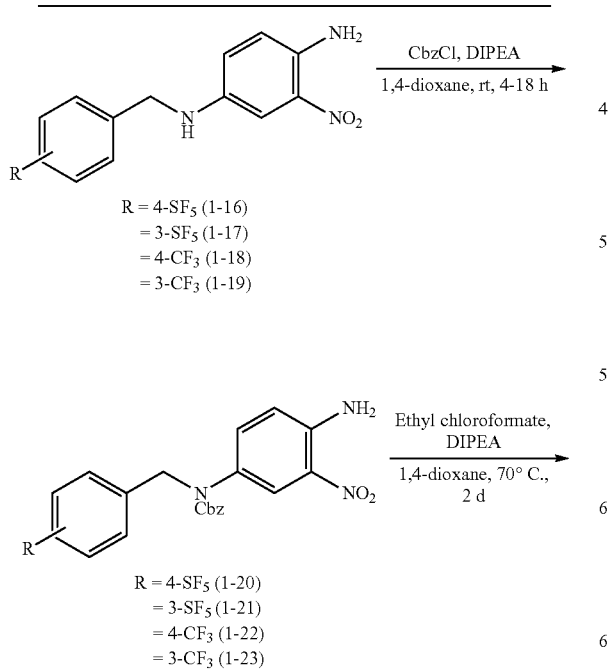

R = 4-SF$_5$ (1-20)
= 3-SF$_5$ (1-21)
= 4-CF$_3$ (1-22)
= 3-CF$_3$ (1-23)

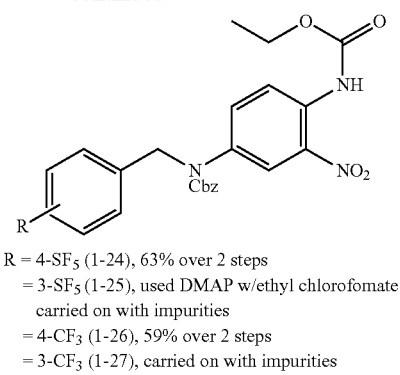

R = 4-SF$_5$ (1-24), 63% over 2 steps
= 3-SF$_5$ (1-25), used DMAP w/ethyl chlorofomate carried on with impurities
= 4-CF$_3$ (1-26), 59% over 2 steps
= 3-CF$_3$ (1-27), carried on with impurities Hydrogenolysis of the Cbz group and reduction of the nitro group were accomplished using Pd/C and H$_2$ to give 1-5 to 1-8 in good yields (Scheme 3).

Scheme 3. Reduction and Cleavage of Cbz Protecting Group Using Catalytic Hydrogenation

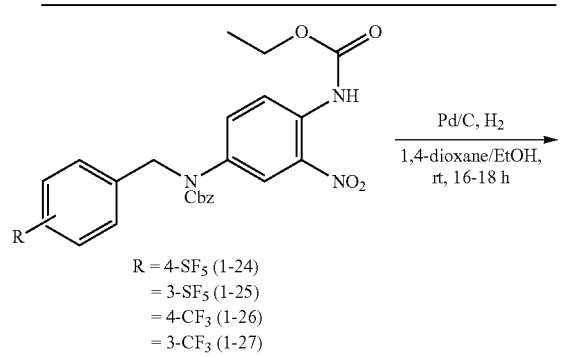

R = 4-SF$_5$ (1-24)
= 3-SF$_5$ (1-25)
= 4-CF$_3$ (1-26)
= 3-CF$_3$ (1-27)

R = 4-SF$_5$ (1-5), 54%
= 3-SF$_5$ (1-6), 13% over 3 steps
= 4-CF$_3$ (1-7), 72%
= 3-CF$_3$ (1-8), 24% over 3 steps Reductive amination of 2,2,2-trifluoroacetophenone and 2-nitro-p-phenylenediamine under Dean-Stark conditions in toluene gave only low yields (ca. 12%) of 1-29 (Scheme 4). Comparable yields were obtained utilizing a procedure promoted by AlMe$_3$/BH$_3$.SMe$_2$ and no product was observed using molecular sieves at room temperature. Attempted protection of the secondary aromatic amine resulted in the incorrect regioisomer 1-30 in 75% yield.

Scheme 4. Reductive Amination and Protection Affording Regioisomer 1-30

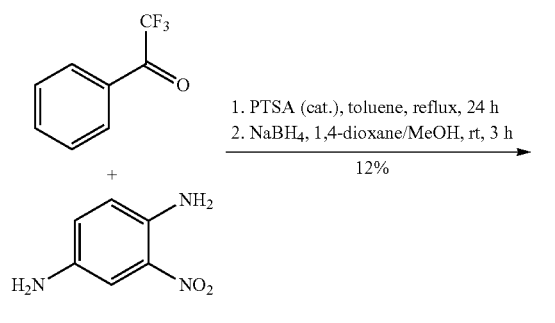

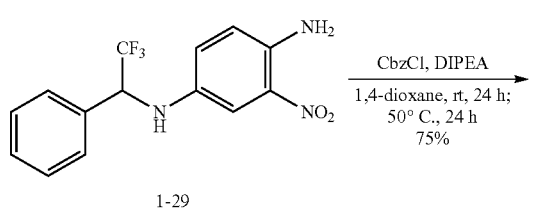

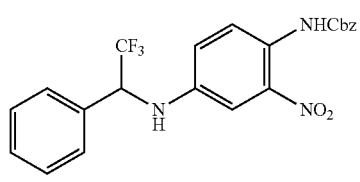

Thus, treatment of 1-29 with ethyl chloroformate at room temperature for 24 h and then at 50° C. for a further 24 h gave ethyl carbamate 1-31 in 73% yield (Scheme 5). Subsequent reduction with Pd/C and H₂ proceeded in excellent yield to give 1-10.

Scheme 5. Carbamoylation and Catalytic Hydrogenation of 1-29

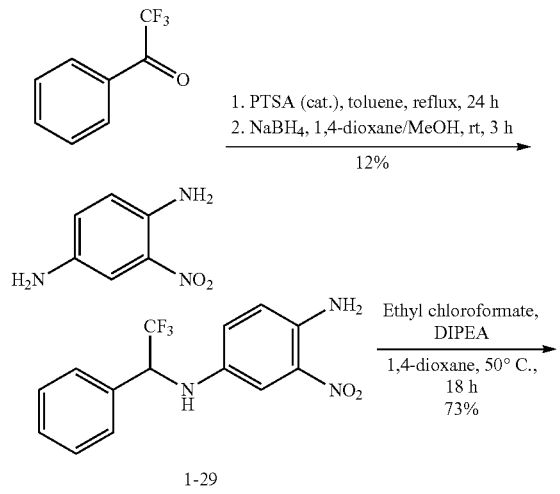

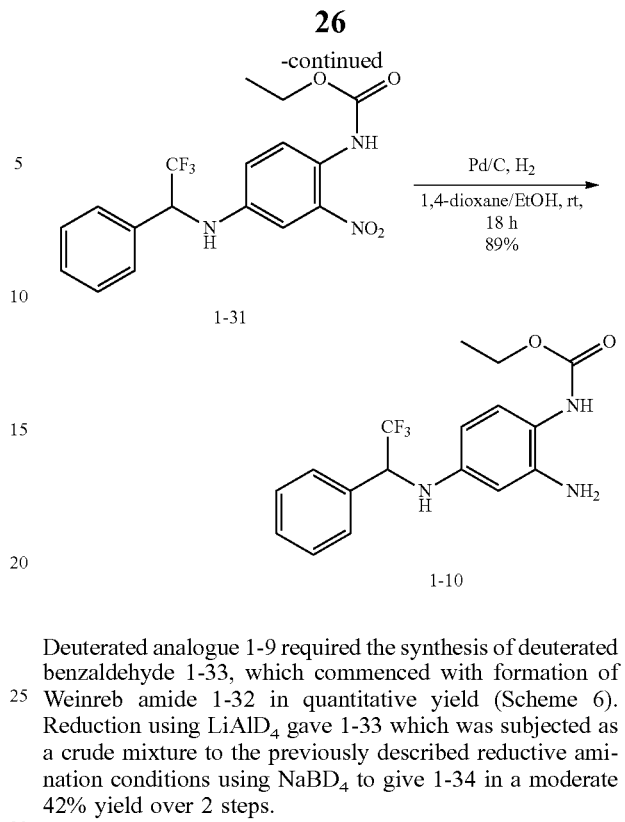

Deuterated analogue 1-9 required the synthesis of deuterated benzaldehyde 1-33, which commenced with formation of Weinreb amide 1-32 in quantitative yield (Scheme 6). Reduction using LiAlD₄ gave 1-33 which was subjected as a crude mixture to the previously described reductive amination conditions using NaBD₄ to give 1-34 in a moderate 42% yield over 2 steps.

Scheme 6. Synthesis of Deuterated Reductive Amination Product 1-34

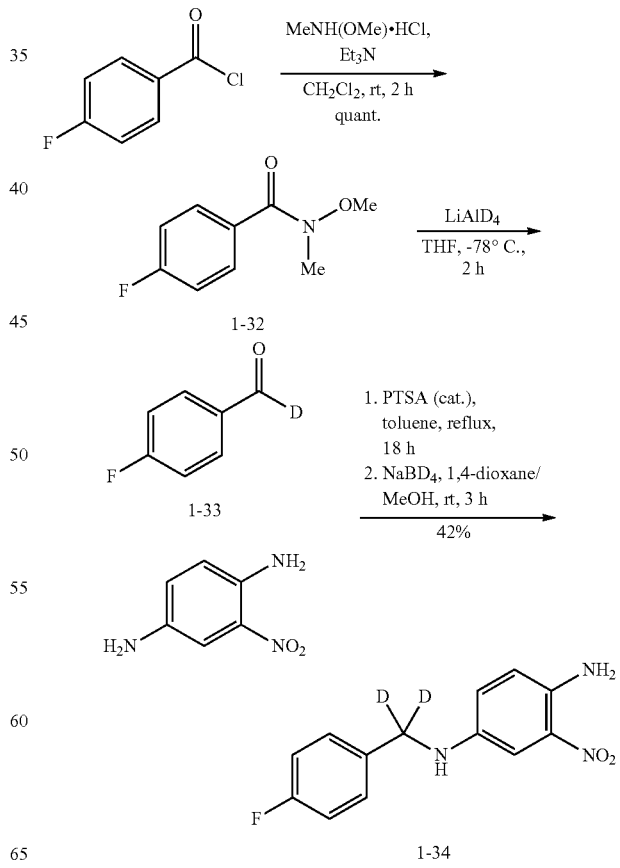

Protection and carbamoylation proceeded in comparable yield (56%) to previously prepared analogues to give 1-36. (Scheme 7) Reduction of the nitro group and cleavage of the Cbz protecting group using Pd/C and H₂ gave the desired deuterated analogue 1-9 in 75% yield.

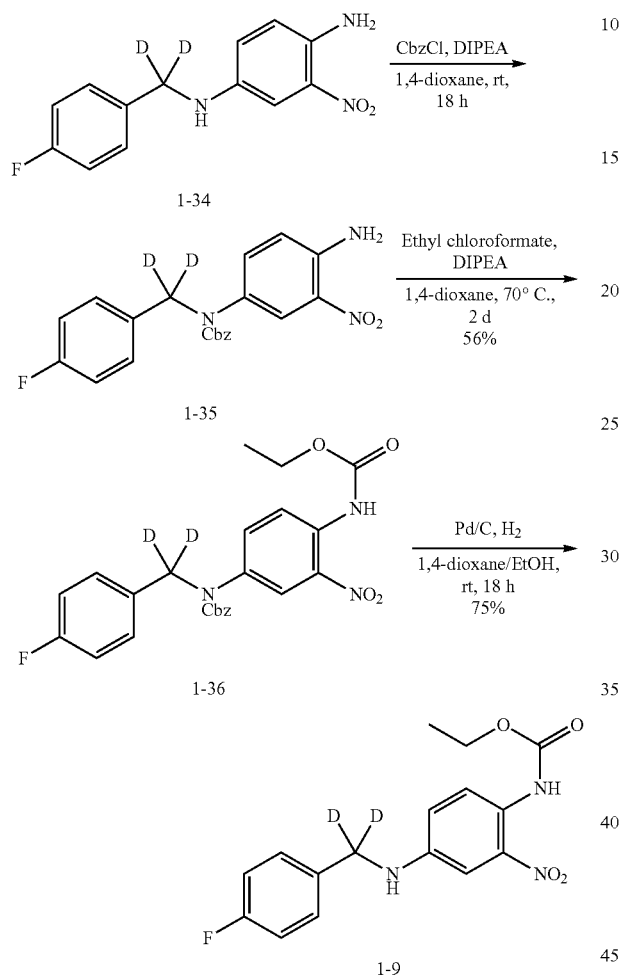

The final compounds to be made with alterations in zone 1 incorporated heteroaromatic structures. Use of molecular sieves and PTSA as a catalyst at room temperature allowed for the isolation of diamines 1-37 and 1-39 in 71% and 61% yield, respectively (Scheme 8). Protection and treatment with ethyl chloroformate gave ethyl carbamates 1-38 and 1-40 in good yield over 2 steps.

Scheme 8. Initial Attempts towards Heterocyclic Analogues of Retigabine

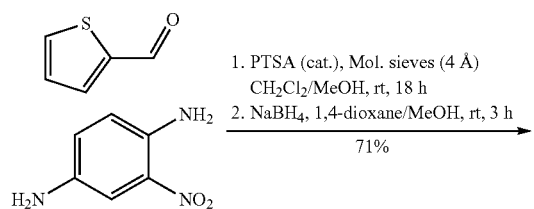

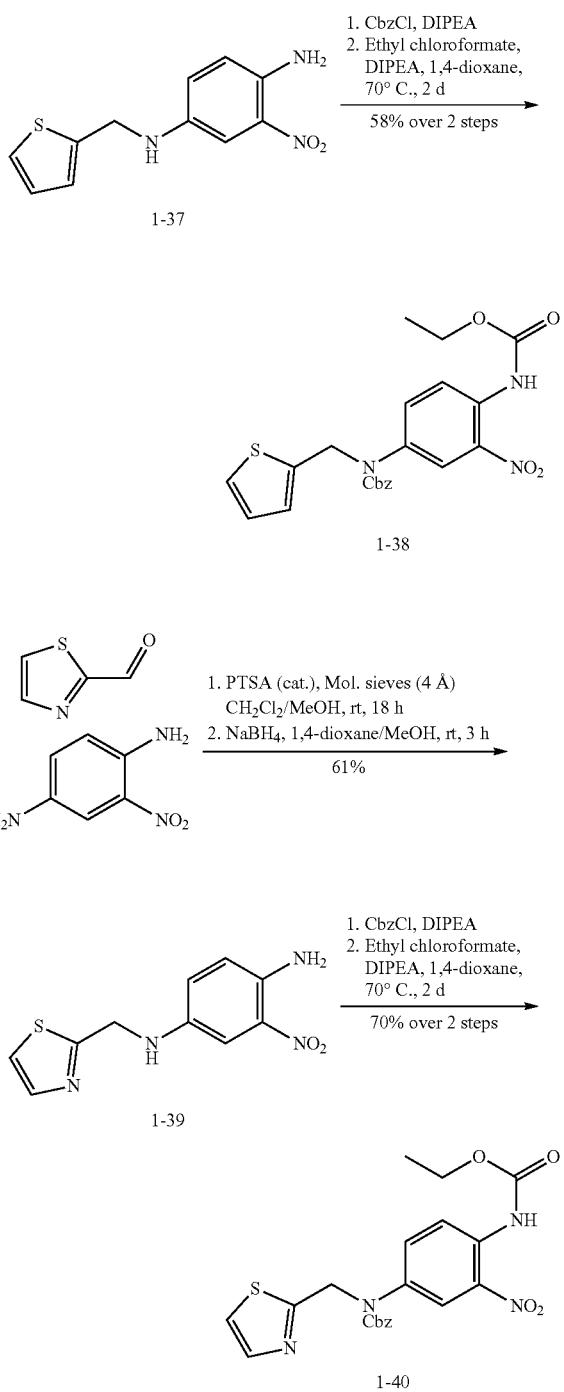

Reduction of the nitro group of 1-37 or 1-39 leading to an aryl triamine followed by treatment with an attenuated ethyl chloroformate equivalent could lead to the desired compounds without polycarbamoylation. Reduction of the nitro group of 1-37 and 1-39 using Pd/C and H₂ and subsequent reaction with mixed phthalidimidyl carbonate 1-41 and Et₃N in CH₂Cl₂ gave the desired heterocyclic analogues (1-11 and 1-12) in good yield over 2 steps (Scheme 9). This sequence has several advantages including the use of air and moisture stable carbamoylating reagents, shorter overall step count, and comparable overall yields.

Scheme 9. Synthesis of Heterocyclic Analogues of Retigabine

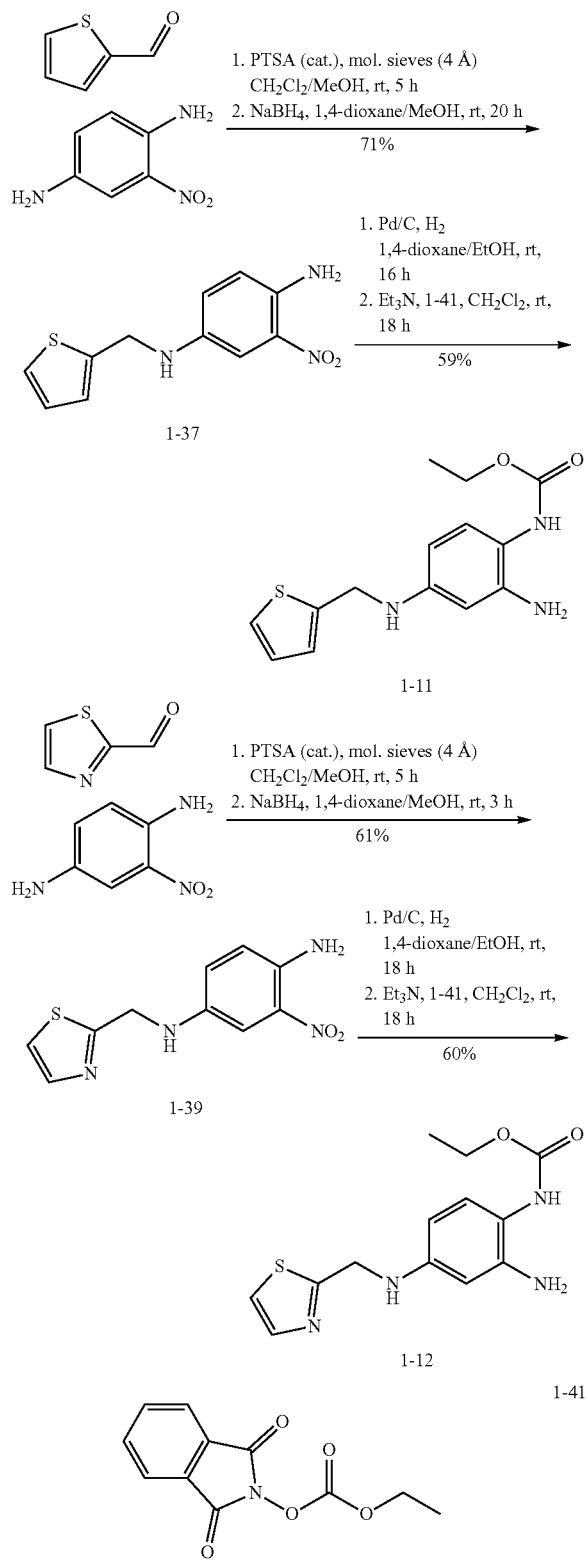

chloroformate. Reductive amination gave diamine 1-2 in 62% yield which was then protected and treated with isopropyl chloroformate, affording only 39% of the desired product over 2 steps (Scheme 10). Catalytic hydrogenation of 1-43 using Pd/C and $H_2$ gave 1-44 in good yield (74%).

Scheme 10. Synthesis of Isopropyl Carbamate Analogue 1-44

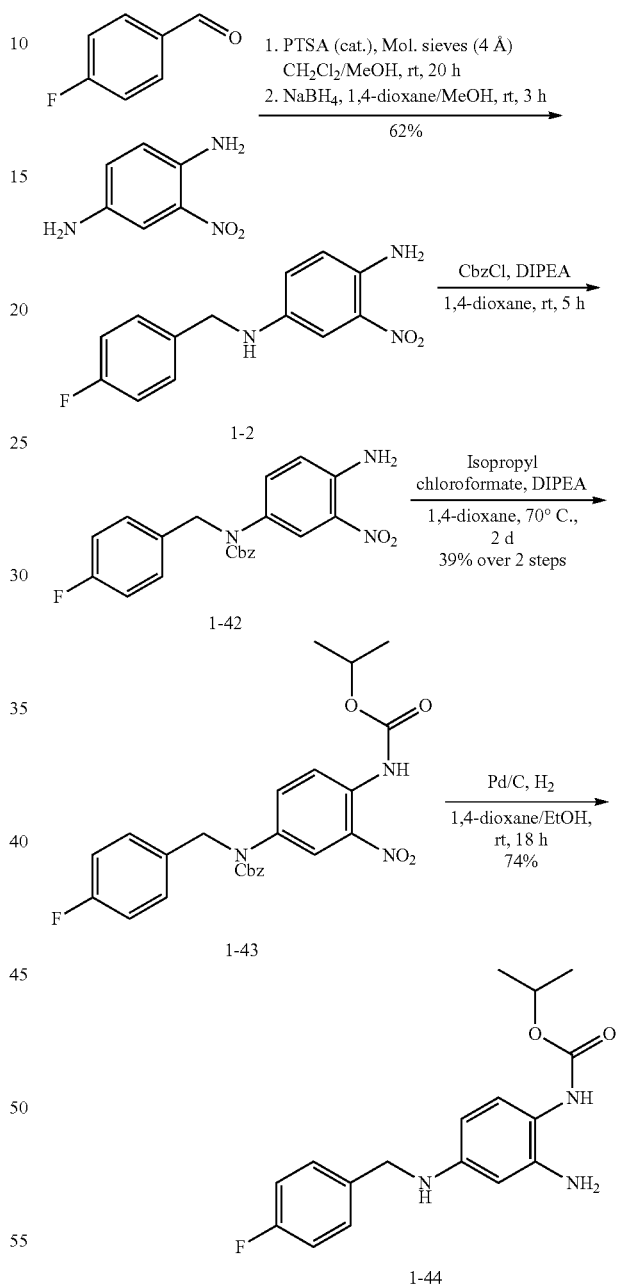

The analogues with alterations in zone 3 of retigabine were surprisingly difficult to access. The only compound successfully prepared via this method was the isopropyl carbamate analogue 1-44 due to the ready availability of isopropyl Mixed phthalidimidyl carbonates 1-46 and 1-47 enabled a controlled carbamoylation without any evidence of polycarbamoylation (Scheme 11). Thus, catalytic hydrogenation of 1-2 yielded triamine 1-45 which was then treated with a mixed carbonate (1-46 or 1-47) and $Et_3N$. Purification of compound 1-15 was complicated by closely eluting impurities but this target could be obtained in 29% yield over 2 steps. The MMS-350 derived compound 1-14 was obtained in better, albeit still modest, 39% yield.

Scheme 11. Synthesis of MMS-350 and 3-Methyl-3-Oxetanemethanol Modified Analogues

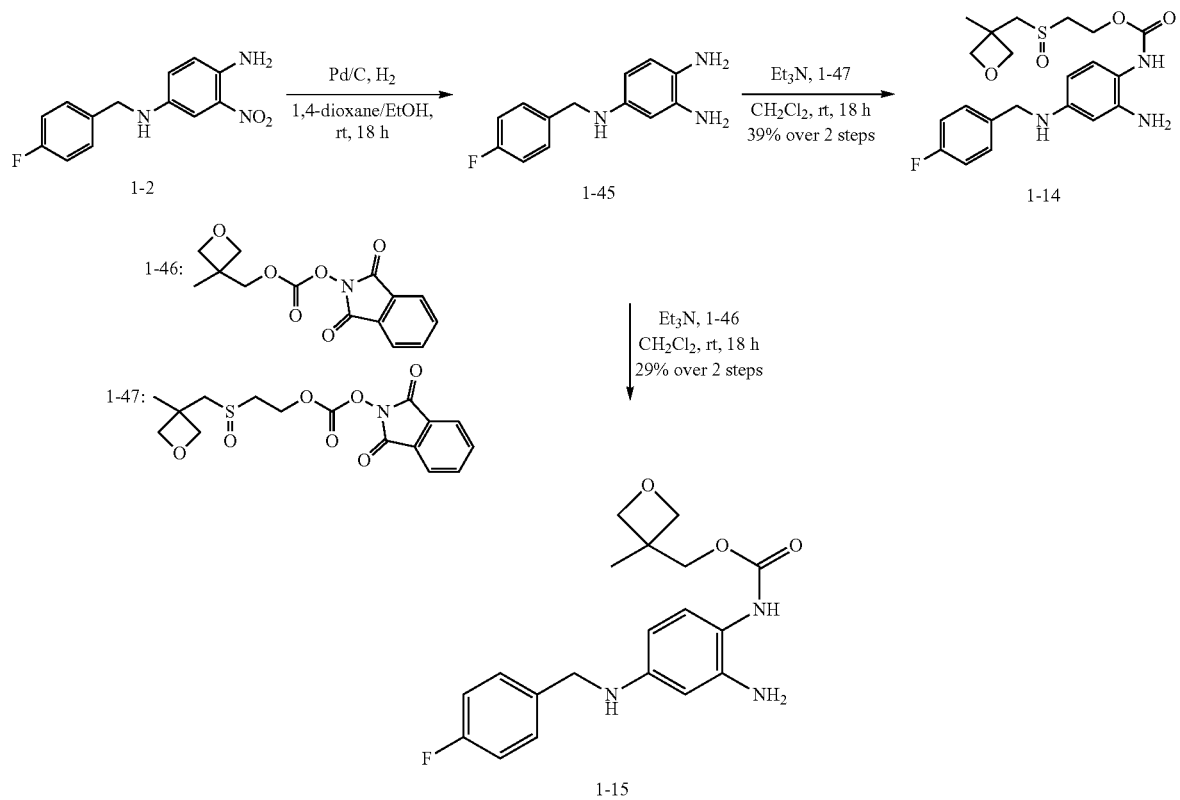

Finally, we also prepared a few analogs with selected zone 2 modifications to probe the biological effects of electronic and steric variations at this core site.

Compositions and Methods of Use

In certain embodiments, disclosed herein are methods for administrating a therapeutically effective amount of a compound disclosed herein to a subject for treating or preventing conditions by ameliorating a Kv7.2/3 potassium channel opening. In one aspect, the methods treat a subject suffering from or susceptible to conditions that are ameliorated by Kv7.2/3 potassium channel opening, comprising administering to the subject in need thereof a therapeutically effective amount of a compound disclosed herein, or a pharmaceutically acceptable salt thereof. In certain embodiments, the methods disclosed herein ameliorate such conditions by increasing the ion flow through Kv7.2/3 potassium channel(s).

In certain embodiments, there is provided a method of treating or preventing tinnitus in a subject in need thereof comprising administering to the subject a therapeutically effective amount of a compound disclosed herein, or a pharmaceutically acceptable salt thereof. The tinnitus may be a condition of, for example, age-related hearing loss, ear injury, circulatory system disorder, neurological damage, or ear infections.

In certain embodiments, there is provided a method of treating or preventing epilepsy in a subject in need thereof comprising administering to the subject a therapeutically effective amount of a compound disclosed herein, or a pharmaceutically acceptable salt thereof.

In certain embodiments, there is provided a method of producing an anti-epileptic, muscle relaxing, fever reducing, peripherally analgesic or anti-convulsive effect in a subject in need thereof comprising administering to the subject a therapeutically effective amount of a compound disclosed herein, or a pharmaceutically acceptable salt thereof.

In certain embodiments, the compounds disclosed herein are useful as an anti-convulsant. They are therefore useful in treating epilepsy. In one aspect, the method may by treating a subject suffering from or susceptible to epilepsy comprising administering to the subject in need thereof a therapeutically effective amount of a compound disclosed herein, or a pharmaceutically acceptable salt thereof. The compound may be employed to alleviate the symptoms of epilepsy in a host. "Epilepsy" is intended to include the following seizures:—simple partial seizures, complex partial seizures, secondary generalized seizures, generalized seizures including absence seizures, myoclonic seizures, clonic seizures, tonic seizures, tonic clonic seizures and atonic seizures.

Also disclosed herein are methods for treating or preventing a neurotransmission disorder, CNS disorder, functional bowel disorder, a neurodegenerative disease, a cognitive disorder, or migraine in a subject in need thereof comprising administering to the subject an effective amount of a compound disclosed herein, or a pharmaceutically acceptable salt hereof.

For example, the compounds may be are useful in the treatment of CNS disorders such as bipolar disorder, alternatively known as manic depression. Type I or II bipolar disorder may be treated. The compounds may thus be used to improve the condition of a human patient suffering from bipolar disorder. They may be used to alleviate the symptoms of bipolar disorder in a host. The compounds may also be used in the treatment of unipolar depression, ataxia, myokimia and anxiety.

In a further example, the compounds may be useful in the treatment of functional bowel disorders which include non-ulcer dyspepsia, non-cardiac chest pain and in particular irritable bowel syndrome. Irritable bowel syndrome is a gastrointestinal disorder characterized by the presence of abdominal pain and altered bowel habits without any evidence of organic disease. The compounds may thus be used to alleviate pain associated with irritable bowel syndrome. The condition of a human patient suffering from irritable bowel syndrome may thus be improved.

In another example, the compounds may be are useful as analgesics. They are therefore useful in treating or preventing pain. They may be used to improve the condition of a host, typically a human being, suffering from pain. They may be employed to alleviate pain in a host. Thus, the compounds may be used as a pre-emptive analgesic to treat acute pain such as musculoskeletal pain, post-operative pain and surgical pain, chronic pain such as chronic inflammatory pain (e.g. rheumatoid arthritis and osteoarthritis), neuropathic pain (e.g. post herpetic neuralgia, trigeminal neuralgia and sympathetically maintained pain) and pain associated with cancer and fibromyalgia. The compounds may also be used in the treatment or prevention of pain associated with migraine. The compounds may also be used in the treatment of the pain (both chronic and acute), fever and inflammation of conditions such as rheumatic fever; symptoms associated with influenza or other viral infections, such as the common cold; lower back and neck pain; headache; toothache; sprains and strains; myositis; neuralgia; synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

In a further example, the compounds may be useful in the treatment of neurodegenerative diseases, such as Alzheimer's disease, ALS, motor neuron disease, Parkinson's disease, macular degeneration and glaucoma. The compounds of the invention may also be useful in neuroprotection and in the treatment of neurodegeneration following stroke, cardiac arrest, pulmonary bypass, traumatic brain injury, spinal cord injury or the like.

In a further example, disclosed herein is a method for preventing or reducing dependence on, or preventing or reducing tolerance, or reverse tolerance, to a dependence-inducing agent in a subject in need thereof comprising administering to the subject an effective amount of a compound disclosed herein, or a pharmaceutically acceptable salt or solvate thereof. Examples of dependence inducing agents include opioids (e.g. morphine), CNS depressants (e.g. ethanol), psychostimulants (e.g. cocaine) and nicotine.

Also disclosed herein is a method for treating or preventing cancer, inflammatory disease, or ophthalmic disease in a subject in need thereof comprising administering to the subject an effective amount of a compound disclosed herein, or a pharmaceutically acceptable salt or solvate thereof.

The compounds may inhibit cellular and neoplastic transformation and metastatic tumor growth and hence are useful in the treatment of certain cancerous diseases, such as colonic cancer.

The compounds may inhibit inflammatory processes and therefore are of use in the treatment of asthma, allergic rhinitis and respiratory distress syndrome; gastrointestinal conditions such as inflammatory bowel disease, Crohn's disease, gastritis, irritable bowel syndrome and ulcerative colitis; and the inflammation in such diseases as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

The compounds may be useful in the treatment of ophthalmic diseases such as retinitis, retinopathies, uveitis and of acute injury to the eye tissue.

The compounds may be useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Loss; and learning deficiencies.

Further disclosed herein is a method of producing an anxiolytic effect in a subject in need thereof comprising administering to the subject a therapeutically effective amount of a compound disclosed herein, or a pharmaceutically acceptable salt or solvate thereof. In one aspect, the invention provides a method for the treatment of anxiety and its related psychological and physical symptoms. Anxiolytics have been shown to be useful in the treatment of anxiety disorders.

Also disclosed herein is a method for treating a subject suffering from or susceptible to epilepsy comprising co-administering to the subject in need thereof a therapeutically effective amount of a compound disclosed herein and one or more anti-epileptic drugs (AEDs). There are different types of AEDs. For example, narrow-spectrum AEDs include e.g., phenyloin (Dilantin), phenobarbital, carbamazepine (Tegretol), oxcarbazepine (Trileptal), gabapentin (Neurontin), pregabalin (Lyrica), lacosamide (Vimpat), and vigabatrin (Sabril). Broad spectrum AEDs include e.g., valproic acid (Depakote), lamotrigine (Lamictal), topiramate (Topamax), zonisamide (Zonegran), levetiracetam (Keppra), clonazepam (Klonopin), and rufinamide (Banzel). In one aspect, the AED is any AED. In one aspect, the AED is a narrow spectrum AED. In one aspect, the AED is a broad spectrum AED.

In certain embodiments, the subject is in need of, or has been recognized as being in need of, treatment with a Kv7.2/3 activator. The subject may be selected as being amenable to treatment with a Kv7.2/3 activator.

In some embodiments, the methods disclosed herein involve administering to a subject in need of treatment a pharmaceutical composition, for example a composition that includes a pharmaceutically acceptable carrier and a therapeutically effective amount of one or more of the compounds disclosed herein. The compounds may be administered orally, parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmically, or rectally. The pharmaceutical composition may be administered in dosage unit formulations containing conventional non-toxic pharmaceutically acceptable carriers, adjuvants, and/or vehicles. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

In some embodiments, one or more of the disclosed compounds (including compounds linked to a detectable label or cargo moiety) are mixed or combined with a suitable pharmaceutically acceptable carrier to prepare a pharmaceutical composition. Pharmaceutical carriers or vehicles suitable for administration of the compounds provided herein include any such carriers known to be suitable for the particular mode of administration. *Remington: The Science and Practice of Pharmacy*, The University of the Sciences in Philadelphia, Editor, Lippincott, Williams, & Wilkins, Philadelphia, Pa., 21$^{st}$ Edition (2005), describes exemplary compositions and formulations suitable for pharmaceutical delivery of the compounds disclosed herein. In addition, the compounds may be formulated as the sole pharmaceutically active ingredient in the composition or may be combined with other active ingredients.

Upon mixing or addition of the compound(s) to a pharmaceutically acceptable carrier, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions. The disclosed compounds may also be prepared with carriers that protect them against rapid elimination from the body, such as time-release formulations or coatings. Such carriers include controlled release formulations, such as, but not limited to, microencapsulated delivery systems.

The disclosed compounds and/or compositions can be enclosed in multiple or single dose containers. The compounds and/or compositions can also be provided in kits, for example, including component parts that can be assembled for use. For example, one or more of the disclosed compounds may be provided in a lyophilized form and a suitable diluent may be provided as separated components for combination prior to use. In some examples, a kit may include a disclosed compound and a second therapeutic agent for co-administration. The compound and second therapeutic agent may be provided as separate component parts. A kit may include a plurality of containers, each container holding one or more unit dose of the compound. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The active compound is included in the pharmaceutically acceptable carrier in an amount sufficient to exert a therapeutically useful effect in the absence of undesirable side effects on the subject treated. A therapeutically effective concentration may be determined empirically by testing the compounds in known in vitro and in vivo model systems for the treated disorder. In some examples, a therapeutically effective amount of the compound is an amount that lessens or ameliorates at least one symptom of the disorder for which the compound is administered. Typically, the compositions are formulated for single dosage administration. The concentration of active compound in the drug composition will depend on absorption, inactivation, and excretion rates of the active compound, the dosage schedule, and amount administered as well as other factors known to those of skill in the art.

In some examples, about 0.1 mg to 1000 mg of a disclosed compound, a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s).

The disclosed compounds or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is to be noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the compound is typically provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily. In some examples, an oral dosage form is administered to the subject 1, 2, 3, 4, or more times daily. When administered orally, an administered amount therapeutically effective may be from about 0.1 mg/day to about 1,000 mg/day. In certain examples, the oral dosage is from about 1 mg/day to about 500 mg/day, about 2 mg/day to about 200 mg/day, or about 5 mg/day to about 50 mg/day. It is understood that while a subject may be started at one dose, that dose may be varied over time as the subject's condition changes.

In additional examples, the compounds can be administered orally to humans in a dosage range of 1 to 1000 mg/kg body weight in single or divided doses. One illustrative dosage range is 0.1 to 200 mg/kg body weight orally (such as 0.5 to 100 mg/kg body weight orally) in single or divided doses. For oral administration, the compositions may be provided in the form of tablets containing about 1 to 1000 milligrams of the active ingredient, particularly 1, 5, 10, 15, 20, 25, 50, 75, 100, 150, 200, 250, 300, 400, 500, 600, 750, 800, 900, or 1000 milligrams of the active ingredient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The compounds can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The compounds can also be administered sublingually. When given sublingually, the compounds should be given one to four times daily in the amounts described above for IM administration.

The compounds can also be administered intranasally. When given by this route, the appropriate dosage forms are a nasal spray or dry powder. The dosage of the compounds for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds can be administered intrathecally. When given by this route, the appropriate dosage form can be a parenteral dosage form. The dosage of the compounds for intrathecal administration is the amount described above for IM administration.

The compounds can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used.

The compounds can be administered rectally by suppository. When administered by suppository, an illustrative therapeutically effective amount may range from about 0.5 mg to about 500 mg. When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

It should be apparent to one skilled in the art that the exact dosage and frequency of administration will depend on the particular compounds administered, the particular condition being treated, the severity of the condition being treated, the age, weight, general physical condition of the particular subject, and other medication the individual may be taking as is well known to administering physicians or other clinicians who are skilled in therapy of retroviral infections, diseases, and associated disorders.

EXAMPLES

Fusiform cell, principal neurons in the dorsal cochlear nucleus, fire spontaneous action potentials and Kv7.2/3 channels affects the spontaneous firing rate of fusiform cells dramatically (Li et al., 2013). To test the efficacy of the compounds, we bath applied 10 μM of the different compounds onto spontaneously firing fusiform neurons. Compounds that inhibited spontaneous firing are targeting Kv7.2/3 channels. Consistent with this conclusion, the observed inhibition was reversed upon blocking Kv7.2/3 channels by bath application of 10 μM XE991 (10,10-bis(4-pyrindylmethyl)-9(10H)-anthracenone).

All reactions were performed under an $N_2$ atmosphere and all glassware was dried in an oven at 130° C. for at least 2 h prior to use and allowed to cool under an atmosphere of dry $N_2$ or Ar unless otherwise stated. Reactions carried out below 0° C. employed an acetone/dry ice bath or a cryocool and an acetone bath. THF and $Et_2O$ were distilled over sodium/benzophenone ketyl, $CH_2Cl_2$ and toluene were distilled over $CaH_2$, and 1,4-dioxane, MeOH, and MeCN were dried batchwise over 3 Å molecular sieves unless otherwise noted. $Et_3N$ and DIPEA were distilled from $CaH_2$ and stored over KOH. Concentration under reduced pressure refers to the use of a rotary evaporator connected to a PIAB Lab Vac H40 to remove solvent and drying under high vacuum refers to the use of a Fischer Scientific Maxima C Plus vacuum pump (0.5-4 mmHg) to remove traces of solvent. All flash column chromatography was performed with normal phase $SiO_2$ (Silicycle, 40-63 μm particle size). Reactions were monitored by thin-layer chromatography (Merck pre-coated silica gel 60 $F_{254}$ plates, 250 μm layer thickness) and visualization was accomplished with a 254 nm UV light, by staining with $KMnO_4$ solution (1.5 g of $KMnO_4$ and 1.5 g of $K_2CO_3$ in 100 mL of a 0.1% NaOH solution), or by staining with p-anisaldehyde solution (2.5 mL of p-anisaldehyde, 2 mL of AcOH, and 3.5 mL of conc. $H_2SO_4$ in 100 mL of 95% EtOH).

Melting points were obtained using a Laboratory Devices Mel-Temp II using open capillaries and are uncorrected. $^1H$ and $^{13}C$ NMR spectra were obtained on Bruker Avance 300, 400, or 500 instruments as indicated. $^1H$ spectra were obtained at 300, 400, or 500 MHz in $CDCl_3$ and $(CD_3)_2SO$ unless otherwise noted. Chemical shifts were reported in parts per million with the residual solvent peak used as an internal standard. $^1H$ NMR spectra were obtained and are tabulated as follows: chemical shift, multiplicity (s=singlet, d=doublet, t=triplet, q=quartet, quint=quintet, dd=double of doublets, dt=doublet of triplets, m=multiplet, br=broad, app=apparent), number of protons, and coupling constant(s). $^{13}C$ NMR were run at 75, 100, 125, or 175 MHz as specified using a proton-decoupled pulse sequence and are tabulated by observed peak. Infrared spectra were measured on a PerkinElmer Spectrum100 FT-IR Spectrometer (ATR). High resolution mass spectra were obtained on a Thermo Fisher Exactive Orbitrap LC-MS using heated electrospray ionization (HESI).

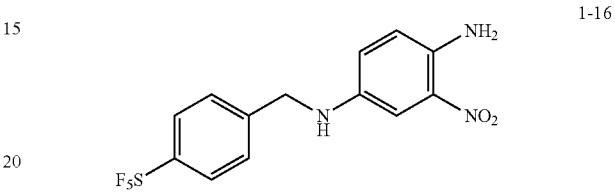

1-16

(4-Amino-3-nitrophenyl)[(4-pentafluorothiophenyl)methyl]amine (1-16) To a solution of 2-nitro-p-phenylenediamine (0.751 g, 4.66 mmol) and PTSA (0.045 g, 0.24 mmol) in toluene (25 mL) was added 4-(pentafluorothio)benzaldehyde (1.115 g, 4.707 mmol). The resulting solution was heated to reflux with a Dean-Stark trap for 21 h, the mixture was filtered through a Buchner funnel packed with a thin pad of $SiO_2$, and the filtrate was stirred and allowed to cool to rt. The solvent was removed under reduced pressure to give the crude imine (1.10 g) as a bright orange-red solid, that was suspended in a mixture of 1,4-dioxane (5.2 mL) and MeOH (1.3 mL) and $NaBH_4$ (0.120 g, 3.14 mmol) was added in 3 portions at 15 min intervals. The resulting solution was allowed to stir at rt for 3 h, quenched with $H_2O$ (25 mL) and the resulting solid collected by filtration. The crude compound was washed with $H_2O$ (500 mL) and dried under high vacuum to give 1 (1.09 g, 2.95 mmol, 63%) as a dark purple powder: Mp 129-130° C. ($H_2O$); IR (ATR) 3522.90, 3397.94, 1576.91, 1531.83, 1327.68, 1216.31 cm$^{-1}$; $^1H$ NMR ($CDCl_3$, 400 MHz) δ 7.73 (d, 2 H, J=8.4 Hz), 7.61 (d, 2 H, J=8.4 Hz), 7.27 (d, 1 H, 2.8 Hz), 6.84 (dd, 1 H, J=9.2, 2.8 Hz), 6.71 (d, 1 H, J=8.8 Hz), 5.74 (br s, 2 H), 4.37 (s, 2 H), 3.92 (br s, 1 H); $^{13}C$ NMR ($CDCl_3$, 100 MHz) δ 153.2 (app. t, J=17.5 Hz), 143.0, 138.9, 138.5, 132.6, 127.7, 126.5 (quint., J=4.6 Hz), 125.3, 120.4, 106.2, 48.1; HRMS (HESI) m/z calcd for $C_{13}H_{13}N_3O_2F_5S$ (M+H) 370.0643, found 370.0645.

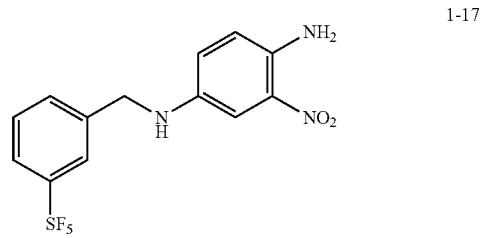

1-17

(4-Amino-3-nitrophenyl)[(3-pentafluorothiophenyl)methyl]amine (1-17) A solution of 2-nitro-p-phenylenediamine (0.756 g, 4.69 mmol) and PTSA (0.054 g, 0.28 mmol) in toluene (25 mL) was treated with 3-(pentafluorothio)benzaldehyde (1.10 g, 4.56 mmol) via syringe and the resulting solution was heated to reflux with a Dean-Stark trap for 5 h. The mixture was filtered through a Buchner funnel packed with a thin pad of SiO$_2$ and the filtrate was stirred and allowed to cool to rt. The solvent was removed under reduced pressure to give the crude imine (1.571 g) as a bright orange-red solid, that was suspended in a mixture of 1,4-dioxane (5.2 mL) and MeOH (1.3 mL) and NaBH$_4$ (0.126 g, 3.30 mmol) was added in 3 portions at 15 min intervals. The resulting solution was allowed to stir at rt for 3 h, quenched with H$_2$O (25 mL), and extracted from brine with CH$_2$Cl$_2$ (3×200 mL). The solvent was removed under reduced pressure and the resulting residue dried under high vacuum at 60° C. for 12 h to give 1-17 (1.36 g, 3.69 mmol, 79%) as a dark red-purple powder: Mp 128-129° C. (CH$_2$Cl$_2$); IR (ATR) 3477.56, 3422.45, 3360.67, 3109.99, 1574.79, 1515.17, 1206.56; $^1$H NMR (CDCl$_3$, 400 MHz) δ 7.77 (s, 1 H), 7.68 (d, 1 H, J=8.4 Hz), 7.53 (d, 1 H, 7.6 Hz), 7.47-7.43 (m, 1 H), 7.30 (d, 1 H, J=2.8 Hz), 6.86 (dd, 1 H, J=8.8, 2.8 Hz), 6.72 (d, 1 H, J=8.8 Hz), 5.75 (br s, 2 H), 4.37 (s, 2 H), 3.89 (br s, 1 H); $^{13}$C NMR (CDCl$_3$, 100 MHz) 154.4 (quint., J=18.0 Hz), 140.3, 139.0, 138.5, 132.6, 130.7, 129.3, 125.4, 125.3-125.1 (overlapping quint.), 120.4, 106.4, 48.6; HRMS (HESI) m/z calcd for C$_{13}$H$_{13}$N$_3$O$_2$F$_5$S (M+H) 370.0643, found 370.0641.

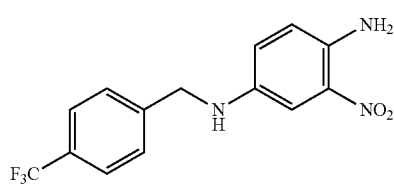

1-18

(4-Amino-3-nitrophenyl){[4-(trifluoromethyl)phenyl]methyl}amine (1-18) A solution of 2-nitro-p-phenylenediamine (0.754 g, 4.68 mmol) and PTSA (0.054 g, 0.28 mmol) in toluene (25 mL) was treated via syringe with 4-(trifluoromethyl)benzaldehyde (0.640 mL, 4.69 mmol) and the resulting solution was heated at reflux with a Dean-Stark trap for 5 h. The mixture was filtered through a Buchner funnel packed with a thin pad of SiO$_2$ and the filtrate was stirred and allowed to cool to rt. The solvent was removed under reduced pressure to give the crude imine (1.23 g) as a bright orange-red solid, that was suspended in a mixture of 1,4-dioxane (5.2 mL) and MeOH (1.3 mL) and NaBH$_4$ (0.120 g, 3.14 mmol) was added in 3 portions at 15 min intervals. The resulting solution was allowed to stir at rt for 3 h, quenched with H$_2$O (25 mL) and extracted from brine with CH$_2$Cl$_2$ (3×200 mL). The solvent was removed under reduced pressure and the residue dried under high vacuum at 60° C. to give 1-18 (1.141 g, 3.666 mmol, 78%) as a dark purple oil: IR (CH$_2$Cl$_2$) 3483.58, 3370.03, 1573.93, 1521.07, 1324.97 cm$^{-1}$; $^1$H NMR (CDCl$_3$, 400 MHz) δ 7.60 (d, 2 H, J=8.0 Hz), 7.48 (d, 2 H, J=8.0 Hz), 7.28 (d, 1 H, J=2.8 Hz), 6.85 (dd, 1 H, J=8.8, 2.8 Hz), 6.71 (d, 1 H, J=8.8 Hz), 5.47 (br s, 2 H), 4.37 (s, 2 H), 3.92 (br s, 1 H); $^{13}$C NMR (CDCl$_3$ 100 MHz) δ 143.1, 139.1, 138.4, 132.6, 129.9 (q, J=32.1 Hz), 127.8, 125.8 (q, J=3.6 Hz), 125.3, 124.2 (q, J=270.0 Hz), 120.3, 106.1, 48.5; HRMS (HESI) m/z calcd for C$_{14}$H$_{13}$N$_3$O$_2$F$_3$(M+H) 312.0954, found 312.0955.

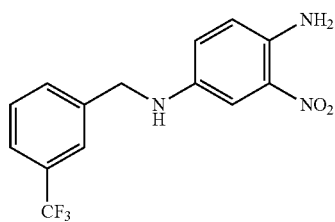

1-19

(4-Amino-3-nitrophenyl){[3-(trifluoromethyl)phenyl]methyl}amine (1-19) A solution of 2-nitro-p-phenylenediamine (0.753 g, 4.67 mmol) and PTSA (0.050 g, 0.26 mmol) in toluene (25 mL) was treated via syringe with 3-(trifluoromethyl)benzaldehyde (0.620 mL, 4.64 mmol). The resulting solution was heated to reflux with a Dean-Stark trap for 5 h, filtered through a Buchner funnel packed with a thin pad of SiO$_2$, and allowed to cool to rt. The solvent was removed under reduced pressure to give the crude imine (1.203 g) as bright orange solid, that was suspended in a mixture of 1,4-dioxane (3.7 mL) and MeOH (0.90 mL) and NaBH$_4$ (0.117 g, 0.655 mmol) was added in 3 portions at 15 minute intervals. The resulting solution was allowed to stir at rt for 3 h, quenched with H$_2$O (25 mL), and extracted with CH$_2$Cl$_2$ (3×100 mL). The combined organic extracts were washed with brine, dried (Na$_2$SO$_4$), filtered, and the solvent evaporated under reduced pressure to give crude 1-19 (1.141 g). Purification by chromatography on SiO$_2$ (70% CH$_2$Cl$_2$ in hexanes) gave 1-19 (1.10 g, 3.35 mmol, 72%) as a dark purple powder: Mp 95-96° C. (CH$_2$Cl$_2$); IR (ATR) 3456.00, 3396.67, 3330.69, 1515.08, 1323.54 cm$^{-1}$; $^1$H NMR (CDCl$_3$, 400 MHz) δ 7.64 (s, 1H), 7.55 (m, 2 H), 7.47 (m, 1 H), 7.29 (d, 1 H, J=2.8 Hz), 6.86 (dd, 1 H, J=8.8, 2.8 Hz), 6.71 (d, 1 H, J=8.8 Hz), 5.74 (br s, 2 H), 4.36 (s, 2 H), 3.89 (br s, 1 H); $^{13}$C NMR (CDCl$_3$, 100 MHz) δ 140.0, 139.16, 138.5, 132.6, 131.2 (q, J=32 Hz), 131.0, 129.3, 125.4, 124.5 (q, J=3.7 Hz), 124.4 (q, J=3.8 Hz), 124.2 (q, J=271 Hz), 120.3, 106.2, 48.6; HRMS (ESI) m/z calcd for C$_{14}$H$_{13}$N$_2$O$_3$F$_3$ (M+H) 312.0954, found 312.0947.

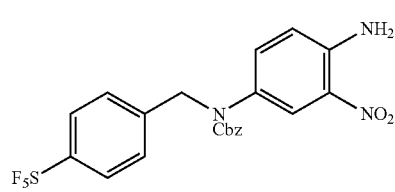

1-20

N-(4-Amino-3-nitrophenyl)(phenylmethoxy)-N-{[4-(pentafluorothio)phenyl]methyl}carboxamide (1-20) A solution of 1-16 (0.207 g, 0.544 mmol) and DIPEA (0.110 mL, 0.665 mmol) in 1,4-dioxane (2.8 mL) at rt was treated dropwise via syringe with benzyl chloroformate (0.100 mL, 0.682 mmol). The resulting solution was allowed to stir for 18 h and was then quenched with 1:1 H$_2$O:CH$_2$Cl$_2$ (6.5 mL). The phases were separated and the aqueous phase extracted with CH$_2$Cl$_2$ (3×5 mL). The combined organic phases were washed with brine, dried (Na$_2$SO$_4$), filtered, and the solvent evaporated to give crude 1-20 (0.280 g) as an orange foam that was used without further purification.

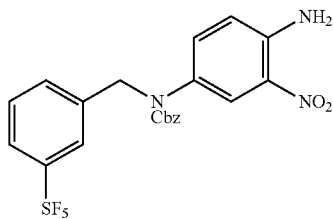

1-21

N-(4-Amino-3-nitrophenyl)(phenylmethoxy)-N-{[3-(pentafluorothio)phenyl]methyl}carboxamide (1-21) A solution of 1-17 (0.202 g, 0.531 mmol) and DIPEA (0.090 mL, 0.54 mmol) in 1,4-dioxane (2.8 mL) at rt was treated dropwise via syringe with benzyl chloroformate (0.080 mL, 0.55 mmol). The resulting solution was allowed to stir for 3 h and was then quenched with 6.50 mL of 1:1 $H_2O:CH_2Cl_2$. The phases were separated and the aqueous phase extracted with $CH_2Cl_2$ (3×5 mL). The combined organic phases were washed with brine, dried ($Na_2SO_4$), filtered, and the solvent evaporated to give crude 1-21 (0.309 g) as an orange oil which was used without further purification.

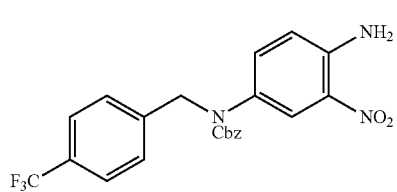

1-22

N-(4-Amino-3-nitrophenyl)(phenylmethoxy)-N-{[4-(trifluoromethyl)phenyl]methyl}carboxamide (1-22) A solution of 1-18 (0.199 g, 0.639 mmol) and DIPEA (0.110 mL, 0.666 mmol) in 1,4-dioxane (3.2 mL) at rt was treated dropwise via syringe with benzyl chloroformate (0.100 mL, 0.682 mmol). The resulting solution was allowed to stir for 4 h and was then quenched with 1:1 $H_2O:CH_2Cl_2$ (6.5 mL). The phases were separated and the aqueous phase extracted with $CH_2Cl_2$ (3×5 mL). The combined organic phases were washed with brine, dried ($Na_2SO_4$), filtered, and the solvent evaporated to give crude 1-22 (0.328 g) as a dark orange oil which was used without further purification.

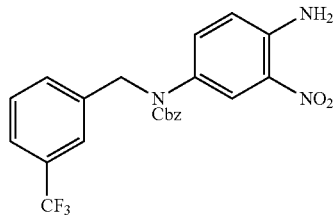

1-23

N-(4-Amino-3-nitrophenyl)(phenylmethoxy)-N-{[3-(trifluoromethyl)phenyl]methyl}carboxamide (1-23) A solution of 1-19 (0.205 g, 0.659 mmol) and DIPEA (0.115 mL, 0.696 mmol) in 1,4-dioxane (3.5 mL) at rt was treated dropwise via syringe with benzyl chloroformate (0.100 mL, 0.682 mmol). The resulting solution was allowed to stir for 4 h at rt and was then quenched with 1:1 $H_2O:CH_2Cl_2$ (10 mL), the layers were separated, and the aqueous phase was extracted with $CH_2Cl_2$ (2×15 mL). The combined organic phases were washed with $H_2O$ and brine, dried ($Na_2SO_4$), filtered, and the solvent evaporated to give crude 1-23 (0.331 g) as an orange oil which was used without further purification.

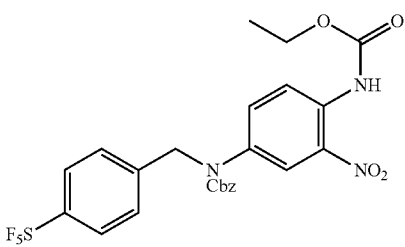

1-24

Ethoxy-N-(4-{N-[(4-pentafluorothiophenyl)methyl](phenylmethoxy)carbonylamino}-2-nitrophenyl)carboxamide (1-24) A solution of crude 1-20 (0.050 g, 0.099 mmol) and DIPEA (0.050 mL, 0.30 mmol) in 1,4-dioxane (1.0 mL) at rt was treated dropwise via syringe with ethyl chloroformate (0.030 mL, 0.31 mmol). The resulting solution was allowed to stir at 70° C. for 24 h and was then quenched with 1:1 $H_2O:CH_2Cl_2$ (5 mL). The phases were separated and the aqueous phase extracted with $CH_2Cl_2$ (3×20 mL). The combined organic phases were washed with $H_2O$ and brine, dried ($MgSO_4$), filtered, and the solvent evaporated under reduced pressure to give crude 1-24 (0.050 g) as an orange oil. The crude residue was purified by chromatography on $SiO_2$ (30% EtOAc in hexanes) to give 1-24 (0.036 g, 0.063 mmol, 63%, 82% brsm) as an orange oil: IR ($CH_2Cl_2$) 3365.79, 2094.66, 1738.05, 1706.74, 1515.21 $cm^{-1}$; $^1H$ NMR ($CDCl_3$, 400 MHz) δ 9.77 (s, 1 H), 8.54 (d, 1 H, J=9.2 Hz), 8.04 (br s, 1 H), 7.68 (d, 2 H, J=8.8 Hz), 7.33-7.27 (m, 5 H), 7.24-7.22 (m, 2 H), 5.19 (s, 2 H), 4.92 (s, 2 H), 4.26 (q, 2 H, J=7.2 Hz), 1.34 (t, 3 H, J=7.2 Hz); $^{13}C$ NMR ($CDCl_3$, 100 MHz) δ 155.2, 153.4 (quint., J=18.0 Hz), 153.2, 153.2, 141.0, 135.8, 135.7, 134.2, 128.8, 128.8, 128.2, 127.9, 126.6 (app. t, J=4.6 Hz), 123.6, 121.4, 68.5, 62.3, 53.4, 14.5; HRMS (HESI) m/z calcd for $C_{24}H_{23}N_3O_6F_5S$ (M+H) 576.1222, found 576.1221.

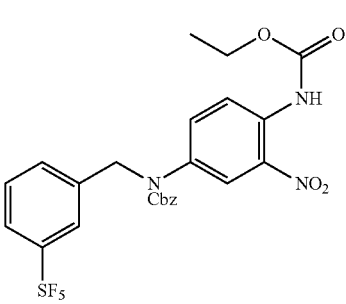

1-25

Ethoxy-N-(4-{N-[(4-pentafluorothiophenyl)methyl](phenylmethoxy)carbonylamino}-2-nitrophenyl)carboxamide (1-25) A solution of crude 1-21 (0.326 g), DIPEA (0.280 mL, 1.69 mmol), and DMAP (0.003 g, 0.02 mmol) in 1,4-dioxane (4 mL) at rt was treated dropwise via syringe with ethyl chloroformate (0.155 mL, 1.58 mmol). The resulting solution was allowed to stir at 70° C. for 2 d and was then quenched by the addition of 1:1 $H_2O:CH_2Cl_2$ (10 mL). The phases were separated and the aqueous phase extracted with $CH_2Cl_2$ (3×20 mL). The combined organic phases were washed with H₂O, 1 M aq. HCl, and brine, dried (MgSO₄), filtered, and the solvent evaporated under reduced pressure to give crude 1-25 (0.340 g) as an orange oil. The crude residue was purified by chromatography on SiO₂ (20% EtOAc in hexanes) to give 1-25 (0.052 g) as a yellow oil which was used without further purification.

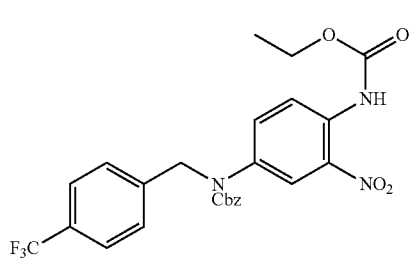

1-26

Ethoxy-N-[2-nitro-4-((phenylmethoxy)-N-{[4-(trifluoromethyl)phenyl]methyl}carbonylamino)phenyl]carboxamide (1-26) A solution of crude 1-22 (0.310 g) and DIPEA (0.670 mL, 4.05 mmol) in 1,4-dioxane (5.2 mL) at rt was treated dropwise via syringe with ethyl chloroformate (0.395 mL, 4.03 mmol). The resulting solution was allowed to stir at 70° C. for 3 d and was then quenched by the addition of 1:1 H₂O:CH₂Cl₂ (10 mL). The phases were separated and the aqueous phase extracted with CH₂Cl₂ (3×20 mL). The combined organic phases were washed with H₂O and brine, dried (Na₂SO₄), filtered, and the solvent evaporated under reduced pressure to give crude 1-26 (0.350 g) as an orange solid. The crude solid was purified by chromatography on SiO₂ (20% EtOAc in hexanes) to give 1-26 (0.194 g, 0.375 mmol, 59% over 2 steps) as an orange oil: IR (CH₂Cl₂) 3365.80, 2983.18, 1738.22, 1706.37, 1514.40, 1323.26 cm⁻¹; ¹H NMR (DMSO-d₆, 400 MHz, 353 K) δ 9.50 (br s, 1 H), 7.96 (d, 1 H, J=2.4 Hz), 7.77 (d, 1 H, J=8.8 Hz), 7.64 (d, 1 H, J=8.4 Hz), 7.60 (dd, 1 H, J=8.8, 2.4 Hz), 7.48 (d, 1 H, J=8.0 Hz), 7.33-7.26 (m, 7 H), 5.19 (s, 2 H), 5.05 (s, 2 H), 4.15 (q, 2 H, J=7.2 Hz), 1.24 (t, 3 H, J=7.2 Hz); ¹³C NMR (DMSO-d₆, 100 MHz, 353 K) δ 154.2, 152.9, 141.8, 140.0, 136.8, 135.8, 131.8, 130.3, 128.0, 127.9, 127.7, 127.5, 127.1, 124.9 (q, J=3.7 Hz), 123.8 (q, J=270.3 Hz), 123.8, 122.5, 67.0, 60.8, 52.3, 13.8; HRMS (HESI) m/z calcd for C₂₅H₂₁N₃O₆F₃ (M−H) 516.1377, found 516.1372.

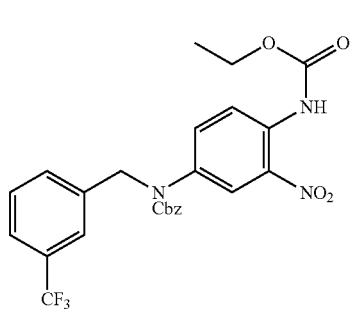

1-27

Ethoxy-N-[2-nitro-4-((phenylmethoxy)-N-{[3-(trifluoromethyl)phenyl]methyl}carbonylamino)phenyl]carboxamide (1-27) A solution of crude 1-23 (0.330 g) and DIPEA (0.545 mL, 3.30 mmol) in 1,4-dioxane (5 mL) at rt was treated dropwise via syringe with ethyl chloroformate (0.160 mL, 1.63 mmol). The resulting solution was allowed to stir at 70° C. for 2 d and was then quenched by the addition of 1:1 H₂O:CH₂Cl₂ (10 mL), the layers were separated and the aqueous phase was extracted with CH₂Cl₂ (2×20 mL). The combined organic phases were washed with H₂O (2×20 mL) and brine (2×10 mL), dried (MgSO₄), filtered, and the solvent evaporated under reduced pressure to give crude 1-27 (0.310 g) as an orange oil. The crude oil was purified by chromatography on SiO₂ (20% EtOAc in hexanes) to give 1-27 (0.113 g) as a yellow oil which was carried on without further purification.

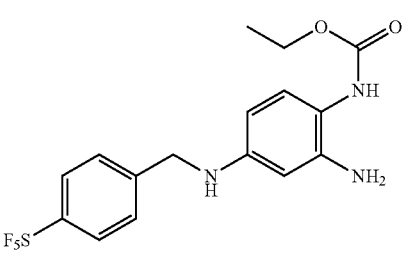

1-5

N-[2-amino-4-({[4-(pentafluorothio)phenyl]methyl}amino)phenyl]ethoxycarboxamide (1-5) A solution of 1-24 (0.047 g, 0.082 mmol) and 10% Pd/C (0.010 g, 0.009 mmol, 10 mol %) in a mixture of 1,4-dioxane (0.46 mL) and EtOH (0.24 mL) was allowed to stir for 21 h at rt under an H₂ atmosphere (balloon). The reaction mixture was diluted with Et₂O (5 mL) and filtered through a pad of Celite. The organic phase was concentrated under reduced pressure to give crude 1-5 (0.037 g) as an orange oil. The crude oil was purified by chromatography on SiO₂ (50% EtOAc in hexanes) to give 1-5 (0.018 g, 0.044 mmol, 54%) as a light brown solid: Mp 146-147° C. (CH₂Cl₂); IR (ATR) 3377.56, 2925.72, 1697.84, 1620.85, 1525.67 cm⁻¹; ¹H NMR (CDCl₃, 400 MHz) δ 7.70 (d, 2 H, J=8.4 Hz), 7.43 (d, 2 H, J=8.4 Hz), 6.92 (d, 1 H, J=8.4 Hz), 6.02 (dd, 1 H, J=8.4, 2.4 Hz), 5.95 (d, 1 H, J=2.4 Hz), 4.35 (s, 2 H), 4.18 (q, 2 H, J=7.2 Hz), 3.90 (br s, 2 H), 1.28 (t, 3 H, J=7.2 Hz); ¹³C NMR (CDCl₃, 100 MHz) δ 155.6, 152.9 (quint., J=13.5 Hz), 147.4, 143.9, 142.2, 128.1, 127.3, 126.4 (quint., J=4.0 Hz), 114.5, 104.5, 100.8, 61.5, 47.6, 14.7; HRMS (HESI) m/z calcd for C₁₆H₁₉N₃O₂F₅S (M+H) 412.1113, found 412.1111.

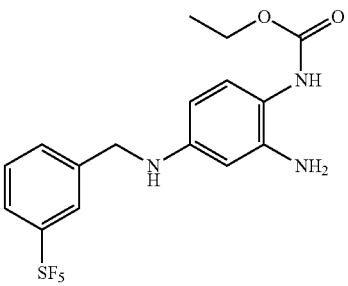

1-6

N-[2-Amino-4-({[3(pentafluorothio)phenyl]methyl}amino)phenyl]ethoxycarboxamide (1-6) A solution of 1-25 (0.050 g, 0.087 mmol) and 10% Pd/C (0.010 g, 0.010 mmol) in 1,4-dioxane (0.46 mL) and EtOH (0.24 mL) was allowed to stir under an H₂ atmosphere (balloon) for 18 h. The reaction mixture was diluted with Et₂O (5 mL) and filtered through a pad of Celite. The solvent was removed under reduced pressure to give crude 1-6 (0.049 g) as an orange oil. The crude residue was purified by chromatography on SiO$_2$ (50% EtOAc in hexanes) to give 1-6 (0.027 g, 0.066 mmol, 76%) as a light brown oil that solidified on standing: Mp 52-53° C. (CH$_2$Cl$_2$); IR (ATR) 3355.44, 2931.13, 1699.36, 1623.12, 1525.18, 1229.40 cm$^{-1}$; $^1$H NMR (CDCl$_3$, 400 MHz) δ 7.73 (s, 1 H), 7.65 (d, 1 H, J=8.0 Hz), 7.50 (d, 1 H, J=7.6 Hz), 7.42 (app. t, 1 H, J=7.8 Hz), 6.92 (d, 1 H, J=8.4 Hz), 6.04 (dd, 1 H, J=8.0, 2.0 Hz), 5.98 (d, 1 H, J=2.0 Hz), 4.34 (s, 2 H), 4.18 (q, 2 H, J=7.1 Hz), 3.85 (br s, 2H), 1.28 (t, 3 H, J=7.2 Hz); $^{13}$C NMR (CDCl$_3$, 175 MHz) δ 155.6, 154.4 (quint., J=16.8 Hz), 147.4, 143.1, 141.1, 130.4, 129.1, 128.0, 124.9 (quint., J=4.2 Hz), 124.8 (quint., J=4.4 Hz), 114.5, 104.5, 100.9, 61.5, 48.1, 14.7; HRMS (HESI) m/z calcd for C$_{16}$H$_{19}$N$_3$O$_2$F$_5$S (M+H) 412.1113, found 412.1101.

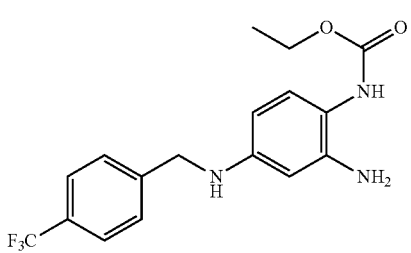

1-7

N-[2-Amino-4-({[4-(trifluoromethyl)phenyl]methyl}amino)phenyl]ethoxycarboxamide (1-7) A solution of 1-26 (0.090 g, 0.174 mmol) and 10% Pd/C (0.018 g, 0.017 mmol) in a mixture of 1,4-dioxane (1 mL) and EtOH (0.50 mL) was allowed to stir at rt for 18 h under an H$_2$ atmosphere (balloon). The reaction mixture was diluted with Et$_2$O (5 mL) and filtered through a pad of Celite. The organic phase was concentrated under reduced pressure to give crude 1-7 (0.051 g) as a light brown solid. The crude solid was purified by chromatography on SiO$_2$ (50% EtOAc in hexanes) to give 1-7 (0.044 g, 0.12 mmol, 72%) as a grey solid: Mp 171-172° C. (CH$_2$Cl$_2$); IR (ATR) 3279.60, 2980.62, 1677.20, 1526.96 cm$^{-1}$; $^1$H NMR (CDCl$_3$, 400 MHz) δ 7.59 (d, 2 H, J=8.4 Hz), 7.46 (d, 2 H, J=8.0 Hz), 6.92 (d, 1 H, J=8.4 Hz), 6.05 (dd, 1 H, J=8.4, 2.4 Hz), 5.98 (d, 1 H, J=2.4 Hz), 4.37 (s, 2 H), 4.19 (q, 2 H, J=7.2 Hz), 4.06 (br s, 1 H), 3.74 (br s, 2 H), 1.28 (t, 3 H, J=7.0 Hz); $^{13}$C NMR (CDCl$_3$, 100 MHz δ 155.7, 147.6, 143.9, 143.2, 129.6 (q, J=32.0 Hz), 128.1, 127.5, 125.7 (q, J=3.7 Hz), 124.3 (q, J=270.2 Hz), 114.3, 104.5, 100.6, 61.5, 48.0, 14.8; HRMS (HESI) m/z calcd for C$_{17}$H$_{19}$N$_3$O$_2$F$_3$(M+H) 354.1424, found 354.1425.

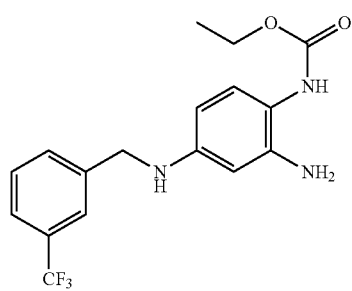

1-8

N-[2-Amino-4-({[3-(trifluoromethyl)phenyl]methyl}amino)phenyl]ethoxycarboxamide (1-8) A suspension of impure 1-27 (0.100 g, 0.193 mmol) and 10% Pd/C (0.020 g, 0.018 mmol, 10 mol %) in 1,4-dioxane (1 mL) and EtOH (0.50 mL) was allowed to stir at rt for 18 h under an H$_2$ atmosphere (balloon). The reaction mixture was diluted with Et$_2$O, filtered through a pad of Celite, and the solvent removed under reduced pressure to give crude 1-8 (0.067 g) as a dark brown oil. The crude oil was purified by chromatography on SiO$_2$ (50% EtOAc in hexanes) to give 1-8 (0.056 g, 0.16 mmol, 24% over 3 steps) as an off-white solid: Mp 103-104° C. (CH$_2$Cl$_2$); IR (ATR) 3335.08, 2987.62, 1723.51, 1679.79, 1535.27 cm$^{-1}$; $^1$H NMR (CDCl$_3$, 400 MHz) δ 7.61 (s, 1 H), 7.53 (app. t, 2 H, J=7.0 Hz), 7.46-7.42 (m, 1 H), 6.92 (d, 1 H, J=8.0 Hz), 6.05 (dd, 1 H, J=8.4, 2.4 Hz), 5.98 (d, 1 H, J=2.4 Hz), 4.34 (s, 2 H), 4.19 (q, 2 H, J=7.2 Hz), 3.76 (br s, 2 H), 1.28 (t, 3 H, J=7.2 Hz); $^{13}$C NMR (CDCl$_3$, 100 MHz) δ 155.6, 147.6, 143.2, 140.8, 131.1 (q, J=32.0 Hz), 130.7, 129.2, 128.0, 124.3 (q, J=270.9 Hz), 124.2-124.1 (overlapping q.), 114.3, 104.5, 100.8, 61.5, 48.1, 14.7; HRMS (HESI) m/z calcd for C$_{17}$H$_{19}$N$_3$O$_2$F$_3$(M+H) 354.1424, found 354.1421.

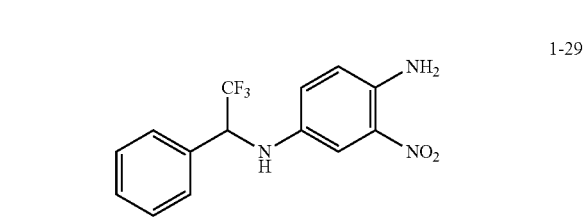

1-29

(4-Amino-3-nitrophenyl)(2,2,2-trifluoro-1-phenylethyl)amine (1-29) A solution of 2-nitro-p-phenylenediamine (0.504 g, 3.13 mmol) and PTSA (0.034 g, 0.17 mmol) in toluene (15 mL) at rt was treated with 2,2,2-trifluoroacetophenone (0.544 g, 3.09 mmol) and was stirred at reflux for 24 h with a Dean-Stark trap. The reaction mixture was filtered through a pad of SiO$_2$ and the solvent evaporated under reduced pressure to give the crude imine (0.170 g), which was suspended in 1,4-dioxane (4 mL) and MeOH (1 mL) and NaBH$_4$ (0.125 g, 3.27 mmol) was added in 3 portions at 15 minute intervals. The resulting solution was allowed to stir at rt for 3 h. H$_2$O (25 mL) was added and solution was extracted with CH$_2$Cl$_2$ (3×20 mL). The organic phase was dried (Na$_2$SO$_4$), filtered, and the solvent evaporated under reduced pressure. Further drying under high vacuum gave 1-29 (0.120 g, 0.386 mmol, 12%) as a dark red solid: Mp 126-127° C. (CH$_2$Cl$_2$); IR (ATR) 3436.04, 3387.95, 333.42, 1581.30, 1514.40, 1326.05, 1237.64; $^1$H NMR (CDCl$_3$, 400 MHz) δ 7.44-7.38 (m, 5 H), 7.33 (d, 1 H, J=2.8 Hz), 6.89 (dd, 1 H, J=9.2, 2.8 Hz), 6.69 (d, 1 H, J=8.8 Hz), 5.75 (br s, 2 H), 4.84 (m, 1 H), 4.13 (d, 1 H, J=7.6 Hz); $^{13}$C NMR (CDCl$_3$, 100 MHz) δ 139.2, 136.6, 133.6, 132.3, 129.51, 129.2, 128.0, 126.0, 125.1 (q, J=280.3 Hz), 120.3, 108.6, 61.4 (q, J=30.0 Hz); HRMS (HESI) m/z calcd for C$_{14}$H$_{13}$N$_3$O$_2$F$_3$(M+H) 312.0954, found 312.0953.

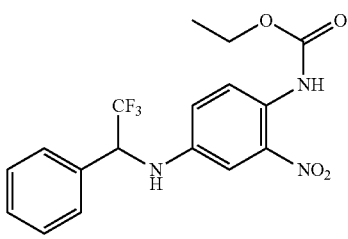

1-31

Ethoxy-N-{2-nitro-4-[(2,2,2-trifluoro-1-phenylethyl)amino]phenyl}carboxamide (1-31) A solution of 1-29 (0.060 g, 0.19 mmol) and DIPEA (0.065 mL, 0.39 mmol) in 1,4-dioxane (1.3 mL) at rt was treated dropwise via syringe with ethyl chloroformate (0.020 mL, 0.20 mmol). The resulting solution was allowed to stir at 50° C. for 18 h and was then quenched by the addition of 1:1 $H_2O:CH_2Cl_2$ (10 mL). The layers were separated and the aqueous phase was extracted with $CH_2Cl_2$ (3×10 mL). The combined organic phases were washed with $H_2O$ (2×10 mL) and brine (2×10 mL), dried ($Na_2SO_4$), filtered, and the solvent evaporated under reduced pressure to give crude 1-31 (0.100 g) as an orange-red oil. The crude solid was purified by chromatography on $SiO_2$ (40-60% $CH_2Cl_2$ in hexanes) to give 1-31 (0.054 g, 0.14 mmol, 73%) as a red oil: IR ($CH_2Cl_2$) 3372.96, 2983.93, 1718.95, 1523.09, 1324.06 $cm^{-1}$; $^1H$ NMR ($CDCl_3$, 500 MHz) δ 9.39 (s, 1 H), 8.30 (d, 1 H, J=9.0 Hz), 7.46-7.40 (m, 6 H), 6.98 (dd, 1 H, J=9.5, 2.2 Hz), 4.91 (m, 1 H), 4.56 (br d, 1 H, J=7.0 Hz), 4.22 (q, 2 H, J=7.0 Hz), 1.31 (t, 3 H, J=7.0 Hz); $^{13}C$ NMR ($CDCl_3$, 125 MHz) δ 153.6, 140.7, 137.0, 133.1, 129.6, 129.3, 128.0, 127.7, 124.9 (q, J=280.5 Hz), 122.7, 122.6, 121.5, 108.8, 61.9, 60.6 (q, J=30.4 Hz), 14.5; HRMS (HESI) m/z calcd for $C_{17}H_{17}N_3O_4F_3$ (M+H) 384.1166, found 384.1163.

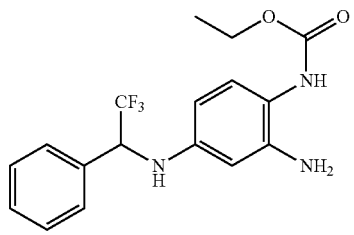

1-10

N-{2-Amino-4-[(2,2,2-trifluoro-1-phenylethyl)amino]phenyl}ethoxycarboxamide (1-10) A suspension of 1-31 (0.050 g, 0.13 mmol) and 10% Pd/C (0.014 g, 0.013 mmol) was allowed to stir under an $H_2$ atmosphere (balloon) for 18 h. The reaction mixture was diluted with $Et_2O$, filtered through Celite, and the solvent evaporated under reduced pressure to give crude 1-10 (0.066 g) as a gray oil. The crude residue was purified by chromatography on $SiO_2$ (0-10% EtOAc in $CH_2Cl_2$) to give 1-10 (0.041 g, 0.12 mmol, 89%) as a clear, colorless oil that solidified upon standing: Mp 51-52° C. ($CH_2Cl_2$); IR (ATR) 3346.05, 2984.78, 1696.03, 1524.18 $cm^{-1}$; $^1H$ NMR ($CDCl_3$, 400 MHz) δ 7.42-7.37 (m, 5 H), 6.90 (d, 1 H, J=8.0 Hz), 6.05 (app. d, 1 H, J=8.4 Hz), 6.01 (app. s, 1 H), 4.84 (m, 1 H), 4.28 (d, 1 H, J=7.2 Hz), 4.17 (q, 2 H, J=7.1 Hz), 3.72 (br s, 2 H), 1.27 (t, 3 H, J=6.6 Hz); $^{13}C$ NMR ($CDCl_3$, 100 MHz) δ 155.5, 145.3, 143.0, 134.2, 129.2, 129.0, 128.0, 125.1 (q, J=280.2 Hz), 115.5, 105.2, 102.1, 61.5, 60.7 (q, J=29.8 Hz), 14.7; HRMS (HESI) m/z calcd for $C_{17}H_{19}N_3O_2F_3$ (M+H) 354.1424, found 354.1422.

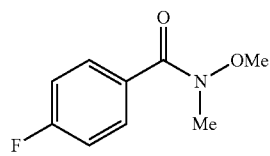

1-32

(4-Fluorophenyl)-N-methoxy-N-methylcarboxamide (1-32) $^1$A solution of methoxymethylamine hydrochloride (0.634 g, 6.37 mmol) and $Et_3N$ (0.860 mL, 6.12 mmol) in $CH_2Cl_2$ (3.75 mL) at 0° C. was treated dropwise via syringe with 4-fluorobenzoyl chloride (0.370 mL, 3.07 mmol) over 30 min and the resulting solution was allowed to stir at rt for 2 h. The reaction mixture was poured into $H_2O$ and extracted with $CH_2Cl_2$ (3×20 mL). The organic extracts were washed with brine, dried ($MgSO_4$), and the solvent removed under reduced pressure. Further drying under high vacuum gave crude 1-32 (0.672 g, 2.63 mmol, quant.) which was used without further purification: $^1H$ NMR ($CDCl_3$, 400 MHz) δ 7.74 (m, 2 H), 7.08 (m, 2 H), 3.53 (s, 3 H), 3.36 (s, 3 H); HRMS (HESI) m/z calcd for $C_9H_{11}NO_2F$ (M+H) 184.0768, found 184.0768.

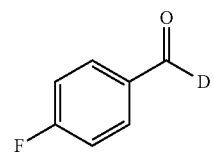

1-33

4-Fluorobenzaldehyde-d (1-33) To a solution of 1-33 (0.062 g, 0.338 mmol) in THF (1.9 mL) at −78° C. was added $LiAlD_4$ (0.018 g, 0.42 mmol) portionwise and the mixture was stirred for 2 h at the same temperature. The reaction mixture was quenched with $H_2O$ at −78° C., $Et_2O$ was added, and the precipitate removed by filtration through a pad of Celite. The filtrate was washed with $H_2O$ and brine, dried ($Na_2SO_4$), and concentrated under reduced pressure. Further drying under high vacuum for 1 h gave 0.032 g crude 1-33 as a pale yellow oil which was used without further purification.

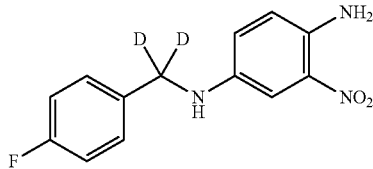

1-34

(4-Amino-3-nitrophenyl)[(4-fluorophenyl)methyl]amine-$d_2$ (1-34) A solution of 2-nitro-p-phenylenediamine (0.602 g, 3.73 mmol), PTSA (0.040 g, 0.21 mmol) and crude 1-33 (0.273 g) was heated to reflux with a Dean-Stark trap for 18 h. The solution was filtered through a thin pad of $SiO_2$ and the solvent evaporated under reduced pressure to give the crude imine (0.328 g) which was suspended in 1,4-dioxane (4 mL) and MeOH (1 mL) and $NaBD_4$ (0.111 g, 2.60 mmol) was added in 3 portions at 15 minute intervals. The resulting solution was allowed to stir at rt for 3 h and was then quenched with $H_2O$ (25 mL) and filtered to give 1-34 (0.241 g, 0.915 mmol, 42% over 2 steps) as a dark purple powder: Mp 113-114° C. ($H_2O$); IR (ATR) 3517.22, 3496.96, 3371.18, 1577.41, 1502.47, 1329.45 $cm^{-1}$; $^1H$ NMR ($CDCl_3$, 400 MHz) δ 7.34-7.27 (m, 3 H), 7.28 (d, 1 H, J=2.4 Hz), 7.03 (t, 2 H, J=8.6 Hz), 6.84 (dd, 1 H, J=8.8, 2.4 Hz), 5.75 (br s, 2 H), 3.80 (br s, 1 H); $^{13}C$ NMR ($CDCl_3$, 100 MHz) δ 162.3 (d, J=244.0 Hz), 139.4, 138.3, 134.5 (d, J=3.0 Hz), 132.5, 129.3 (d, J=8.0 Hz), 125.5, 120.2, 115.7 (d, J=21.3 Hz), 105.9, 47.7 (t, J=20.6 Hz); HRMS (HESI) m/z calcd for $C_{13}H_{11}D_2N_3O_2F$ (M+H) 264.1112, found 264.1110.

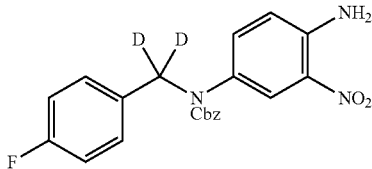

1-35

N-(4-Amino-3-nitrophenyl)-N-[(4-fluorophenyl)methyl](phenylmethoxy)carboxamide-d$_2$ (1-35) A solution of 1-34 (0.100 g, 0.380 mmol) and DIPEA (0.095 mL, 0.58 mmol) in 1,4-dioxane (1.9 mL) at rt was treated dropwise via syringe with benzyl chloroformate (0.060 mL, 0.41 mmol). The resulting solution was allowed to stir at rt for 18 h and was then quenched by the addition of 1:1 H$_2$O:CH$_2$Cl$_2$ (10 mL). The layers were separated and the aqueous phase extracted with CH$_2$Cl$_2$ (3×10 mL). The combined organic phases were washed with H$_2$O (2×10 mL) and brine (2×10 mL), dried (Na$_2$SO$_4$), filtered, and the solvent evaporated under reduced pressure to give crude 1-35 (0.220 g) as an orange-yellow oil which was used without further purification.

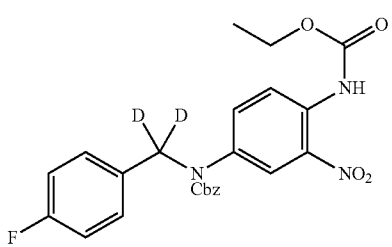

1-36

Ethoxy-N-(4-{N-[(4-fluorophenyl)methyl](phenylmethoxy)carbonylamino}-2-nitrophenyl)carboxamide-d$_2$ (1-36) A solution of crude 1-35 (0.220 g) and DIPEA (0.190 mL, 1.15 mmol) in 1,4-dioxane (3.5 mL) at rt was treated dropwise via syringe with ethyl chloroformate (0.090 mL, 0.92 mmol). The resulting solution was allowed to stir at 70° C. for 2 d and was then quenched by the addition of 1:1 H$_2$O:CH$_2$Cl$_2$ (20 mL). The layers were separated and the aqueous phase extracted with CH$_2$Cl$_2$ (2×10 mL). The combined organic phases were washed with 1 M aq. HCl (2×10 mL) and brine (2×10 mL), dried (MgSO$_4$), filtered, and the filtrate concentrated under reduced pressure. Further drying under high vacuum gave crude 1-36 (0.320 g) as an orange-yellow solid. The crude solid was purified by chromatography on SiO$_2$ (20% EtOAc in hexanes) to give 1-36 (0.100 g, 0.213 mmol, 56%) as a yellow oil: IR (CH$_2$Cl$_2$) 3364.46, 2981.47, 1738.36, 1702.40, 1509.76, 1331.36; $^1$H NMR (CDCl$_3$, 400 MHz) δ 9.77 (s, 1 H), 8.51 (d, 1 H, J=8.8 Hz), 7.99 (br s, 1 H), 7.36-7.30 (m, 4 H), 7.27-7.25 (m, 2 H), 7.17-7.13 (m, 2 H), 6.96 (tt, 2 H, J=8.6, 2.3 Hz), 5.19 (s, 2 H), 4.26 (q, 2 H, J=7.0 Hz), 1.34 (t, 3 H, J=7.0 Hz); $^{13}$C NMR (CDCl$_3$, 100 MHz) δ 162.4 (d, J=245.0 Hz), 155.2, 153.1, 136.0, 135.7, 134.7, 134.0, 132.6 (d, J=3.2 Hz), 129.7, 128.7, 128.4, 128.1, 123.9, 121.1, 115.7 (d, J=21.3 Hz), 68.1, 62.2, 52.8 (br), 14.5; HRMS (HESI) m/z calcd for $C_{24}H_{19}D_2N_3O_6F$ (M−H) 468.1534, found 468.1545.

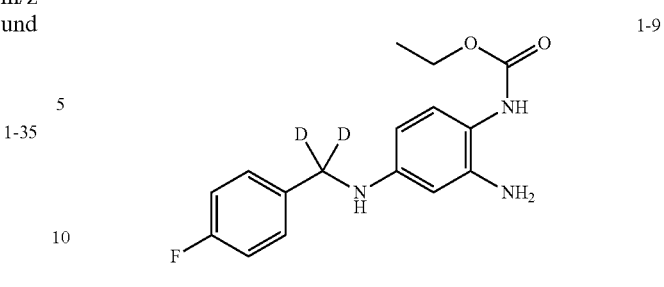

1-9

N-(2-Amino-4-{[(4-fluorophenyl)methyl]amino}phenyl)ethoxycarboxamide-d$_2$ (1-9) A suspension of 1-36 (0.095 g, 0.196 mmol) and 10% Pd/C (0.022 g, 0.020 mmol) in 1,4-dioxane (1.1 mL) and EtOH (0.60 mL) was allowed to stir at rt under an H$_2$ atmosphere (balloon) for 18 h. The solution was diluted with Et$_2$O (5 mL), filtered through a pad of Celite, and the solvent evaporated under reduced pressure to give crude 1-9 (0.078 g) as a light brown oil. The crude residue was purified by chromatography on SiO$_2$ (55% EtOAc in hexanes) to give 1-9 (0.045 g, 0.147 mmol, 75%) as a light brown solid: Mp 142-143° C. (CH$_2$Cl$_2$); IR (ATR) 3394.70, 3342.61, 2987.36, 1675.57, 1506.24 cm$^{-1}$; $^1$H NMR (CDCl$_3$, 400 MHz) δ 7.32-7.28 (m, 2 H), 7.01 (app. t, 2 H, J=8.6 Hz), 6.91 (d, 1 H, J=8.4 Hz), 6.04 (dd, 1 H, J=8.4, 2.4 Hz), 5.98 (d, 1 H, J=2.4 Hz), 4.18 (q, 2 H, J=7.0 Hz), 3.78 (br s, 2 H), 1.28 (t, 3 H, J=7.0 Hz); $^{13}$C NMR (CDCl$_3$, 100 MHz) 162.1 (d, J=243.0 Hz), 155.7, 147.8, 143.1, 135.1 (d, J=3.0 Hz), 129.0 (d, J=8.0 Hz), 128.0, 115.5 (d, J=21.2 Hz), 114.1, 104.4, 100.8, 61.5, 47.1 (t, J=20.6 Hz), 14.7; HRMS (HESI) m/z calcd for $C_{16}H_{17}D_2N_3O_2F$ (M+H) 306.1581, found 306.1584.

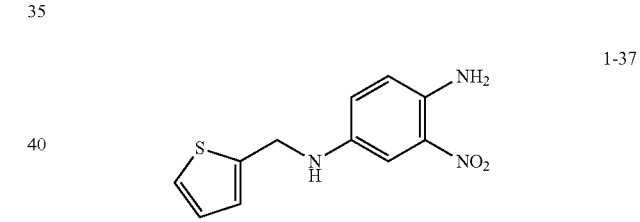

1-37

(4-Amino-3-nitrophenyl)(2-thienylmethyl)amine (1-37) A solution of thiophene-2-carboxaldehyde (0.125 mL, 1.34 mmol), 2-nitro-p-phenylenediamine (0.210 g, 1.30 mmol), PTSA (0.035 g, 0.18 mmol), and 4 Å mol. sieves (1.063 g) in CH$_2$Cl$_2$ (3.1 mL) and MeOH (3.1 mL) was allowed to stir at rt for 5 h. The resulting solution was filtered through Celite and the solvent removed under reduced pressure to give a dark brown solid that was dissolved in CH$_2$Cl$_2$ (20 mL), filtered through a thin pad of SiO$_2$ eluting with the same solvent, and concentrated under reduced pressure to give crude imine (0.250 g) as a bright orange solid. The solid was suspended in 1,4-dioxane (1.5 mL) and MeOH (0.50 mL), NaBH$_4$ (0.070 g, 1.83 mmol was added in 3 portions at 15 min intervals, and the resulting solution was allowed to stir at rt for 20 h. The reaction mixture was quenched by the addition of 1:1 H$_2$O:CH$_2$Cl$_2$ (30 mL). The layers were separated and the aqueous layer was extracted with CH$_2$Cl$_2$ (3×10 mL). The combined organic layers were washed with H$_2$O (2×10 mL) and brine (2×10 mL), dried (Na$_2$SO$_4$), filtered, and the solvent evaporated under reduced pressure. Further drying under high vacuum at 50° C. gave 1-37 (0.230 g, 0.923 mmol, 71%) as a dark red solid: Mp 103-105° C. (CH$_2$Cl$_2$); IR (ATR) 3506.46, 3380.50, 3115.96, 1576.61, 1518.86, 1332.92 cm$^{-1}$; $^1$H NMR (CDCl$_3$, 400 MHz) δ 7.37 (d, 1 H, J=2.8 Hz), 7.23 (dd, 1 H, J=4.8, 1.2 Hz), 7.03-7.02 (m, 1 H), 6.97 (dd, 1 H, J=5.2, 3.6 Hz), 6.88 (dd, 1 H, J=8.8, 2.8 Hz), 6.71 (d, 1 H, J=8.8 Hz), 5.74 (br s, 2 H), 4.48 (s, 2 H), 3.83 (br s, 2 H); $^{13}$C NMR (CDCl$_3$, 100 MHz) δ 142.2, 139.0, 138.5, 132.6, 127.1, 125.6, 125.6, 125.0, 120.2, 106.6, 44.2; HRMS (HESI) m/z calcd for C$_{11}$H$_{12}$N$_3$O$_2$S (M+H) 250.0645, found 250.0644.

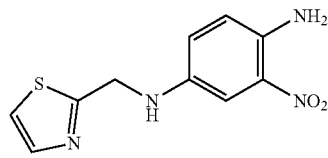

1-39

(4-Amino-3-nitrophenyl)(1,3-thiazol-2-ylmethyl)amine (1-39) A solution of 2-thiazolecarboxaldehyde (0.115 mL, 1.27 mmol), 2-nitro-p-phenylenediamine (0.209 g, 1.30 mmol), PTSA (0.025 g, 0.13 mmol), and 4 Å mol. sieves (1.15 g) in CH$_2$Cl$_2$ (3.1 mL) and MeOH (3.1 mL) was allowed to stir for 18 h at rt. The resulting solution was filtered through Celite and the solvent removed under reduced pressure to give a dark brown solid. This solid was suspended in CH$_2$Cl$_2$ (20 mL), filtered through a thin pad of SiO$_2$ eluting with the same solvent, and the solvent removed under reduced pressure to give crude imine (0.205 g) as a bright orange solid. The solid was suspended in 1,4-dioxane (2 mL) and MeOH (0.75 mL), NaBH$_4$ (0.035 g, 0.92 mmol) was added in a single portion, and the resulting solution was allowed to stir at rt for 8 h. The reaction mixture was quenched by the addition of 1:1 H$_2$O:CH$_2$Cl$_2$ (15 mL). The layers were separated and the aqueous layer was extracted with CH$_2$Cl$_2$ (3×10 mL). The combined organic layers were washed with H$_2$O (2×10 mL) and brine (2×10 mL), dried (Na$_2$SO$_4$), filtered, and the solvent evaporated under reduced pressure. Further drying under high vacuum at 50° C. overnight gave 1-39 (0.194 g, 0.775 mmol, 61%) as a dark red solid: Mp 161-162° C. (CH$_2$Cl$_2$); IR (ATR) 3469.82, 3380.19, 3349.79, 1584.11, 1518.80, 1384.29, 1330.62 cm$^{-1}$; $^1$H NMR (DMSO-d$_6$, 500 MHz) δ 7.74 (d, 1 H, J=3.0 Hz), 7.58 (d, 1 H, J=3.0 Hz), 7.04 (br s, 2 H), 7.02 (d, 1 H, J=3.0 Hz), 6.99 (d, 1 H, J=2.5 Hz), 6.90 (d, 1 H, J=9.0 Hz), 6.39 (t, 1 H, J=6.0 Hz), 4.54 (d, 2 H, J=6.0 Hz); $^{13}$C NMR (DMSO-d$_6$, 125 MHz) δ 171.8, 142.4, 140.1, 138.2, 129.9, 126.5, 120.4, 119.9, 103.0, 45.6; HRMS (HESI) m/z calcd for C$_{10}$H$_{11}$N$_4$O$_2$S (M+H) 251.0597, found 251.0595.

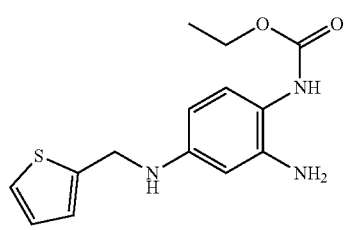

1-11

N-{2-Amino-4-[(2-thienylmethyl)amino]phenyl}ethoxycarboxamide (1-11) A suspension of 1-37 (0.104 g, 0.334 mmol, 80% purity) and 10% Pd/C (0.035 g, 0.032 mmol) in 1,4-dioxane (1.7 mL) and EtOH (0.70 mL) was allowed to stir at rt for 16 h under an H$_2$ atmosphere. The reaction mixture was diluted with Et$_2$O, filtered through a pad of Celite, and the solvent evaporated under reduced pressure. Further drying under high vacuum gave the crude aryl triamine (0.093 g) as a dark yellow oil. A solution of crude aryl triamine (0.093 g) and Et$_3$N (0.080 mL, 0.57 mmol) in CH$_2$Cl$_2$ (1.2 mL) at rt was treated dropwise via syringe over 15 min with a solution of 1-41 (0.050 g, 0.21 mmol) in CH$_2$Cl$_2$ (1.2 mL). The resulting solution was allowed to stir at rt for 18 h, the solvent was evaporated under reduced pressure, the crude residue dissolved in EtOAc (20 mL), and washed with sat. aq. NaHCO$_3$ (5×10 mL). The aqueous washes were extracted with EtOAc (2×20 mL) and the combined organic phases were dried (MgSO$_4$), filtered, and the solvent evaporated under reduced pressure to give crude 1-11 (0.200 g) as a brown-green oil. The crude residue was purified by chromatography on SiO$_2$ (5-10% EtOAc in CH$_2$Cl$_2$) to give 1-11 (0.037 g, 0.13 mmol, 60%) as a gray oil that solidified upon standing: Mp 95-96° C. (CH$_2$Cl$_2$); IR (ATR) 3403.37, 3287.93, 1677.01, 1518.63 cm$^{-1}$; $^1$H NMR (CDCl$_3$, 500 MHz) δ 7.20 (dd, 1 H, J=5.0, 1.5 Hz), 6.99 (app. d, 1 H, J=2.5 Hz), 6.96 (dd, 1 H, J=5.0, 3.5 Hz), 6.93 (d, 1 H, J=8.5 Hz), 6.09 (dd, 1 H, J=8.3, 2.5 Hz), 6.04 (d, 1 H, J=2.5 Hz), 4.44 (s, 2 H), 4.19 (q, 2 H, J=7.0 Hz), 3.82 (br s, 3 H), 1.28 (t, 3 H, J=6.5 Hz); $^{13}$C NMR (CDCl$_3$, 125 MHz) δ 155.6, 147.4, 143.1, 127.8, 127.0, 125.1, 124.7, 114.5, 104.7, 101.2, 61.5, 43.7, 14.7; HRMS (HESI) m/z calcd for C$_{14}$H$_{18}$N$_3$O$_2$S (M+H) 292.1120, found 292.1109.

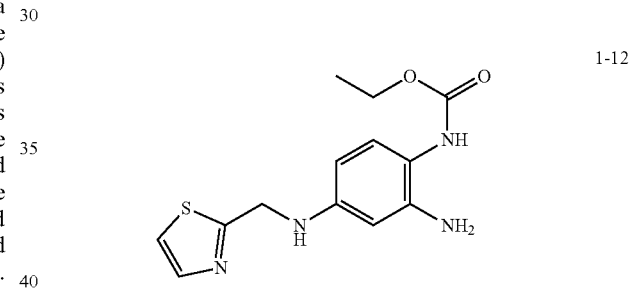

1-12

N-{2-Amino-4-[(1,3-thiazol-2-ylmethyl)amino]phenyl}ethoxycarboxamide (1-12) A suspension of 1-39 (0.072 g, 0.29 mmol) and Pd/C (0.028 g, 0.026 mmol) was allowed to stir under an H$_2$ atmosphere (balloon) for 18 h. The reaction mixture was diluted with Et$_2$O (10 mL) and filtered through a pad of Celite. The solvent was removed under reduced pressure to give the crude aryl triamine (0.076 g) as a dark red oil which was used without further purification. A solution of the crude aryl triamine (0.076 g) and Et$_3$N (0.075 mL, 0.53 mmol) in CH$_2$Cl$_2$ (1.00 mL) at rt was treated dropwise via syringe over 10 min with a solution of 1-41 (0.061 g, 0.26 mmol) in CH$_2$Cl$_2$ (1.10 mL). The resulting solution was allowed to stir for 18 h, the solvent was evaporated under reduced pressure, the crude residue dissolved in EtOAc (20 mL), and washed with sat. aq. NaHCO$_3$ (4×20 mL) until the washes were clear. The aqueous washes were extracted with EtOAc (2×20 mL) and the combined organic fractions were washed with H$_2$O (2×20 mL) and brine (2×20 mL), dried (MgSO$_4$), filtered, and the solvent evaporated under reduced pressure to give crude 1-12 (0.060 g) as a brown-red oil. The crude residue was purified by chromatography on SiO$_2$ (70% EtOAc in hexanes) to give 1-12 (0.045 g, 0.15 mmol, 59% over 2 steps) as a blue-green oil that solidified upon standing: Mp 46-47° C. (CH$_2$Cl$_2$); IR (CH$_2$Cl$_2$) 3352.87, 2981.33, 1696.90, 1621.12, 1523.21 cm$^{-1}$; $^1$H NMR (CDCl$_3$, 400

MHz) δ 7.72 (d, 1 H, J=3.2 Hz), 7.24 (d, 1 H, J=3.2 Hz), 6.91 (d, 1 H, J=8.4 Hz), 6.16 (br s, 1 H), 6.08 (dd, 1 H, J=8.4, 2.4 Hz), 6.02 (d, 1 H, J=2.4 Hz), 4.59 (s, 2 H), 4.17 (q, 2 H, J=7.2 Hz), 3.81 (br s, 2 H), 1.27 (t, 3H, J=6.8 Hz); $^{13}$C NMR (CDCl$_3$, 400 MHz) δ 171.6, 155.7, 146.8, 143.1, 142.7, 127.9, 119.2, 114.8, 104.7, 101.2, 61.5, 46.5, 14.7; HRMS (HESI) m/z calcd for C$_{13}$H$_{17}$N$_4$O$_2$S (M+H) 293.1067, found 293.1063.

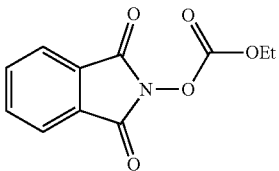

1-41

Ethyl (1,3-dioxobenzo[c]azolidin-2-yloxy)formate (1-41) $^{113}$A suspension of diphthalimidyl carbonate (0.382 g, 1.08 mmol) and EtOH (0.065 mL, 1.1 mmol) in THF (2.5 mL) was treated with Et$_3$N (0.150 mL, 1.07 mmol). Upon addition of base, the suspension turned yellow progressing to orange over 30 min. The reaction mixture was stirred for 5 h and the solvent evaporated. The residue was dissolved in EtOAc (25 mL) and washed with sat. aq. NaHCO$_3$ (5×10 mL) until the organic layer became clear. The combined aqueous washings were extracted with EtOAc (2×20 mL). The combined organic layers were dried (MgSO$_4$), filtered, and the solvent evaporated under reduced pressure. Further drying under high vacuum gave 1-41 (0.230 g, 0.978 mmol, 90%) as a light yellow solid: $^1$H NMR (CDCl$_3$, 300 MHz) δ 7.90-7.84 (m, 2 H), 7.81-7.76 (m, 2 H), 4.40 (q, 2 H, J=7.2 Hz), 1.40 (t, 3 H, J=7.2 Hz); $^{13}$C NMR (CDCl$_3$, 75 MHz) δ 161.6, 152.4, 135.0, 128.8, 124.1, 67.7, 14.1.

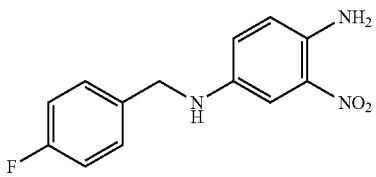

1-2

(4-Amino-3-nitrophenyl)[(4-fluorophenyl)methyl]amine (1-2) A solution of 2-nitro-p-phenylenediamine (0.998 g, 6.19 mmol) and 3 Å mol. sieves (3.00 g) in xylenes (30 mL) was heated to 90° C. and treated with 4-fluorobenzaldehyde (0.690 mL, 6.27 mmol). The resulting solution was allowed to stir for 20 h, filtered through a short pad of SiO$_2$, allowed to cool for 6 h, and the solid precipitate filtered off to give the crude imine (0.719 g), that was dissolved in 1,4-dioxane (4 mL) and MeOH (1 mL) and NaBH$_4$ (0.157 g, 4.11 mmol) was added in 3 batches at 15 min intervals. The solution was stirred for 10 h, quenched with H$_2$O (25 mL), and the solid filtered to give 1-2 (0.573 g, 2.19 mmol, 35%): Mp 113-114° C.; IR (ATR) 3517.98, 3497.88, 3395.77, 3372.60, 1578.67, 1503.24, 1406.73, 1329.96 cm$^{-1}$; $^1$H NMR (CDCl$_3$, 400 MHz) δ 7.33 (app. dd, 2 H, J=5.4, 2.2 Hz), 7.30 (d, 1 H, J=2.8 Hz), 7.04 (app. t, 2 H, J=8.6 Hz), 6.84 (dd, 1 H, J=8.8, 2.8 Hz), 6.70 (d, 1 H, J=8.8 Hz), 5.73 (br s, 2 H), 4.26 (d, 2 H, J=4.0 Hz); $^{13}$C NMR (CDCl$_3$, 100 MHz) δ 162.3 (d, J=245.0 Hz), 139.4, 138.3, 134.6 (d, J=2.9 Hz), 132.6, 129.4 (d, J=8.0 Hz), 125.4, 120.2, 115.7 (d, J=22.0 Hz), 106.1, 48.4; HRMS (HESI) m/z calcd for C$_{13}$H$_{13}$N$_3$O$_2$F (M+H) 262.0986, found 262.0981.

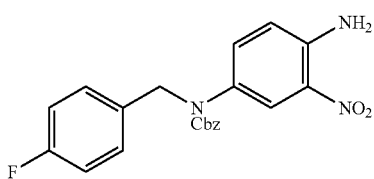

1-42

N-(4-Amino-3-nitrophenyl)-N-[(4fluorophenyl)methyl](phenylmethoxy)carboxamide (1-42) A solution of 1-2 (0.207 g, 0.792 mmol) and DIPEA (0.140 mL, 0.848 mmol) in 1,4-dioxane (4 mL) at rt was treated dropwise via syringe with benzyl chloroformate (0.120 mL, 0.819 mmol). The resulting solution was allowed to stir at rt for 5 h and was then quenched with 1:1 H$_2$O:CH$_2$Cl$_2$ (6.5 mL). The phases were separated and the aqueous phase extracted with CH$_2$Cl$_2$ (3×5 mL). The combined organic phases were washed with brine, dried (Na$_2$SO$_4$), filtered, and the solvent evaporated under reduced pressure to give crude 1-42 (0.420 g) as an orange oil which was used without further purification.

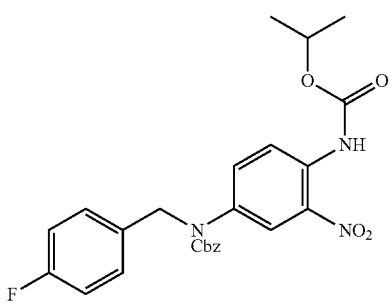

1-43

N-(4-{N-[(4-Fluorophenyl)methyl](phenylmethoxy)carbonylamino}-2-nitrophenyl) (methylethoxy)carboxamide (1-43) A solution of crude 1-42 (0.415 g) and DIPEA (0.390 mL, 2.36 mmol) in 1,4-dioxane (6.00 mL) at rt was treated dropwise via syringe with a solution of isopropyl chloroformate in toluene (1.95 mL, 1.95 mmol, 1.0 M). The resulting solution was allowed to stir at 70° C. for 2 d and was then quenched by the addition of 1:1 H$_2$O: CH$_2$Cl$_2$ (10 mL), the layers were separated, and the aqueous phase extracted with CH$_2$Cl$_2$ (3×10 mL). The combined organic phases were washed with water and brine, dried (MgSO$_4$), filtered, and concentrated under reduced pressure to give crude 1-43 (0.410 g) as a dark orange oil. The crude oil was purified by chromatography on SiO$_2$ (10% EtOAc in hexanes) to give 1-43 (0.097 g) as a yellow oil along with recovered starting material (0.140 g). The starting material was recycled through the reaction procedure again to give 1-43 (0.050 g, 0.147 g total, 0.305 mmol, 39% over two steps) as a yellow oil: IR (CH$_2$Cl$_2$) 3367.42, 2982.20, 1735.01, 1705.36, 1510.64, 1338.30 cm$^{-1}$; $^1$H NMR (CDCl$_3$, 400 MHz) δ 9.72 (s, 1 H), 8.52 (d, 1 H, J=8.8 Hz), 7.98 (br s, 1 H), 7.36-7.25 (m, 5 H), 7.15 (app. t, 2 H, J=6.8 Hz), 6.96 (t, 2 H, J=8.8 Hz), 5.19 (s, 2 H), 5.08-4.96 (m, 2 H), 4.84 (s, 2 H), 1.32 (d, 6 H, J=6.4 Hz); $^{13}$C NMR (CDCl$_3$, 100 MHz) δ 162.4 (d, J=245.0 Hz), 155.3, 152.8, 136.0, 135.7, 134.7, 134.2, 132.8 (d, J=3.2 Hz), 129.8, 128.7, 128.4, 128.1, 124.0, 121.1, 115.8 (d, J=21.3 Hz); HRMS (HESI) m/z calcd for $C_{25}H_{24}N_3O_6F$ (M−H) 480.1565, found 480.1575.

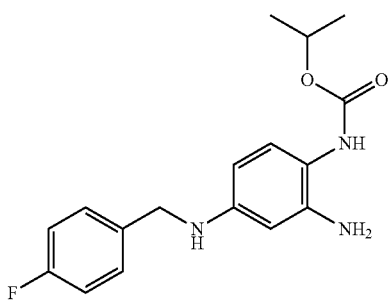

1-44

N-(2-Amino-4-{[(4-fluorophenyl)methyl]amino}phenyl) (methylethoxy)carboxamide (1-44) A suspension of 1-43 (0.049 g, 0.10 mmol) and 10% Pd/C (0.013 g, 0.012 mmol, 10 mol %) in 1,4-dioxane (0.60 mL) and EtOH (0.30 mL) was allowed to stir at rt for 18 h under an $H_2$ atmosphere (balloon). The reaction mixture was diluted with $Et_2O$ (5 mL), filtered through Celite, and the solvent evaporated under reduced pressure to give crude 1-43 (0.033 g) as a brown oil. The crude oil was purified by chromatography on $SiO_2$ (50% EtOAc in hexanes) to give 1-43 (0.024 g, 0.076 mmol, 74%) as an off-white solid: Mp 171-172° C. ($CH_2Cl_2$); IR (ATR) 3396.44, 3342.93, 3289.29, 2981.70, 1674.75; $^1$H NMR ($CDCl_3$, 400 MHz) δ 7.31 (app. dd, 2 H, J=8.4, 5.6 Hz), 7.01 (app. t, 2 H, J=10.2 Hz), 6.92 (d, 1 H, J=8.0 Hz), 6.06 (dd, 1 H, J=8.4, 2.4 Hz), 6.00 (d, 1 H, J=2.4 Hz), 4.97 (m, 1 H), 4.25 (s, 2 H), 3.81 (br s, 2 H), 1.27 (d, 6 H, J=6.4 Hz); 13C NMR ($CDCl_3$, 100 MHz) δ 162.2 (d, J=244.0 Hz), 155.3, 147.7, 143.1, 135.3 (d, J=2.9 Hz), 129.1 (d, J=7.9 Hz), 127.8, 115.6 (d, J=21.2 Hz), 114.4, 104.5, 100.8, 68.9, 47.8, 22.3; HRMS (HESI) m/z calcd for $C_{17}H_{21}N_3O_2F$ (M−H) 318.1612, found 318.1611.

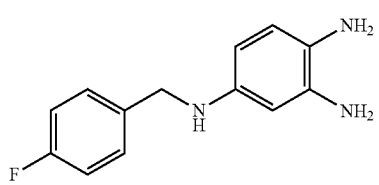

1-45

(3,4-Diaminophenyl)[(4-fluorophenyl)methyl]amine (1-45) A suspension of 1-2 (0.101 g, 0.321 mmol) and 10% Pd/C (0.035 g, 0.032 mmol) in 1,4-dioxane (1.6 mL) and EtOH (0.80 mL) was allowed to stir at rt under an $H_2$ atmosphere (balloon) for 18 h. The reaction mixture was diluted with $Et_2O$ (10 mL), filtered through a pad of celite, and the solvent evaporated under reduced pressure. Further drying under high vacuum gave crude 1-45 (0.077 g) as a brown oil which was used without further purification.

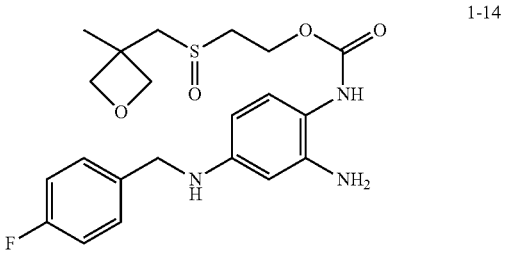

1-14

N-(2-Amino-4-{[(4-fluorophenyl)methyl]amino}phenyl) {2-[(3-methyloxetan-3-yl)sulfinyl]ethoxy}carboxamide (1-14) A solution of crude 1-45 (0.062 g, 0.27 mmol) and $Et_3N$ (0.070 mL, 0.50 mmol) in $CH_2Cl_2$ (1.00 mL) was treated dropwise via syringe over 10 min with a solution of crude 1-47 (0.095 g, 0.26 mmol) in $CH_2Cl_2$ (1.00 mL). The resulting solution was allowed to stir for 18 h at rt, the solvent was evaporated under reduced pressure, the residue dissolved in EtOAc (20 mL), and washed with sat. aq. $NaHCO_3$ (3×10 mL). The combined aqueous layers were extracted with EtOAc (2×20 mL) and the combined organic layers were dried ($MgSO_4$), filtered, and the solvent evaporated under reduced pressure to give crude 1-14 (0.090 g) as a dark green oil. The crude residue was purified by chromatography on $SiO_2$ (3-5% MeOH in $CH_2Cl_2$) to give 1-14 (0.041 g, 0.094 mmol, 39% over two steps) as a light brown oil: IR ($CH_2Cl_2$) 3362.88, 2256.98, 1712.79, 1619.15, 1525.30, 1508.32 cm$^{-1}$; $^1$H NMR (DMSO-$d_6$, 500 MHz, 323 K) δ 7.99 (br s, 1 H), 7.38-7.35 (m, 2 H), 7.09 (t, 2 H, J=8.8 Hz), 6.73 (d, 1 H, J=8.5 Hz), 5.99 (d, 1 H, J=2.0 Hz), 5.88 (dd, 1 H, J=8.5, 2.5 Hz), 5.56 (s, 1 H), 4.64 (d, 1 H, J=5.5 Hz), 4.55 (d, 1 H, J=5.5 Hz), 4.45-4.31 (m, 5 H), 4.24 (d, 1 H, J=6.0 Hz), 4.19 (d, 2 H, J=4.5 Hz), 3.19-3.13 (m, 2 H), 3.03-3.00 (m, 2 H), 1.49 (s, 3 H); $^{13}$C NMR (DMSO-$d_6$, 125 MHz, 323 K) δ 160.7 (d, J=240.0 Hz), 154.2, 147.1, 143.2, 136.4, 128.5 (d, J=7.5 Hz), 126.9, 114.3 (d, J=21.3 Hz), 112.7, 101.7, 98.9, 90.0, 80.6, 59.8, 56.7, 51.7, 45.9, 37.6, 23.0; HRMS (HESI) m/z calcd for $C_{21}H_{27}N_3O_4FS$ (M+H) 436.1701, found 436.1698.

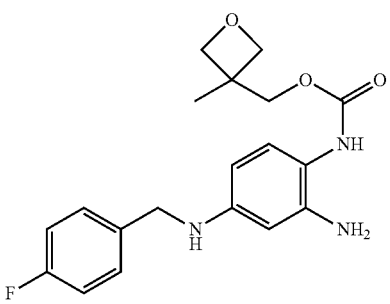

1-15

N-(2-Amino-4-{[(4-fluorophenyl)methyl]amino}phenyl) [(3-methyloxetan-3-yl)methoxy]carboxamide (1-15) A solution of crude 1-45 (0.077 g) and $Et_3N$ (0.090 mL, 0.64 mmol) in $CH_2Cl_2$ (1.30 mL) at rt was treated dropwise via syringe over 15 min with a solution of 1-46 (0.101 g, 0.347 mmol) in $CH_2Cl_2$ (1.30 mL). The resulting solution was allowed to stir for 18 h, the solvent was evaporated under reduced pressure, the crude residue dissolved in EtOAc (20 mL), and washed with sat. aq. $NaHCO_3$ (3×10 mL). The combined aqueous washes were extracted with EtOAc (2×20 mL) and the combined organic layers were dried (MgSO$_4$), filtered, and the solvent evaporated under reduced pressure to give crude 1-15 (0.110 g) as an olive green oil. The crude oil was purified by chromatography on SiO$_2$ (40-50% EtOAc in hexanes) to give 1-15 (0.033 g, 0.092 mmol, 29% over 2 steps) as a dark brown oil; IR (CH$_2$Cl$_2$) 3346.52, 2960.42, 2876.96, 1701.71, 1619.50, 1524.48, 1508.10 cm$^{-1}$; $^1$H NMR (CDCl$_3$, 400 MHz) δ 7.30 (dd, 2 H, J=8.2, 5.4 Hz), 7.02 (app. t, 2 H, J=8.6 Hz), 6.93 (d, 1 H, J=7.6 Hz), 6.21 (br s, 1 H), 6.06 (d, 1 H, J=8.4 Hz), 6.00 (s, 1 H), 4.58 (app. br s, 2 H), 4.39 (app. br s, 2 H), 4.25 (s, 2 H), 4.20 (s, 2 H), 3.80 (br s, 3 H), 1.35 (s, 3 H); $^{13}$C NMR (CDCl$_3$, 100 MHz) δ 161.2 (d, J=243.0 Hz), 155.5, 147.9, 143.1, 135.2 (d, J=3.0 Hz), 129.0 (d, J=8.0 Hz), 127.9, 115.6 (d, J=21.0 Hz), 113.9, 104.6, 100.8, 79.6, 69.4, 47.7, 39.5, 21.3; HRMS (HESI) m/z calcd for C$_{19}$H$_{23}$N$_3$O$_3$F (M+H) 360.1723, found 360.1712.

1-46

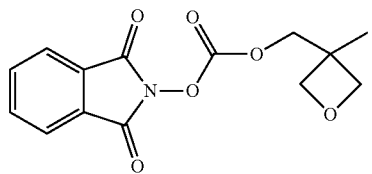

(3-Methyloxetan-3-yl)methyl (1,3-dioxobenzo[c]azolidin-2-yloxy)formate (1-46) A suspension of diphthalimidyl carbonate (0.381 g, 1.08 mmol) and 3-methyl-3-oxetanemethanol (0.110 mL, 1.08 mmol) in THF (5 mL) was treated with Et$_3$N (0.160 mL, 1.14 mmol). Upon addition of base, the suspension turned yellow progressing to orange over 2 h. The reaction mixture was stirred for 14 h and the solvent was evaporated under reduced pressure. The residue was dissolved in EtOAc (25 mL) and washed with sat. aq. NaHCO$_3$ (5×10 mL) until the organic layer became clear. The combined aqueous washings were extracted with EtOAc (2×20 mL). The combined organic layers were dried (MgSO$_4$), filtered, and the solvent evaporated under reduced pressure. Further drying under high vacuum gave 1-46 (0.255 g, 0.876 mmol, 81%) as a clear, light yellow oil: IR (CH$_2$Cl$_2$) 2965.43, 2875.74, 1811.79, 1788.73, 1741.98 cm$^{-1}$; $^1$H NMR (CDCl$_3$, 400 MHz) δ 7.91-7.88 (m, 2 H), 7.81-7.79 (m, 2 H), 4.54 (d, 2 H, J=6.4 Hz), 4.47 (s, 2 H), 4.43 (d, 2 H, J=6.0 Hz), 1.41 (s, 3 H); $^{13}$C NMR (CDCl$_3$, 100 MHz) 161.5, 152.7, 135.1, 128.8, 124.3, 79.1, 75.4, 39.5, 20.8; HRMS (HESI) m/z calcd for C$_{14}$H$_{14}$NO$_6$ (M+H) 292.0816, found 292.0819.

1-47

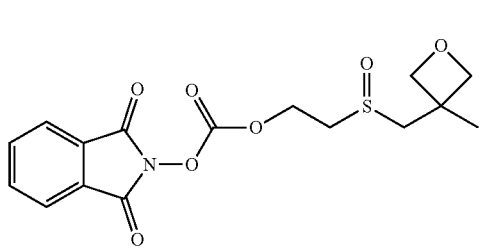

2-{[(3-Methyloxetan-3-yl)methyl]sulfinyl}ethyl (1,3-dioxobenzo[c]azolidin-2-yloxy)formate (1-47) $^2$A suspension of diphthalimidyl carbonate (0.380 g, 1.08 mmol) and MMS-350 sulfoxide alcohol (0.195 g, 1.09 mmol) in THF (5 mL) was treated with Et$_3$N (0.145 mL, 1.03 mmol). Upon addition of base, the suspension turned yellow, eventually progressing to a clear orange solution after 20 min. The reaction mixture was stirred 2 h, and the solvent was evaporated. The residue was dissolved in EtOAc (25 mL) and washed with saturated aqueous NaHCO$_3$ (5×3 mL) until the organic layer became clear. The combined aqueous washings were extracted with EtOAc (2×10 mL). The combined organics were dried (MgSO$_4$) and the solvent evaporated under reduced pressure to give 1-47 (0.265 g, 0.721 mmol, 66%) as a foaming solid which was used without further purification.

Scheme 1. Synthetic route to tinnitus compounds

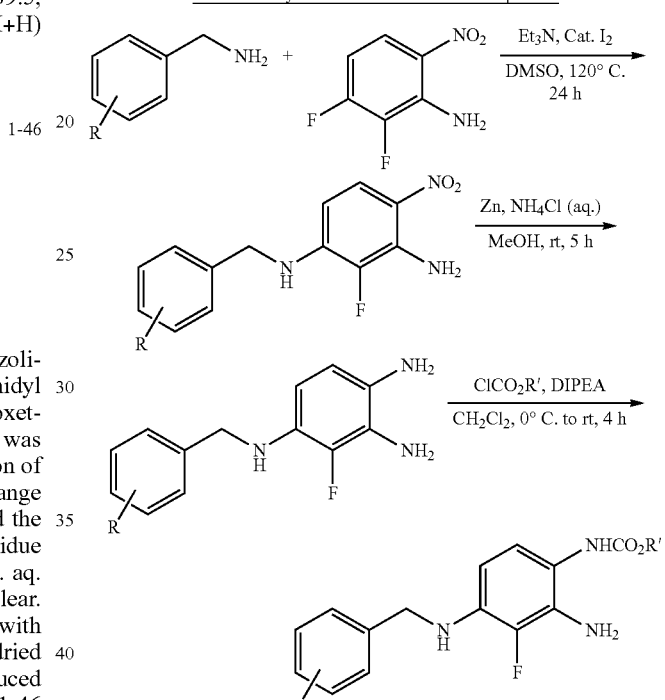

Experimental Part:

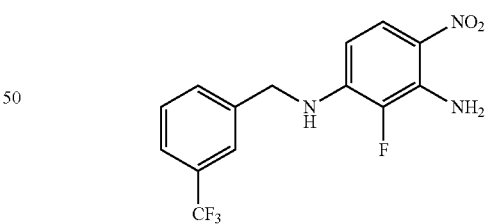

2-fluoro-4-nitro-N1-(3-(trifluoromethyl)benzyl)benzene-1,3-diamine To a stirred solution of 2,3-difluoro-6-nitroaniline (0.200 g, 1.11 mmol, 1.00 equiv) in dry DMSO (4.6 mL) were added 3-(trifluoromethyl)benzylamine (0.195 mL, 1.34 mmol, 1.2 equiv) followed by Et$_3$N (0.135 g, 1.34 mmol, 1.2 equiv) and I$_2$ (cat. 2 mg). The reaction mixture was heated to 120° C. for 24 h. The reaction mixture was cooled to room temperature, diluted with water (25 mL) and extracted with EtOAc (3×15 mL). The separated organic layer was washed with brine, dried over Na$_2$SO$_4$, filtered and concentrated under reduced pressure. The residue was purified by flash column chromatography on silica gel (EtOAc/Hexanes=1:10 to 1:4 to 1:3) to afford the product as a yellow solid (0.280 g, 76%). 1H NMR (400 MHz, CDCl$_3$) δ 7.86 (dd, J=9.6, 1.6 Hz, 1 H), 7.59-7.57 (m, 2 H), 7.54-7.47 (m, 2 H), 6.15-6.00 (m, 3 H), 4.93 (br, 1 H), 4.54 (d, J=6.0 Hz, 2 H); 13C NMR (100 MHz, CDCl$_3$) δ 140.86 (d, J=9.5 Hz), 138.89, 138.03 (d, J=228.6 Hz), 135.21 (d, J=12.9 Hz), 131.51 (q, J=32.5 Hz), 130.48, 129.63, 125.62 (d, J=3.5 Hz), 124.89 (q, J=3.7 Hz), 124.05 (q, J=272.4 Hz), 123.99 (q, J=3.7 Hz), 123.66 (d, J=2.9 Hz), 100.71 (d, J=2.9 Hz), 46.75; 19F NMR (471 MHz, CDCl$_3$) δ −62.65, −160.62; IR (neat) 3495.2, 3383.4, 1627.4, 1480.1, 1411.1, 1275.1, 1250.8, 1120.3, 1070.0, 797.8 cm-1; HRMS (ESI) m/z calcd for C$_{14}$H$_{12}$N$_3$O$_2$F$_4$ [M+H]+ 330.0860, found 330.0858.

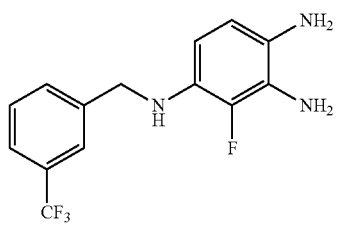

3-fluoro-N4-(3-(trifluoromethyl)benzyl)benzene-1,2,4-triamine To a stirred solution of 2-fluoro-4-nitro-N1-(3-(trifluoromethyl)benzyl)benzene-1,3-diamine (0.280 g, 0.85 mmol) in MeOH (2 mL) was added zinc powder (0.278 g, 4.25 mmol) followed by sat. ammonium chloride solution (0.80 mL) dropwise. After being stirred vigorously at room temperature overnight, the reaction mixture was diluted with EtOAc (2 mL) and water (1 mL) filtered through celite, the filter cake was washed with EtOAc. The filter was extracted with EtOAc (3×5 mL), the combined organic layer was dried over Na$_2$SO$_4$, concentrated to afford the desired product as a dark red solid (0.190 g, 75%). Used in the next step without further purification. 1H NMR (400 MHz, CDCl$_3$) δ 7.63 (s, 1 H), 7.56 (d, J=7.6 Hz, 1 H), 7.52 (d, J=7.6 Hz, 1 H), 7.44 (t, J=7.6 Hz, 1 H), 6.37 (dd, J=8.4, 2.0 Hz, 1 H), 5.99 (t, J=8.8 Hz, 1 H), 4.36 (s, 2 H), 3.98 (br, 1 H), 3.52 (br, 2 H), 3.10 (br, 2 H). 19F NMR (471 MHz, CDCl$_3$) δ −62.54, −155.80.

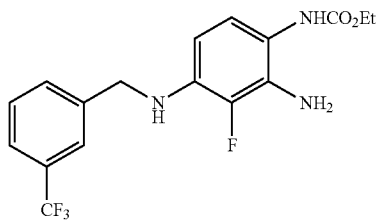

Ethyl (2-amino-3-fluoro-4-((3-(trifluoromethyl)benzyl) amino)phenyl)carbamate An oven-dried 5 mL round bottomed flask equipped with a magnetic stir bar under argon is charged with 3-fluoro-N4-(3-(trifluoromethyl)benzyl) benzene-1,2,4-triamine (0.06 g, 0.20 mmol), CH$_2$Cl$_2$ (1 mL) and DIPEA (0.043 mL, 0.25 mmol) at 0° C. Ethyl chloroformate (0.02 mL, 0.20 mmol) is added dropwise via syringe at 0° C. The resulting mixture is stirred for 1 h at 0° C. and then for 3 h at room temperature before water is added to the reaction mixture. The aqueous layer was extracted with CH2Cl2 (3×2 mL), the extracts were dried over Na$_2$SO$_4$, evaporated under reduced pressure. The residue was purified by flash column chromatography on silica gel (EtOAc/Hexanes=4:1 to 3:1) to afford the product as a dark red solid (0.045 g, 60%). Recrystallization from CH$_2$Cl$_2$/Hexanes gives a colorless crystal. m.p. 129.3-129.7° C.; 1H NMR (400 MHz, CDCl$_3$) δ 7.61 (s, 1H), 7.54 (app t, J=7.2 Hz, 2 H), 7.45 (t, J=7.6 Hz, 1 H), 6.74 (dd, J=8.4, 1.2 Hz, 1 H), 6.11 (br, 1 H), 6.02 (t, J=8.8 Hz, 1 H), 4.41 (d, J=5.2 Hz, 2 H), 4.30 (br, 1 H), 4.20 (q, J=7.2 Hz, 2 H), 3.86 (br, 2 H), 1.28 (t, J=7.2 Hz, 3 H); 13C NMR (100 MHz, acetone-d6) δ 156.01, 143.12, 141.77 (d, J=227.9 Hz), 135.48 (d, J=9.7 Hz), 132.39, 131.82, 130.94 (q, J=31.8 Hz), 130.08, 125.45 (q, J=271.5 Hz), 124.51 (q, J=3.9 Hz), 124.34 (q, J=3.9 Hz), 122.31, 116.45, 101.26, 61.19, 47.35, 14.95; 19F NMR (376 MHz, CDCl$_3$) δ −62.57 (s, 3 F), −155.49 (s, 1 F); IR (neat) 3405.8, 3290.2, 1675.9, 1452.2, 1329.1, 1246.2, 1159.5, 1112.9, 1071.9, 915.3, 700.9 cm−1; HRMS (ESI) m/z calcd for C$_{17}$H$_{18}$N$_3$O$_2$F$_4$ [M+H]+ 372.1330, found 372.1328.

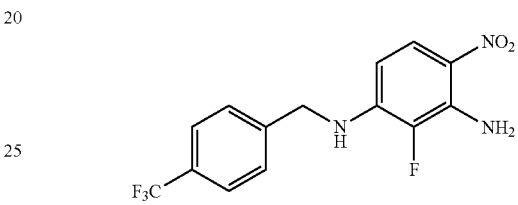

2-fluoro-4-nitro-N1-(4-(trifluoromethyl)benzyl)benzene-1,3-diamine To a stirred solution of 2,3-difluoro-6-nitroaniline (0.100 g, 0.557 mmol, 1.00 equiv) in dry DMSO (4.6 mL) were added 4-(trifluoromethyl)benzylamine (0.081 mL, 0.557 mmol, 1.00 equiv) followed by Et$_3$N (0.09 mL, 0.669 mmol, 1.20 equiv) and 1$_2$ (cat. 1 mg). The reaction mixture was heated to 120° C. for 24 h. The reaction mixture was cooled to room temperature, diluted with water (25 mL) and extracted with EtOAc (3×15 mL). The separated organic layer was washed with brine, dried over Na$_2$SO$_4$, filtered and concentrated under reduced pressure. The residue was purified by flash column chromatography on silica gel (EtOAc/Hexanes=1:10 to 1:5 to 1:3) to afford the product as a yellow solid (0.120 g, 65%). 1H NMR (500 MHz, CDCl$_3$) δ 7.86 (dd, J=9.5, 1.0 Hz, 1 H), 7.63 (d, J=8.0 Hz, 2 H), 7.44 (d, J=8.0 Hz, 2 H), 6.00-6.12 (m, 3H), 4.94 (br, 1H), 4.55 (d, J=6.0 Hz, 2 H); 13C NMR (100 MHz, acetone-d6) δ 144.15 (d, J=1.0 Hz), 141.45 (d, J=9.0 Hz), 137.61 (d, J=227.0 Hz), 135.80 (d, J=13.0 Hz), 128.75 (q, J=32.0 Hz), 127.56, 125.40 (q, J=4.0 Hz), 124.53 (d, J=4.0 Hz), 124.49 (q, J=269.0 Hz), 122.93 (d, J=2.0 Hz), 100.73 (d, J=4.0 Hz), 45.48; 19F NMR (376 MHz, acetone-d6) δ −62.87 (s, 3 F), −160.72 (s, 1 F); IR (neat) 3487.3, 3377.3, 1629.0, 1548.9, 1479.9, 1410.9, 1328.9, 1274.9, 1235.7, 1200.3, 1178.0, 1153.7, 1090.4, 1066.1, 1015.8, 786.5, 754.9 cm−1; HRMS (ESI) m/z calcd for C$_{14}$H$_{12}$N$_3$O$_2$F$_4$ [M+H]+ 330.0860, found 330.0858.

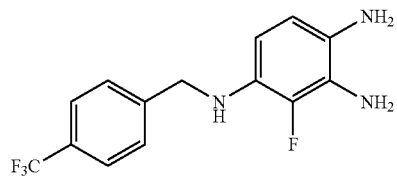

3-fluoro-N4-(4-(trifluoromethyl)benzyl)benzene-1,2,4-triamine To a stirred solution of 2-fluoro-4-nitro-N$_1$-(4-

(trifluoromethyl)benzyl)benzene-1,3-diamine (0.066 g, 0.2 mmol) in MeOH (0.5 mL) was added zinc powder (0.066 g, 1.00 mmol) followed by sat. ammonium chloride solution (0.19 mL) dropwise. After being stirred vigorously at room temperature for 5 h, the reaction mixture was filtered through celite, the filter cake was washed with EtOAc. The filter was extracted with EtOAc (3×2 mL), the combined organic layer was dried over $Na_2SO_4$, concentrated to afford the desired product as a dark red solid (0.060 g, 100%). Used in the next step without further purification. $^1$H NMR (400 MHz, $CDCl_3$) δ 7.58 (d, J=8.0 Hz, 2 H), 7.47 (d, J=8.0 Hz, 2 H), 6.35 (dd, J=8.4, 1.6 Hz, 1 H), 5.99 (t, J=8.4 Hz, 1H), 4.37 (s, 2 H), 4.02 (br, 1 H), 3.52 (br, 2 H), 3.13 (br, 2 H). HRMS (ESI) m/z calcd for $C_{14}H_{14}N_3F_4$ $[M+H]_+$ 300.1118, found 300.1113.

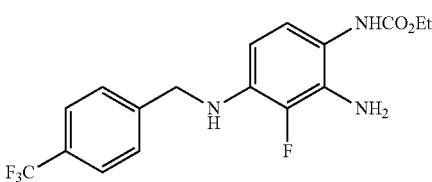

Ethyl (2-amino-3-fluoro-4-((4-(trifluoromethyl)benzyl) amino)phenyl)carbamate An oven-dried 5 mL round bottomed flask equipped with a magnetic stir bar under argon is charged with 3-fluoro-$N_4$-(4-(trifluoromethyl)benzyl)benzene-1,2,4-triamine (0.06 g, 0.20 mmol), $CH_2Cl_2$ (1 mL) and DIPEA (0.043 mL, 0.25 mmol) at 0° C. Ethyl chloroformate (0.02 mL, 0.20 mmol) is added dropwise via syringe at 0° C. The resulting mixture is stirred for 1 h at 0° C. and then for 3 h at room temperature before water is added to the reaction mixture. The aqueous layer was extracted with $CH_2Cl_2$ (3×2 mL), the extracts were dried over $Na_2SO_4$, evaporated under reduced pressure. The residue is purified by flash column chromatography on silica gel (EtOAc/Hexanes=4:1 to 3:1) to afford the product as a dark red solid. Recrystallization from $CH_2Cl_2$/Hexanes gives a colorless crystal (0.035 g, 47%). m.p. 171.4-172.2° C.; $^1$H NMR (400 MHz, $CDCl_3$) δ 7.59 (d, J=8.0 Hz, 2 H), 7.46 (d, J=8.0 Hz, 2 H), 6.73 (d, J=8.4 Hz, 1 H), 6.13 (br, 1 H), 5.99 (t, J=8.8 Hz, 1 H), 4.42 (s, 2 H), 4.33 (br, 1 H), 4.19 (q, J=7.2 Hz, 2 H), 3.86 (br, 1H), 1.29 (t, J=7.2 Hz, 3 H); $^{13}$C NMR (100 MHz, acetone-$d_6$) δ 156.02, 146.41, 141.74 (d, J=227.7 Hz), 135.42, 132.45, 129.25 (q, J=32.0 Hz), 128.47, 126.06 (q, J=3.9 Hz), 125.49 (q, J=271.0 Hz), 122.32, 116.40, 101.25, 61.19, 47.35, 14.96; $^{19}$F NMR (471 MHz, $CDCl_3$) δ −62.46 (s, 3 F), −156.12 (s, 1 F); IR (neat) 3399.7, 3338.2, 3299.0, 1675.6, 1643.9, 1617.8, 1528.4, 1489.2, 1478.0, 1442.6, 1323.3, 1248.8, 1157.5, 1112.7, 1103.4, 825.7, 781.0, 775.4, 767.9, 672.9 $cm^{-1}$; HRMS (ESI) m/z calcd for $C_{17}H_{18}N_3O_2F_4$ $[M+H]^+$ 372.1330, found 372.1327.

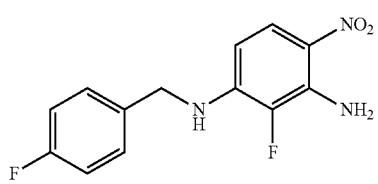

2-Fluoro-N1-(4-fluorobenzyl)-4-nitrobenzene-1,3-diamine To a stirred solution of 2,3-difluoro-6-nitroaniline (1.00 g, 5.57 mmol, 1.00 equiv) in dry DMSO (6 mL) were added 4-fluorobenzylamine (0.79 mL, 6.68 mmol, 1.20 equiv) followed by Et3N (0.93 mL, 6.68 mmol, 1.2 equiv) and 12 (cat. 5 mg). The reaction mixture was heated to 120° C. for 24 h. The reaction mixture was cooled to room temperature, diluted with water (30 mL) and extracted with EtOAc (3×30 mL). The separated organic layer was washed with brine, dried over $Na_2SO_4$, filtered and concentrated under reduced pressure. To the residue was added small amount (5 mL) of $Et_2O$, sonicated, filtered, the filter cake was again washed with $Et_2O$ (3×3 mL) to afford a yellow solid (1.20 g). The filtrate was concentrated in vacuo, the residue was purified by flash column chromatography on silica gel (EtOAc/Hexanes/$Et_3$N=1:4:0.1 to 1:3:0.1) to afford 0.2 g of the product as a yellow solid (1.40 g in total, 90%). 1H NMR (400 MHz, $CDCl_3$) δ 7.90 (dd, J=9.6, 2.0 Hz, 1 H), 7.33 (dd, J=8.4, 5.2 Hz, 2 H), 7.12-7.06 (m, 2 H), 6.12 (dd, J=9.6, 8.0 Hz, 1 H), 6.07 (br, 2 H), 4.86 (br, 1 H), 4.47 (s, 2 H); 13C NMR (125 MHz, acetone-d6) δ 162.96 (d, J=243.2 Hz), 142.57 (d, J=9.3 Hz), 138.54 (d, J=228.2 Hz), 136.73 (d, J=13.4 Hz), 136.24 (d, J=3.4 Hz), 129.91 (d, J=8.2 Hz), 125.38, 123.88 (d, J=2.6 Hz), 116.14 (d, J=21.6 Hz), 101.82 (d, J=3.5 Hz), 46.24; 19F NMR (376 MHz, CDCl3) δ −114.29 (s, 1F), −161.05 (s, 1 F), IR (neat) 3504.6, 3387.1, 3329.3, 3070.2, 2950.9, 1625.5, 1601.3, 1578.9, 1549.1, 1506.2, 1483.8, 1267.6, 1239.6, 1174.4, 1086.8, 991.7, 848.2, 837.0, 820.2, 805.3, 751.2 cm−1; HRMS (ESI) m/z calcd for $C_{13}H_{12}N_3O_2F_2$ [M+H]+ 280.0892, found 280.0890.

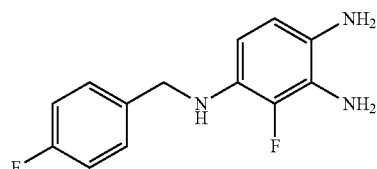

3-Fluoro-N4-(4-fluorobenzyl)benzene-1,2,4-triamine To a stirred solution of 2-fluoro-$N_1$-(4-fluorobenzyl)-4-nitrobenzene-1,3-diamine (0.200 g, 0.716 mmol) in MeOH (2 mL) was added zinc powder (0.230 g, 3.58 mmol) followed by sat. ammonium chloride solution (0.68 mL) dropwise. After being stirred vigorously at room temperature overnight, the reaction mixture was filtered through celite, the filter cake was washed with EtOAc. The filter was extracted with EtOAc (3×3 mL), the combined organic layer was dried over $Na_2SO_4$, concentrated to afford the desired product as a dark red solid (0.120 g, 67%). Used in the next step without further purification. $^1$H NMR (400 MHz, $CDCl_3$) δ 7.32 (dd, J=8.5, 5.5 Hz, 2 H), 7.04-6.98 (m, 2 H), 6.38 (d, J=8.5 Hz, 1 H), 6.03 (t, J=8.5 Hz, 1 H), 4.26 (s, 2 H), 3.21 (br, 5 H); $^{19}$F NMR (471 MHz, $CDCl_3$) δ −115.73 (s, 1 F), −155.78 (s, 1 F); HRMS (ESI) m/z calcd for $C_{13}H_{14}N_3F_2$ $[M+H]_+$ 250.1150, found 250.1148.

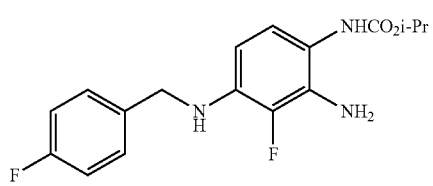

Isopropyl (2-amino-3-fluoro-4-((4-fluorobenzyl)amino) phenyl)carbamate An oven-dried 5 mL round bottomed flask equipped with a magnetic stir bar under argon is charged with 3-fluoro-N$_4$-(4-fluorobenzyl)benzene-1,2,4-triamine (0.120 g, 0.48 mmol), CH$_2$Cl$_2$ (2.5 mL) and DIPEA (0.10 mL, 0.60 mmol) at 0° C. Isopropyl chloroformate (1M in toluene, 0.48 mL) is added dropwise via syringe at 0° C. The resulting mixture is stirred for 1 h at 0° C. and then for 3 h at room temperature before water is added to the reaction mixture. The aqueous layer was extracted with CH$_2$Cl$_2$ (3×4 mL), the extracts were dried over Na$_2$SO4, evaporated under reduced pressure. The residue is purified by flash column chromatography on silica gel (EtOAc/Hexanes=4:1 to 3:1) to give a light red solid, which was washed with a small amount of Et$_2$O to afford a white solid (0.035 g, 21%). m.p. 177.5-178.2° C.; $^1$H NMR (500 MHz, CDCl$_3$) δ 7.21 (dd, J=8.5, 5.5 Hz, 2 H), 7.02 (app t, J=8.5 Hz, 2 H), 6.74 (d, J=8.5 Hz, 1 H), 6.11 (br, 1 H), 6.06 (t, J=8.5 Hz, 1 H), 4.98 (sept, J=6.0 Hz, 1 H), 4.31 (d, J=3.0 Hz, 2 H), 4.19 (br, 1 H), 3.86 (br, 2 H), 1.28 (d, J=6.0 Hz, 6 H); $^{13}$C NMR (125 MHz, CDCl$_3$) δ 162.23 (d, J=245.2 Hz), 155.08, 141.41 (d, J=233.8 Hz), 135.14 (d, J=10.4 Hz), 134.95 (d, J=3.1 Hz), 130.76 (d, J=11.4 Hz), 129.01 (d, J=8.1 Hz), 121.61, 115.61 (d, J=21.5 Hz), 115.45, 101.98, 69.19, 47.37, 22.23; $^{19}$F NMR (471 MHz, CDCl$_3$) δ −115.51 (s, 1 F), −156.21 (s, 1 F); IR (neat) 3407.6, 3338.7, 3295.8, 1675.9, 1646.0, 1618.1, 1532.3, 1487.6, 1442.8, 1323.5, 1284.4, 1263.9, 1249.0, 1155.8, 1112.9, 1101.7, 1066.3, 823.9, 781.1 cm$^{-1}$; HRMS (ESI) m/z calcd for C$_{17}$H$_{20}$N$_3$O$_2$F$_2$ [M+H]$_+$ 336.1518, found 336.1518.

2-fluoro-4-nitro-N$_1$-(3-(pentafluoro-λ$_6$-sulfanyl)benzyl) benzene-1,3-diamine To a stirred suspension of 2,3-difluoro-6-nitroaniline (0.500 g, 2.78 mmol, 1.00 equiv) in dry DMSO (5 mL) were added 3-(pentafluorosulphanyl)benzylamine (0. 714 g, 3.06 mmol, 1.1 equiv) followed by Et3N (0.43 mL, 3.06 mmol, 1.1 equiv) and I$_2$ (cat. 5 mg). The reaction mixture was heated to 120° C. for 24 h. The reaction mixture was cooled to room temperature, diluted with water (30 mL) and extracted with EtOAc (3×30 mL). The separated organic layer was washed with brine, dried over Na$_2$SO4, filtered and concentrated under reduced pressure. To the residue was added small amount of Et$_2$O (2 mL), sonicated, filtered, the filter cake was again washed with Et20 (3×3 mL) to afford a yellow solid (0.51 g). The filtrate was concentrated in vacuo, the residue was purified by flash column chromatography on silica gel (Acetone/Hexanes=1:10 to 1:4 to 1:3) to afford 0.17 g of the product as a yellow solid (0.68 g in total, 63%). $^1$H NMR (400 Hz, CDCl$_3$) δ 7.85 (dd, J=9.6, 1.6 Hz, 1 H), 7.72-7.68 (m, 2 H), 7.50-7.46 (m, 2 H), 6.07 (br, 2 H), 6.02 (dd, J=9.6, 8.0 Hz, 1 H), 4.50 (br, 1 H), 4.54 (d, J=1.5 Hz, 2 H); $^{13}$C NMR (100 MHz, acetone-d$_6$) δ 153.90 (t, J=16.1 Hz), 141.31 (d, J=9.4 Hz), 141.30, 137.63 (d, J=228.7 Hz), 135.83 (d, J=13.3 Hz), 135.68, 130.75, 129.47, 124.64 (t, J=4.7 Hz), 124.43 (t, J=4.7 Hz), 122.94 (d, J=2.8 Hz), 100.68 (d, J=3.0 Hz), 45.42; $^{19}$F NMR (376 MHz, CDCl$_3$) δ 84.01 (quint, J=150.4 Hz, 1 F), 62.73 (d, J=150.4 Hz, 4 F), −160.39 (s, 1 F); IR (neat) 3494.7, 3384.8, 1630.9, 1548.9, 1481.8, 1412.8, 1286.1, 1273.0, 1239.5, 1205.9, 1176.1, 1140.7, 1105.3, 1086.6, 890.9, 859.2, 820.1, 795.9, 775.4, 751.1, 687.8 cm$^{-1}$; HRMS (ESI) m/z calcd for C$_{13}$H$_{12}$N$_3$O$_2$F$_2$S [M+H]$_+$ 388.0549, found 388.0549.

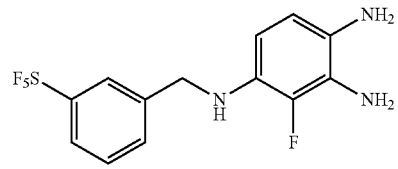

3-fluoro-N$_4$-(3-(pentafluoro-λ$_6$-sulfanyl)benzyl)benzene-1,2,4-triamine To a stirred solution of 2-fluoro-4-nitro-N$_1$-(3-(pentafluoro-λ$_6$-sulfanyl)benzyl)benzene-1,3-diamine (0.500 g, 1.29 mmol) in MeOH (4 mL) was added zinc powder (0.422 g, 6.45 mmol) followed by sat. ammonium chloride solution (1.22 mL) dropwise. After being stirred vigorously at room temperature overnight, the reaction mixture was filtered through celite, the filter cake was washed with EtOAc. The filter was extracted with EtOAc (3×5 mL), the combined organic layer was dried (Na$_2$SO4), concentrated to afford the desired product (0.390 g, 85%) as a red solid. Used in the next step without further purification. $^1$H NMR (400 MHz, CDCl$_3$) δ 7.74 (s, 1H), 7.64 (d, J=8.4 Hz, 1H), 7.51 (d, J=7.6 Hz, 1H), 7.41 (t, J=8.0 Hz, 1H), 6.39 (d, J=7.6 Hz, 1H), 5.98 (t, J=8.4 Hz, 1H), 4.35 (s, 2H), 3.32 (br, 5H).

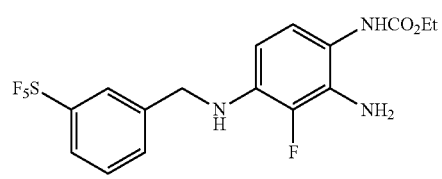

Ethyl (2-amino-3-fluoro-4-((3-(pentafluoro-λ$_6$-sulfanyl)benzyl)amino)phenyl)carbamate An oven-dried 5 mL round bottomed flask equipped with a magnetic stir bar under argon is charged with 3-fluoro-N$_4$-(3-(pentafluoro-λ$_6$-sulfanyl)benzyl)benzene-1,2,4-triamine (0.20 g, 0.56 mmol), CH$_2$Cl$_2$ (3 mL) and DIPEA (0.12 mL, 0.7 mmol) at 0° C. Ethyl chloroformate (0.055 mL, 0.56 mmol) is added dropwise via syringe at 0° C. The resulting mixture is stirred for 1 h at 0° C. and then for 3 h at room temperature before water is added to the reaction mixture. The aqueous layer was extracted with CH$_2$Cl$_2$ (3×5 mL), the extracts was dried over Na$_2$SO$_4$, evaporated under reduced pressure. The residue was purified by flash column chromatography on silica gel (EtOAc/Hexanes=5:1 to 4:1 to 3:1) to afford the product as a yellow solid. Recrystallization from CH$_2$Cl$_2$/Hexanes afford a white solid (0.123 g, 44%). m.p. 141.3-142.1° C.; $^1$H NMR (400 MHz, CDCl$_3$) δ 7.73 (s, 1 H), 7.65 (d, J=8.0 Hz, 1 H), 7.50 (d, J=7.6 Hz, 1 H), 7.42 (t, J=8.0 Hz, 1 H), 6.74 (d, J=7.6 Hz, 1 H), 6.24 (br, 1 H), 6.00 (t, J=8.8 Hz, 1 H), 4.40 (s, 2H), 4.19 (q, J=7.2 Hz, 2 H), 3.98 (br, 2 H), 1.28 (t, J=7.2 Hz, 3 H); $^{13}$C NMR (100 MHz, CDCl$_3$) δ 155.49, 154.36 (quint, J=16.9 Hz), 141.34 (d, J=233.6 Hz), 140.72, 134.71 (d, J=9.8 Hz), 130.85, 130.28, 129.15, 124.95 (t, J=4.6 Hz), 124.75 (t, J=4.61 Hz), 121.70, 115.64, 101.91, 61.70, 47.60, 14.64; $^{19}$F NMR (565 MHz, CDCl$_3$) δ 84.53 (quint, J=146.9 Hz, 1 F), 62.79 (d, J=146.9 Hz, 4 F), −155.77 (s, 1 F); IR (neat) 3420.2, 3375.41, 2985.9, 1688.7, 1636.5, 1524.6, 1483.6, 1287.9, 1254.4, 1241.3, 829.4, 816.4, 786.5, 688.7 cm$^{-1}$; HRMS (ESI) m/z calcd for C$_{16}$H$_{18}$N$_3$O$_2$F$_6$S [M+H]$^+$ 430.1018, found 430.1015.

Several embodiments are described below in the following numbered clauses:

1. A compound, or a pharmaceutically acceptable salt thereof, having a formula of:

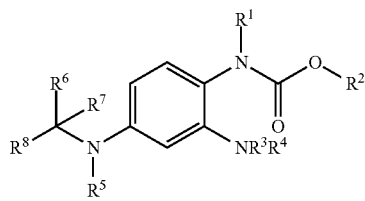

wherein R$^1$ is H or optionally-substituted alkyl;

R$^2$ is optionally-substituted alkyl;

R$^3$ and R$^4$ are each independently H or optionally-substituted alkyl;

R$^5$ is H, optionally-substituted alkyl, acyl, or alkoxycarbonyl;

R$^6$ and R$^7$ are each independently H, deuterium, optionally-substituted alkyl, or R$^6$ and R$^7$ together form a carbocyclic; and R$^8$ is optionally-substituted thiazolyl, optionally-substituted thiophenyl, or substituted phenyl, provided that if R$^8$ is 4-fluorophenyl, then R$^2$ is substituted alkyl or at least one of R$^6$ or R$^7$ is not H, and provided that if R$^8$ is substituted thiophenyl, then at least one substituent on the thiophenyl is halo-substituted sulfanyl.

2. The compound of clause 1, wherein R$^1$ is H.

3. The compound of clause 1 or 2, wherein R$^2$ is C$_1$-C$_6$ alkyl.

4. The compound of clause 1 or 2, wherein R$^2$ is carbocyclic-substituted alkyl or heterocyclic-substituted alkyl.

5. The compound of any one of clauses 1 to 4, wherein R$^3$ and R$^4$ are each H.

6. The compound of any one of clauses 1 to 5, wherein R$^5$ is H.

7. The compound of any one of clauses 1 to 6, wherein R$^6$ and R$^7$ are both H; R$^6$ and R$^7$ are both deuterium; R$^6$ and R$^7$ together form a cycloalkyl; or at least one of R$^6$ or R$^7$ is a substituted alkyl.

8. The compound of any one of clauses 1 to 7, wherein R$^8$ is selected from:

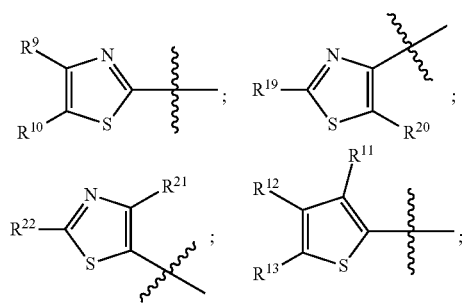

-continued

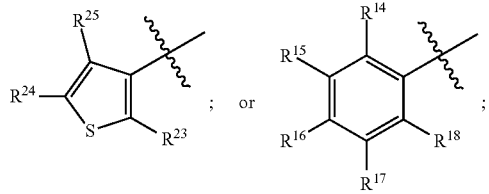

wherein R$^9$-R$^{25}$ are each independently H, halogen, optionally-substituted sulfanyl, or optionally-substituted alkyl.

9. The compound of clause 8, wherein R$^8$ is:

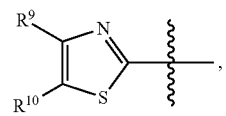

wherein at least one of R$^9$ or R$^{10}$ is halogen.

10. The compound of clause 8, wherein R$^8$ is:

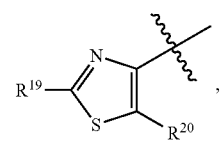

wherein at least one of R$^{19}$ or R$^{20}$ is halogen.

11. The compound of clause 8, wherein R$^8$ is:

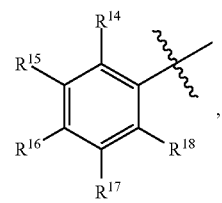

wherein at least one of R$^{14}$-R$^{18}$ is substituted sulfanyl or haloalkyl; or wherein R$^{16}$ is F.

12. The compound of clause 11, wherein at least one of R$^{14}$-R$^{18}$ is —SF$_5$ or CF$_3$.

13. The compound of clause 8, wherein R$^8$ is:

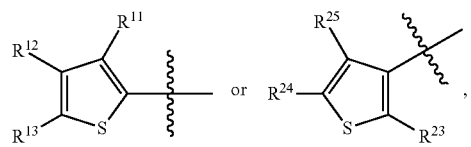

wherein at least one of R$^{11}$-R$^{13}$ or R$^{23}$-R$^{25}$ is substituted sulfanyl.

14. A pharmaceutical composition comprising at least one compound of any one of clauses 1 to 13, and at least one pharmaceutically acceptable additive.

15. A method of treating tinnitus in a subject, comprising administering to the subject in need thereof a therapeutically effective amount of a compound, or a pharmaceutically acceptable salt thereof, having a formula of:

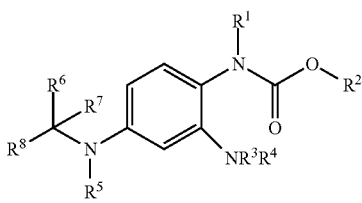

wherein $R^1$ is H or optionally-substituted alkyl;
$R^2$ is optionally-substituted alkyl;
$R^3$ and $R^4$ are each independently H or optionally-substituted alkyl;
$R^5$ is H, optionally-substituted alkyl, acyl, or alkoxycarbonyl;
$R^6$ and $R^7$ are each independently H, deuterium, optionally-substituted alkyl, or $R^6$ and $R^7$ together form a carbocyclic; and
$R^8$ is optionally-substituted thiazolyl, optionally-substituted thiophenyl, or substituted phenyl, provided that if $R^8$ is 4-fluorophenyl, then $R^2$ is substituted alkyl or at least one of $R^6$ or $R^7$ is not H.

16. The method of clause 15, comprising administering to the subject at least compound of any one of clauses 1 to 13.

17. A method comprising treating a subject suffering from or susceptible to conditions that are ameliorated by Kv7.2/3 potassium channel opening, comprising administering to the subject a therapeutically effective amount of a compound of any one of clauses 1 to 13.

18. A method of producing an anti-epileptic, muscle relaxing, fever reducing, peripherally analgesic or anti-convulsive effect in a subject in need thereof, comprising administering to the subject a therapeutically effective amount of compound of any one of clauses 1 to 13.

19. A method for treating a neurotransmission disorder, CNS disorder, functional bowel disorder, a neurodegenerative disease, a cognitive disorder, or a migraine in a subject, comprising administering to the subject in need thereof a therapeutically effective amount of a compound of any one of clauses 1 to 13.

In view of the many possible embodiments to which the principles of the disclosed compounds, compositions and methods may be applied, it should be recognized that the illustrated embodiments are only preferred examples of the invention and should not be taken as limiting the scope of the invention.

What is claimed is:

1. A compound, or pharmaceutically acceptable salt thereof, having a formula I of:

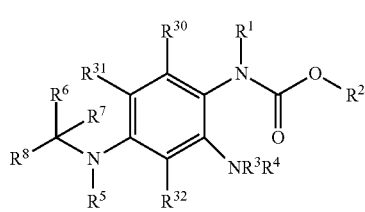

wherein $R^1$ is H or optionally-substituted alkyl;
$R^2$ is optionally-substituted alkyl;
$R^3$ and $R^4$ are each independently H or optionally-substituted alkyl;
$R^5$ is H, optionally-substituted alkyl, acyl, or alkoxycarbonyl;

$R^6$ and $R^7$ are each independently H, deuterium, optionally-substituted alkyl, or $R^6$ and $R^7$ together form a carbocycle;
$R^8$ is optionally-substituted thiazolyl, optionally-substituted thiophenyl, or substituted phenyl, provided that if $R^8$ is 4-halophenyl, then $R^2$ is substituted alkyl having one or more hydrogen atoms substituted with a substituent selected from halogen, cycloalkyl, alkoxy, amino, hydroxyl, aryl, alkenyl, or carboxyl, or at least one of $R^6$ or $R^7$ is not H;
$R^{30}$ and $R^{31}$ are each independently H, deuterium, halogen, substituted sulfanyl, or optionally-substituted alkoxy; and
$R^{32}$ is deuterium, halogen, substituted sulfanyl, or optionally-substituted alkoxy.

2. A compound, or a pharmaceutically acceptable salt thereof, having a formula II of:

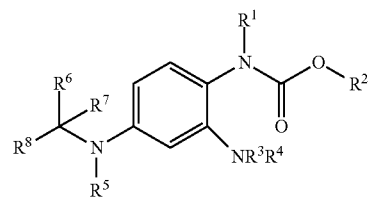

wherein $R^1$ is H or optionally-substituted alkyl;
$R^2$ is optionally-substituted alkyl;
$R^3$ and $R^4$ are each independently H or optionally-substituted alkyl;
$R^5$ is H, optionally-substituted alkyl, acyl, or alkoxycarbonyl;
$R^6$ and $R^7$ are each independently H, deuterium, optionally-substituted alkyl, or $R^6$ and $R^7$ together form a carbocycle; and
$R^8$ is optionally-substituted thiazolyl.

3. The compound of claim 1, wherein $R^1$ is H.

4. The compound of claim 1, wherein $R^2$ is $C_1$-$C_6$ alkyl.

5. The compound of claim 4, wherein $R^2$ is carbocyclic-substituted alkyl or heterocyclic-substituted alkyl.

6. The compound of claim 1, wherein $R^3$ and $R^4$ are each H.

7. The compound of claim 1, wherein $R^5$ is H.

8. The compound of claim 1, wherein $R^6$ and $R^7$ are both H; $R^6$ and $R^7$ are both deuterium; $R^6$ and $R^7$ together form a cycloalkyl; or at least one of $R^6$ or $R^7$ is a substituted alkyl.

9. The compound of claim 1, wherein $R^8$ is selected from:

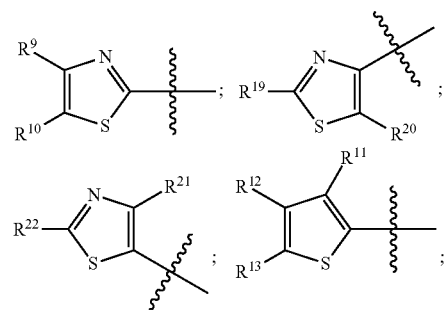

-continued

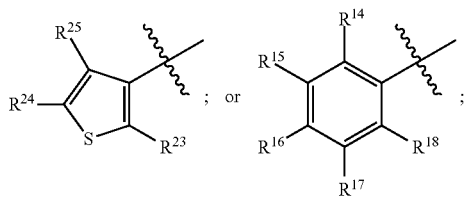

wherein $R^9$-$R^{25}$ are each independently H, halogen, optionally-substituted sulfanyl, or optionally-substituted alkyl.

10. The compound of claim 9, wherein $R^8$ is:

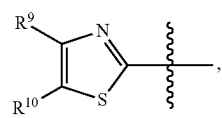

wherein at least one of $R^9$ or $R^{10}$ is halogen.

11. The compound of claim 9, wherein $R^8$ is:

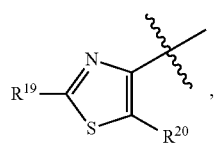

wherein at least one of $R^{19}$ or $R^{20}$ is halogen.

12. The compound of claim 9, wherein $R^8$ is:

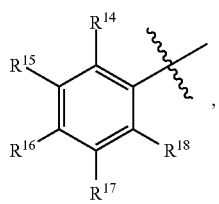

wherein at least one of $R^{14}$-$R^{18}$ is substituted sulfanyl or haloalkyl; or wherein $R^{16}$ is F.

13. The compound of claim 12, wherein at least one of $R^{14}$-$R^{18}$ is —SF$_5$ or CF$_3$.

14. The compound of claim 9, wherein $R^8$ is:

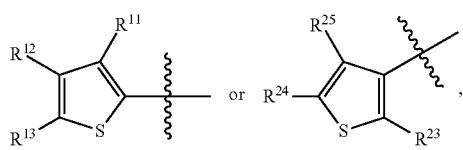

wherein at least one of $R^{11}$-$R^{13}$ or $R^{23}$-$R^{25}$ is substituted sulfanyl.

15. The compound of claim 1, wherein $R^8$ is:

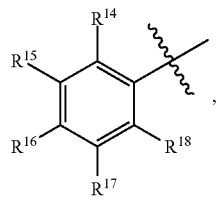

wherein at least one of $R^{14}$-$R^{18}$ is halo-substituted sulfanyl, haloalkyl or halogen.

16. The compound of claim 15, wherein at least one of $R^{14}$-$R^{18}$ is —SF$_5$ or —CF$_3$.

17. The compound of claim 16, wherein $R^{15}$, $R^{16}$, or $R^{17}$ is —SF$_5$ or —CF$_3$.

18. The compound of claim 1, wherein $R^{32}$ is —F, and $R^{30}$ and $R^{31}$ are each H.

19. A compound, or a pharmaceutically acceptable salt thereof, wherein the compound is:

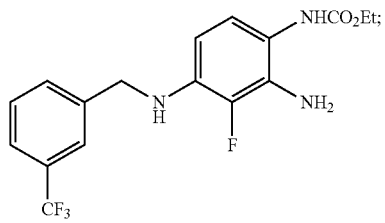

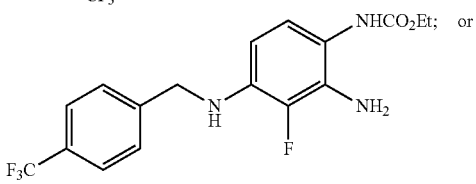

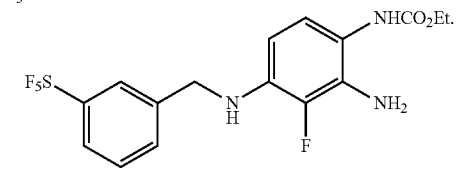

20. A pharmaceutical composition comprising at least one compound of claim 1, and at least one pharmaceutically acceptable additive.

21. A method of treating tinnitus in a subject, comprising administering to the subject in need thereof a therapeutically effective amount of at least one compound of claim 1.

22. A method comprising treating a subject suffering from or susceptible to conditions that are ameliorated by Kv7.2/3 potassium channel opening, comprising administering to the subject a therapeutically effective amount of a compound of claim 1.

23. A method of producing an anti-epileptic, muscle relaxing, fever reducing, peripherally analgesic or anti-convulsive effect in a subject in need thereof, comprising administering to the subject a therapeutically effective amount of compound of claim 1.

24. A method for treating epilepsy in a subject, comprising administering to the subject in need thereof a therapeutically effective amount of a compound of claim 1.

25. A compound, or pharmaceutically acceptable salt thereof, having a formula of:

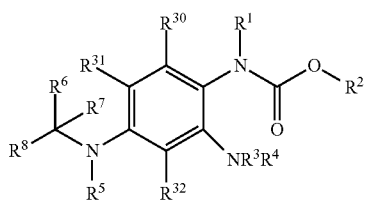

wherein $R^1$ is H or optionally-substituted alkyl;

$R^2$ is substituted alkyl having one or more hydrogen atoms substituted with a substituent selected from halogen, cycloalkyl, alkoxy, amino, hydroxyl, aryl, alkenyl, or carboxyl;

$R^3$ and $R^4$ are each independently H or optionally-substituted alkyl;

$R^5$ is H, optionally-substituted alkyl, acyl, or alkoxycarbonyl;

$R^6$ and $R^7$ are each independently H, deuterium, optionally-substituted alkyl, or $R^6$ and $R^7$ together form a carbocycle;

$R^8$ is optionally-substituted thiazolyl, optionally-substituted thiophenyl, or substituted phenyl; and $R^{30}$, $R^{31}$ and $R^{32}$ are each independently H, deuterium, halogen, substituted sulfanyl, or optionally-substituted alkoxy.

26. A compound, or pharmaceutically acceptable salt thereof, having a formula of:

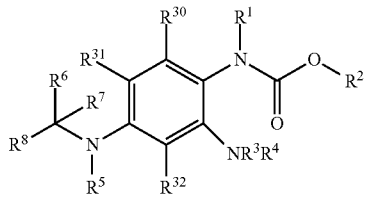

wherein $R^1$ is H or optionally-substituted alkyl;

$R^2$ is optionally-substituted alkyl;

$R^3$ and $R^4$ are each independently H or optionally-substituted alkyl;

$R^5$ is H, optionally-substituted alkyl, acyl, or alkoxycarbonyl;

$R^6$ and $R^7$ are each independently H, deuterium, optionally-substituted alkyl, or $R^6$ and $R^7$ together form a carbocycle, provided at least one $R^6$ or $R^7$ is not H;

$R^8$ is optionally-substituted thiazolyl, optionally-substituted thiophenyl, or substituted phenyl, provided that if $R^8$ is 4-halophenyl, then $R^2$ is substituted alkyl or branched alkyl or at least one of $R^6$ or $R^7$ is not H; and $R^{30}$, $R^{31}$ and $R^{32}$ are each independently H, deuterium, halogen, substituted sulfanyl, or optionally-substituted alkoxy.

27. A compound, or a pharmaceutically acceptable salt thereof, having a formula of:

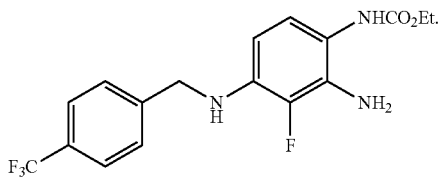

wherein $R^1$ is H or optionally-substituted alkyl;

$R^2$ is optionally-substituted alkyl;

$R^3$ and $R^4$ are each independently H or optionally-substituted alkyl;

$R^5$ is H, optionally-substituted alkyl, acyl, or alkoxycarbonyl;

$R^6$ and $R^7$ are each independently H, deuterium, optionally-substituted alkyl, or $R^6$ and $R^7$ together form a carbocycle; and $R^8$ is substituted thiophenyl, wherein at least one substituent on the thiophenyl is halo-substituted sulfanyl.

28. A compound, or a pharmaceutically acceptable salt thereof, wherein the compound is:

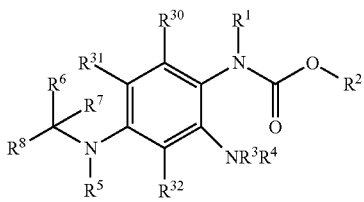

29. A compound, or pharmaceutically acceptable salt thereof, having a formula I of:

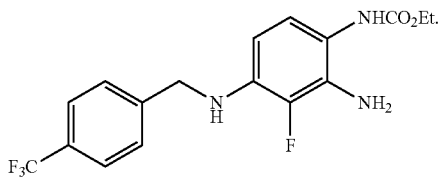

wherein $R^1$ is H or optionally-substituted alkyl;

$R^2$ is optionally-substituted alkyl;

$R^3$ and $R^4$ are each independently H or optionally-substituted alkyl;

$R^5$ is H, optionally-substituted alkyl, acyl, or alkoxycarbonyl;

$R^6$ and $R^7$ are each independently H, deuterium, optionally-substituted alkyl, or $R^6$ and $R^7$ together form a carbocycle;

$R^8$ is

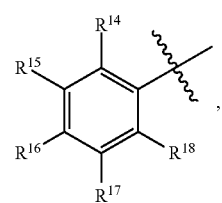

wherein at least one of $R^{14}$-$R^{18}$ is substituted sulfanyl or haloalkyl; and $R^3$ and $R^{31}$ are each independently H, deuterium, halogen, substituted sulfanyl, or optionally-substituted alkoxy; and $R^{32}$ is deuterium, halogen, substituted sulfanyl, or optionally-substituted alkoxy.

30. The compound of claim 29, wherein $R^{32}$ is halogen.

31. The compound of claim 29, wherein $R^{32}$ is —F.

32. The compound of claim 29, wherein at least one of $R^{14}$-$R^{18}$ is halo-substituted sulfanyl.

33. The compound of claim 29, wherein at least one of $R^{14}$-$R^{18}$ is haloalkyl.

34. The compound of claim 29, wherein at least one of $R^{14}$-$R^{18}$ is —SF$_5$.

35. The compound of claim 29, wherein at least one of $R^{14}$-$R^{18}$ is —CF$_3$.

36. The compound of claim 29, wherein $R^{16}$ is —SF$_5$.

37. The compound of claim 29, wherein $R^{16}$ is —CF$_3$.

38. The compound of claim 29, wherein $R^2$ is alkyl.

39. The compound of claim 29, wherein $R^2$ is $C_1$-$C_6$ alkyl.

40. The compound of claim 29, wherein $R^2$ is ethyl.

41. The compound of claim 29, wherein $R^3$, $R^4$, $R^5$, $R^6$, and $R^7$ are each H.

42. The compound of claim 41, wherein $R^{32}$ is —F and $R^{16}$ is —CF$_3$.

43. The compound of claim 42, wherein $R^2$ is alkyl.

44. The compound of claim 43, wherein $R^3$ and $R^{31}$ are each H.

45. The compound of claim 29, wherein $R^{15}$, $R^{16}$, or $R^{17}$ is —SF$_5$ or —CF$_3$.

46. The compound of claim 45, wherein $R^1$, $R^1$, $R^3$, $R^4$, $R^5$, $R^6$, and $R^7$ are each H; $R^2$ is alkyl; and $R^{32}$ is —F.

47. A method for treating bipolar disorder in a subject, comprising administering to the subject in need thereof a therapeutically effective amount of a compound of claim 1.

48. A method of producing an anti-epileptic effect in a subject in need thereof, comprising administering to the subject a therapeutically effective amount of compound of claim 1.

49. A method of treating tinnitus in a subject, comprising administering to the subject in need thereof a therapeutically effective amount of at least one compound of claim 12.

50. A method of treating epilepsy in a subject, comprising administering to the subject in need thereof a therapeutically effective amount of at least one compound of claim 12.

* * * * *